(12) United States Patent
Zhang et al.

(10) Patent No.: US 8,410,272 B2
(45) Date of Patent: Apr. 2, 2013

(54) PYRAZOLYLBENZOTHIAZOLE DERIVATIVES AND THEIR USE AS THERAPEUTIC AGENTS

(75) Inventors: Zaihui Zhang, Vancouver (CA); Timothy S Daynard, Vancouver (CA); Shisen Wang, Coquitlam (CA); Xinyao Du, Richmond (CA); Gregory B Chopiuk, San Diego, CA (US); Jun Yan, Coquitlam (CA); Jianxin Chen, Vancouver (CA); Serguei V Sviridov, Burnaby (CA)

(73) Assignee: Dermira (Canada), Inc., Redwood City, CA (US)

( * ) Notice: Subject to any disclaimer, the term of this patent is extended or adjusted under 35 U.S.C. 154(b) by 0 days.

(21) Appl. No.: 12/910,744

(22) Filed: Oct. 22, 2010

(65) Prior Publication Data
US 2011/0178126 A1     Jul. 21, 2011

Related U.S. Application Data

(63) Continuation of application No. 10/521,948, filed as application No. PCT/CA03/01078 on Jul. 23, 2003, now Pat. No. 7,847,101.

(51) Int. Cl.
A61K 31/437 (2006.01)
C07D 513/04 (2006.01)
(52) U.S. Cl. .............................. 546/114; 514/301
(58) Field of Classification Search .................. 546/114
See application file for complete search history.

(56) References Cited

U.S. PATENT DOCUMENTS

| 4,269,846 A | 5/1981 | Huang et al. | 424/269 |
|---|---|---|---|
| 6,136,831 A | 10/2000 | Aotsuka et al. | 514/367 |

FOREIGN PATENT DOCUMENTS

| JP | 52 108427 | 9/1977 |
|---|---|---|
| WO | WO 01/53331 | 7/2001 |
| WO | WO 01/77080 | 10/2001 |
| WO | WO 02/062804 | 8/2002 |
| WO | WO-03/042214 A2 * | 5/2003 |
| WO | WO 03/055860 | 7/2003 |
| WO | WO-03/080610 A1 * | 10/2003 |

OTHER PUBLICATIONS

Nawwar et al., Anales de Quimica, (1993), 89(3), pp. 375-378.*
Civcir, Journal of Molecular Structure (Theochem), vol. 545, (2001), pp. 7-15.*
Chemical Abstracts Registry No. 448187-87-9, indexed in the Registry file on STN CAS Online Sep. 9, 2002.*
Chemical Abstracts Registry No. 448187-99-3, indexed in the Registry file on STN CAS Online Sep. 9, 2002.*
Abdallah et al., "A convenient synthesis of 5-amino-4-(2-benzothiazolyl)pyrazoles," *Indian Journal of Chemistry 36B*: 1175-1177, Dec. 1997.
Augustin and Dölling, "Synthese von 2-[Benzazoly1-(2)]-3,3-bis-(alkylthio)-acrylnitrilen and Umsetzungen mit N-Nucleophilen," *Journal f. prakt. Chemie*. 324(1): 3-11, 1982.
Bontems et al., "Guanosine Analogues. Synthesis of Nucleosides of Certain 3-Substituted 6-Aminopyrazolo[3,4-d]pyrimidin-4(5H)-ones as Potential Immunotherapeutic Agents," *J. Med. Chem.* 33(8): 2174-2178, 1990.
Cama et al., "Total Synthesis of Thienamycin Analogs—III Syntheses of 2-Aryl and 2-Heteroaryl Analogs of Thienamycin," *Tetrahedron* 39(15): 2531-2549, 1983.
CA Registry No. 385424-29-3, indexed in the Registry file on STN Jan. 22, 2002.
CA Registry No. 302575-58-2, indexed in the Registry file on STN Nov. 13, 2000.
Chemical Abstracts, Accession No. 133:281720, 1999.
Chemical Abstracts, Accession No. 122:290759, 1994.
Chemical Abstracts, Accession No. 120:164052, 1993.
Chemical Abstracts, Accession No. 101:151788, 1983.
Chemical Abstracts, Accession No. 80:108415, 1973.
Chemical Abstracts (CHEMCATS), Order Nos. 7211230280 & 7211230233, Jan. 1, 2004.
Chemical Abstracts (CHEMCATS), Order Nos. 6946294 & 6945075, Jan. 12, 2005.
Dawood, K.M., "One-pot Synthesis of Novel Polysubstituted Pyrazole and Pyrrolo[2,1-b]benzothiazole Derivatives," *J. Chem. Res.* (S): 128-129, 1998.
Dawood et al., "Heterocyclic Synthesis via Enaminonitriles: A Convenient Route to Some New Pyrazole, Isoxazole, Pyrimidine, Pyrazolo [1, 5-a]pyrimidine, Pyrimido [1, 2-a]benzimidazole and Pyrido[1, 2-a]benzimidazole Derivatives," *J. Chem. Res.*, No. 4, pp. 208-209, 1998.
Dawood et al., CA 129:67759, 1998.
Fadda et al, "Revised Synthesis of Some New 2-Heterocyclic Benzothiazolyl Derivatives of Biological Interest," *Phosphorus, Sulfur and Silicon* 155: 59-66, 1999.
Farag et al., "Convenient Route to Some New Pyrazole, Pyrazolo[3,4-d]-pyridazine and 2,3-Dihydrothiadiazole Derivatives Incorporating a Benzothiazole Moiety," *J. Chem. Res.* (S): 416-417, 1996.

(Continued)

Primary Examiner — Laura L Stockton
(74) Attorney, Agent, or Firm — Hai Han; Seed IP Law Group PLLC

(57) ABSTRACT

Pharmaceutical compositions and compounds are provided. The compounds of the invention have use as therapeutic agents, e.g., they demonstrate anti-proliferative, anti-inflammatory, anti-angiogenic, anti-migration activities. In one embodiment of the invention, formulations of the compounds in combination with a physiologically acceptable carrier are provided. The pharmaceutical formulations are useful in the treatment of, e.g., anti-inflammatory, renal, and hyperproliferative disorders. The compounds of the invention are pyrazolylbenzothiazole derivatives of the following formula (1)

(1)

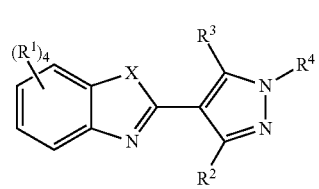

wherein X, $R^1$, $R^2$, $R^3$ and $R^4$ are described herein.

14 Claims, No Drawings

OTHER PUBLICATIONS

Fogagnolo et al., "Homochiral (R)- and (S)-1-heteroaryl- and 1-aryl-2-propanols via microbial redox," *Tetrahedron: Asymmetry* 9: 2317-2327, 1998.

Gorbulenko et al., *Khimiya Geterotsiklicheskikh Soedinenii* 4: 464-471, 1994.

Gorbulenko et al., *Khimiya Geterotsiklicheskikh Soedinenii* 4: 464-471, 1994 [English translation].

Nawwar et al., "Synthesis of 2-substituted Benzothiazoles Containing Amino Acid, Imino or Heteroaryl Moieties with Anticipated Fungicidal Activity," *Collection of Czechoslovak Chemical Communications* 60(12):2200-2208, 1995.

Pivsa-Art et al., "Palladium-Catalyzed Arylation of Azole Compounds with Aryl Halides in the Presence of Alkali Metal Carbonates and the Use of Copper Iodide in the Reaction," *Bull. Chem. Soc. Jpn.* 71(2): 467-473, 1998.

Sakamoto et al., "Diels—Alder reaction of benzylidene(cyano)methyl-1,3-benzoxa/thiazoles as stable 1-azabuta-1,3-dienes," *J. Chem. Soc. Perkin Trans.*: 1759-1770, 1995.

Shi et al., "Antitumor Benzothiazoles. 3. Synthesis of 2-(4-Aminophenyl)benzothiazoles and Evaluation of Their Activities against Breast Cancer Cell Lines in Vitro and in Vivo," *J. Med. Chem.* 39(17): 3375-3384, 1996.

Souillac et al., "Characterization of Delivery Systems, Differential Scanning Calorimetry," in *Encyclopedia of Controlled Drug Delivery*, 1999, John Wiley & Sons, pp. 212-227.

Vippagunta et al., "Crystalline Solids," *Advanced Drug Delivery Reviews* 48: 3-26, 2001.

\* cited by examiner

PYRAZOLYLBENZOTHIAZOLE DERIVATIVES AND THEIR USE AS THERAPEUTIC AGENTS

CROSS-REFERENCE TO RELATED APPLICATIONS

This application is a continuation application of U.S. application Ser. No. 10/521,948, filed Jan. 23, 2006 (U.S. Pat. No. 7,847,101), which is a §371 national phase conversion of International Patent Application No. PCT/CA2003/001078, filed Jul. 23, 2003. These applications are incorporated herein by reference in their entireties.

FIELD OF THE INVENTION

This invention is directed to pyrazolylbenzothiazole derivatives, pharmaceutical compositions containing the derivatives and methods of using the derivatives as therapeutic agents.

BACKGROUND OF THE INVENTION

It has become increasingly clear in recent years that cell death is as important to the health of a multicellular organism as cell division; where proliferation exists, so must a means of regulating its cellular progeny. By repeated cell division and differentiation throughout development or tissue repair, surplus or even harmful cells are generated, and they must be removed or killed. In adults, senescent cells are removed and replaced by newly generated cells to maintain homeostasis.

The delicate interplay between growth and cell death in an organism is mirrored in the complex molecular balance that determines whether an individual cell undergoes division; arrests in the cell cycle; or commits to programmed cell death. Signal transduction is the term describing the process of conversion of extracellular signals, such as hormones, growth factors, neurotransmitters, cytokines, and others, to a specific intracellular response such as gene expression, cell division, or apoptosis. This process begins at the cell membrane where an external stimulus initiates a cascade of enzymatic reactions inside the cell that typically include phosphorylation of proteins as mediators of downstream processes which most often end in an event in the cell nucleus. The checks and balances of these signal transduction pathways can be thought of as overlapping networks of interacting molecules that control "go-no go" control points. Since almost all known diseases exhibit dysfunctional aspects in these networks, there has been a great deal of enthusiasm for research that provides targets and therapeutic agents based on signal transduction components linked to disease.

Dysregulation of cell proliferation, or a lack of appropriate cell death, has wide ranging clinical implications. A number of diseases associated with such dysregulation involve hyperproliferation, inflammation, tissue remodelling and repair. Familiar indications in this category include cancers, restenosis, neointimal hyperplasia, angiogenesis, endometriosis, lymphoproliferative disorders, graft-rejection, polyposis, loss of neural function in the case of tissue remodelling, and the like. Such cells may lose the normal regulatory control of cell division, and may also fail to undergo appropriate cell death.

In one example, epithelial cells, endothelial cells, muscle cells, and others undergo apoptosis when they lose contact with extracellular matrix, or bind through an inappropriate integrin. This phenomenon, which has been termed "anoikis" (the Greek word for "homelessness"), prevents shed epithelial cells from colonizing elsewhere, thus protecting against neoplasia, endometriosis, and the like. It is also an important mechanism in the initial cavitation step of embryonic development, in mammary gland involution, and has been exploited to prevent tumor angiogenesis. Epithelial cells may become resistant to anoikis through overactivation of integrin signaling. Anoikis resistance can also arise from the loss of apoptotic signaling, for example, by overexpression of Bcl-2 or inhibition of caspase activity.

An aspect of hyperproliferation that is often linked to tumor growth is angiogenesis. The growth of new blood vessels is essential for the later stages of solid tumor growth. Angiogenesis is caused by the migration and proliferation of the endothelial cells that form blood vessels.

In another example, a major group of systemic autoimmune diseases is associated with abnormal lymphoproliferation, as a result of defects in the termination of lymphocyte activation and growth. Often such diseases are associated with inflammation, for example with rheumatoid arthritis, insulin dependent diabetes mellitus, multiple sclerosis, systemic lupus erythematosus, and the like. Recent progress has been made in understanding the causes and consequences of these abnormalities. At the molecular level, multiple defects may occur, which result in a failure to set up functional apoptotic machinery.

The development of compounds that inhibit hyperproliferative diseases, particularly where undesirable cells are selectively targeted, is of great medical and commercial interest.

RELATED LITERATURE

The regulation of integrin linked kinase by phosphatidylinositol (3,4,5) trisphosphate is described by Delcommenne et al. (1998) *Proc Natl Acad Sci* 95:11211-6. Activated nitriles in heterocyclic synthesis are discussed in Kandeel et al. (1985) *J. Chem. Soc. Perkin. Trans* 1499.

SUMMARY OF THE INVENTION

The invention is directed to pharmaceutical compositions comprising a pharmaceutically acceptable excipient and a compound of formula (1):

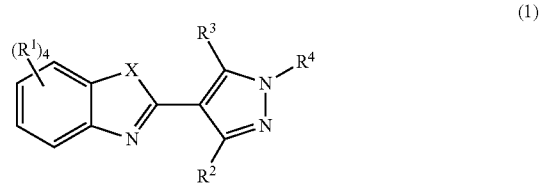

as a single tautomer, a mixture of tautomers, a single stereoisomer, a mixture of stereoisomers, or a racemic mixture; or a pharmaceutically acceptable salt or solvate thereof; wherein: $R^1$, $R^2$ and $R^3$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^4$ is selected from hydrogen, heteroalkyl, heteroaryl, and hydrocarbyl; X is selected from S, O and $NR^9$, and $R^9$ is selected from hydrogen, heteroalkyl, heteroaryl, and hydrocarbyl.

These compounds of the invention will be referred to herein as pyrazolylbenzothiazole compounds or derivatives or analogs, where these terms are used interchangeably. Technically, a benothiazole compound has X equal to S. However, when X is O or $NR^9$, then the compounds may be considered pyrazolylbenzothiazole analogs.

In another aspect, this invention is directed to certain compounds of formula (1). For example, compounds of formula (1) as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$, $R^9$ is selected from hydrogen, heteroalkyl, heteroaryl, and hydrocarbyl; $R^1$ and $R^2$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is heterocycle; and $R^4$ is selected from hydrogen, heteroalkyl, heteroaryl, and hydrocarbyl.

As another example, the invention provides compounds of formula (1) as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^2$ is amino; $R^3$ is selected from hydrocarbyl, —O-hydrocarbyl and —S-hydrocarbyl; and $R^4$ is selected from hydrogen, heteroalkyl, heteroaryl, and hydrocarbyl.

As another example, the present invention provides compounds of formula (1) as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ and $R^2$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is hydrogen; and $R^4$ is selected from hydrogen, heteroalkyl, heteroaryl, and hydrocarbyl.

As another example, the present invention provides compounds of formula (1) as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$, $R^2$ and $R^3$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido, with the proviso that $R^1$ is not hydrogen in at least one occurrence of $R^1$; and $R^4$ is selected from hydrogen, heteroalkyl, heteroaryl, and hydrocarbyl.

As another example, the present invention provides compounds of formula (1) as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ and $R^2$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is halogen-substituted hydrocarbyl; and $R^4$ is selected from hydrogen, heteroalkyl, heteroaryl, and hydrocarbyl.

In another aspect, the present invention provides compounds of formula (2)

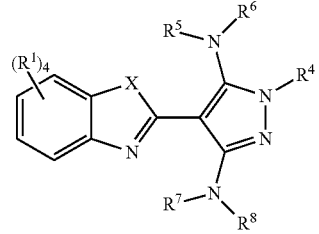

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^4$ is selected from hydrogen, heteroalkyl, heteroaryl, and hydrocarbyl; and $R^5$, $R^6$, $R^7$ and $R^8$ at each occurrence is independently selected from heteroalkyl, heteroaryl, hydrocarbyl and hydrogen, with the proviso that $R^7$ and $R^8$ may join together to form a heterocyclic ring including the nitrogen to which they are both bonded.

In related aspects, the present invention provides pharmaceutical compositions including compounds as set forth in an aspect as described above, in combination with a pharmaceutically acceptable excipient.

In another aspect, this invention is directed to the use of, and methods of using, the compounds of formula (1) as described above in the treatment of disorders associated with hyperproliferation and tissue remodelling or repair, inflammation, cell migration and invasion, and renal disease. The compounds are also useful in the inhibition of specific protein kinases, such as integrin-linked kinase.

In another aspect, the present invention provides compounds of formula (3):

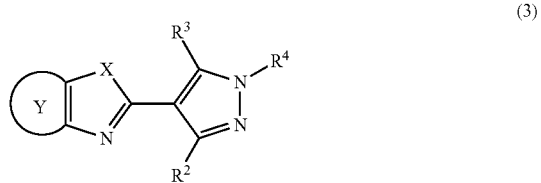

(3)

as a single tautomer, a mixture of tautomers, a single stereoisomer, a mixture of stereoisomers, or a racemic mixture; or a pharmaceutically acceptable salt or solvate thereof; wherein: $R^2$ and $R^3$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^4$ is selected from hydrogen, heteroalkyl, heteroaryl, and hydrocarbyl; X is selected from S, O and $NR^9$, and $R^9$ is selected from hydrogen, heteroalkyl, heteroaryl, and hydrocarbyl; Y is a 6 membered heterocycle having 1 or 2 nitrogen atoms and which is optionally further substituted by one or more groups selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido.

DETAILED DESCRIPTION OF EMBODIMENTS OF THE INVENTION

The present invention provides novel compounds, compositions and methods as set forth within this specification. In general, all technical and scientific terms used herein have the same meaning as commonly understood to one of ordinary skill in the art to which this invention belongs, unless clearly indicated otherwise. For clarification, listed below are definitions for certain terms used herein to describe the present invention. These definitions apply to the terms as they are used throughout this specification, unless otherwise clearly indicated.

DEFINITION OF TERMS

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art. As used in the specification and appended claims, unless specified to the contrary, the following terms have the meaning indicated:

"Alkyl" refers to a straight or branched monovalent hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, it is understood that for radicals, as defined below, that contain a substituted alkyl or alkenyl group that the substitution can occur on any carbon of the alkyl group.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like.

"Alkenyl" refers to a straight or branched monovalent hydrocarbon chain radical consisting solely of carbon and hydrogen atoms, containing at least one double bond, having from two to eight carbon atoms, and which is attached to the rest of the molecule by a single bond, e.g., ethenyl, prop-1-enyl, but-1-enyl, pent-1-enyl, penta-1,4-dienyl, and the like.

"Alkoxy" refers to a radical of the formula —$OR_a$ where $R_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of alkyl, alkoxy, hydroxy, halo, haloalkyl, haloalkoxy, amino and carboxy as defined herein.

"Aralkyl" refers to a radical of the formula —$R_aR_b$ where $R_a$ is an alkyl radical as defined above and $R_b$ is one or more aryl radicals as defined above, e.g., benzyl, diphenylmethyl, and the like. The aryl radical may be optionally substituted as described above.

"Aralkenyl" refers to a radical of the formula —$R_e$—$R_b$ where $R_b$ is an aryl radical as defined above and $R_e$ is an alkenyl radical as defined above, e.g., 2-phenylethenyl, and the like.

"Carboxy" refers to the —C(O)OH radical.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, alkoxy, halo, haloalkyl, haloalkoxy, hydroxy, amino, and carboxy.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —$OR_c$ where $R_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. The heterocyclyl radical may not be attached to the rest of the molecule at any heteroatom atom. Examples of such heterocyclyl radicals include, but are not limited to, azepinyl, acridinyl, benzimidazolyl, benzthiazolyl, benzoxazolyl, benzopyranyl, benzopyranonyl, benzofuranyl, benzofuranonyl, benzothienyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of hydroxy, halo, alkyl, alkoxy, haloalkyl, haloalkoxy, nitro, cyano, amino, and carboxy. Preferred heterocyclyl radicals for $R^5$ are those radicals selected from the group consisting of furanyl, isooxazolyl, pyridinyl, thienyl, pyrrolyl, quinolinyl, benzothienyl, benzodioxolyl, benzooxadiazolyl, pyrazole, thiadiazolyl, and quinoxalinyl;

"N-heterocyclyl" refers to a heterocyclyl radical as defined above wherein the one to five heteroatoms contained therein are selected only from nitrogen. Preferred N-heterocyclyl radicals for $R^2$ are those radicals selected from the group consisting of pyridinyl, thiazolyl, tetrazolyl, pyrazolyl, isoquinolinyl, quinolinyl, and phthalazinyl;

"Heterocyclylalkyl" refers to a radical of the formula —$R_aR_d$ where $R_a$ is an alkyl radical as defined above and $R_d$ is a heterocyclyl radical as defined above, and if the heterocyclyl is a nitrogen-containing heterocyclyl, the heterocyclyl may be attached to the alkyl radical at the nitrogen atom. A preferred heterocyclylalkyl radical for $R^3$ is morpholinylalkyl; preferred heterocyclylalkyl radicals for $R^5$ are those radicals selected from the group consisting of isoindoledionylalkyl, morpholinylalkyl, and triazolylalkyl.

"Heterocyclylcarbonyl" refers to a radical of the formula —C(O)—$R_d$ where $R_d$ is a heterocyclyl radical as defined above, and if the heterocyclyl is a nitrogen-containing heterocyclyl, the heterocyclyl may be attached to the carbonyl at the nitrogen atom. A preferred hetereocyclylcarbonyl radical for $R^3$ is pyridinylcarbonyl.

"Hydrocarbyl", sometimes abbreviated as "Hy", refers to a radical composed solely of carbon and hydrogen. The hydrocarbyl group may be saturated or unsaturated, and may independently have the carbons arranged in a linear, branched or cyclic fashion. In various optional embodiments of the invention, the hydrocarbyl moiety has 1-100, or 1-90, or 1-80, or 1-70, or 1-60, or 1-50, or 1-45, or 1-40, or 1-35, or 1-30, or 1-29, or 1-28, or 1-27, or 1-26, or 1-25, or 1-24, or 1-23, or 1-22, or 1-21, or 1-20, or 1-19, or 1-18, or 1-17, or 1-16, or 1-15, or 1-14, or 1-13, or 1-12, or 1-11, or 1-10, or 1-9, or 1-8, or 1-7, or 1-6, or 1-5, or 2-100, or 2-90, or 2-80, or 2-70, or 2-60, or 2-50, or 2-45, or 2-40, or 2-35, or 2-30, or 2-29, or 2-28, or 2-27, or 2-26, or 2-25, or 2-24, or 2-23, or 2-22, or 2-21, or 2-20, or 2-19, or 2-18, or 2-17, or 2-16, or 2-15, or 2-14, or 2-13, or 2-12, or 2-11, or 2-10, or 2-9, or 2-8, or 2-7, or 2-6, or 2-5, or 3-100, or 3-90, or 3-80, or 3-70, or 3-60, or 3-50, or 3-45, or 3-40, or 3-35, or 3-30, or 3-29, or 3-28, or 3-27, or 3-26, or 3-25, or 3-24, or 3-23, or 3-22, or 3-21, or 3-20, or 3-19, or 3-18, or 3-17, or 3-16, or 3-15, or 3-14, or 3-13, or 3-12, or 3-11, or 3-10, or 3-9, or 3-8, or 3-7, or 3-6, or 3-5 carbons. Independently, the hydrocarbyl moiety may be described as an alkyl, alkenyl, alkynyl, cycloalkyl, cycloalkylene, or aryl moiety, where alkyl, alkenyl and alkynyl is optionally substituted with one or more $Hy^1$ groups selected from cycloalkyl, cycloalkylene and aryl, where each $Hy^1$ group is optionally substituted with one or more $Hy^2$ groups selected from alkyl, alkenyl, alkynyl, cycloalkyl, cycloalkylene, and aryl; and cycloalkyl, cycloalkylene and aryl is optionally substituted with one or more $Hy^2$ groups, provided that when $Hy^2$ is selected from alkyl, alkenyl or alkynyl, then $Hy^2$ may be substituted with one or more $Hy^3$ groups selected from cycloalkyl, cycloalkylene and aryl, where each $Hy^3$ group is optionally substituted with one or more $Hy^4$ groups selected from alkyl, alkenyl, alkynyl, cycloalkyl, cycloalkylene, and aryl, and when $Hy^2$ is selected from cycloalkyl, cycloalkylene and aryl then $Hy^2$ is optionally substituted with one or more $Hy^4$ groups, and further provided that aryl includes an aryl ring fused to a non-aromatic hydrocarbocyclic ring. Halogen-substituted hydrocarbyl refers to a hydrocarbyl group wherein one or more of the hydrogens has been replaced with an equal number of halogens.

"Mammal" includes humans and domesticated animals, such as cats, dogs, swine, cattle, sheep, goats, horses, rabbits, and the like.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Pharmaceutically acceptable excipient" as used herein is intended to include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or stabilizer which has been approved by the United States Food and Drug Administration as being acceptable for use in humans or domestic animals.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam).

A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers that release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

Tautomers refer to various forms of a compound that differ only by the shifting of one or more double bonds and the concomitant shifting of hydrogen atoms. For example, when $R^4$ is hydrogen in the formula (1), then the two double bonds may shift to provide two tautomeric forms, as shown in formulae (1a) and (1b).

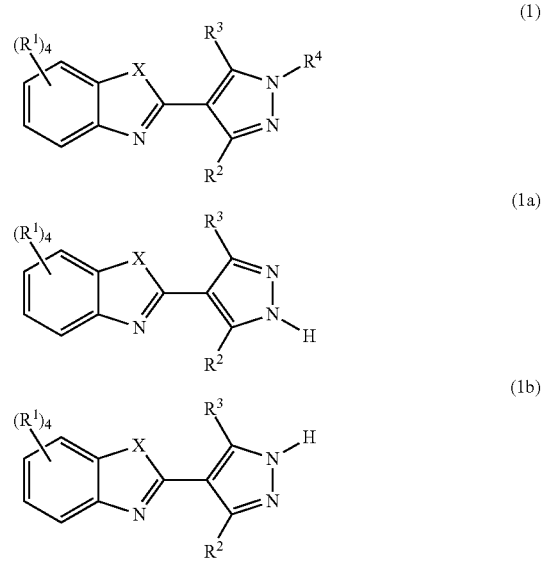

Another example of tautomerism arises when a substituent on the pyrazole ring is adjacent to a double bond and can have hydrogen substitution. A specific example is shown in formulae (1c) and (1d).

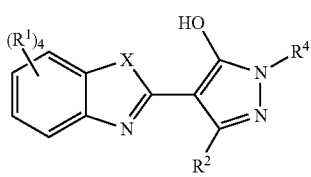

(1c)

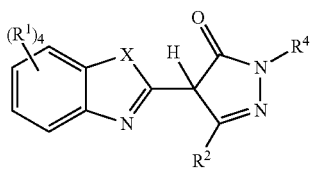

(1d)

"Therapeutically effective amount" refers to that amount of a compound of the invention, which, when administered to a mammal, particularly a human, in need thereof, is sufficient to effect treatment, as defined below, for hyperproliferative disorders. The amount of a compound of the invention which constitutes a "therapeutically effective amount" will vary depending on the compound, the hyperproliferative disorder and its severity, and the age of the mammal to be treated, but can be determined routinely by one of ordinary skill in the art having regard to his own knowledge and to this disclosure.

"Treating" or "treatment" as used herein covers the treatment of a hyperproliferative disorder in a mammal, preferably a human, and includes:

(i) preventing the disorder from occurring in a human, in particular, when such mammal is predisposed to the disorder but has not yet been diagnosed as having it;

(ii) inhibiting the disorder, i.e., arresting its development; or (iii) relieving the disorder, i.e., causing regression of the disorder.

The compounds of the invention, or their pharmaceutically acceptable salts, may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

Unless otherwise indicated by the nomenclature, compound names are intended to include any single tautomer, single stereoisomer, enantiomer, racemate or mixtures thereof.

Preferred Embodiments

As mentioned previously, in one aspect the present invention provides a pharmaceutical composition comprising a pharmaceutically acceptable excipient and a compound of formula (1):

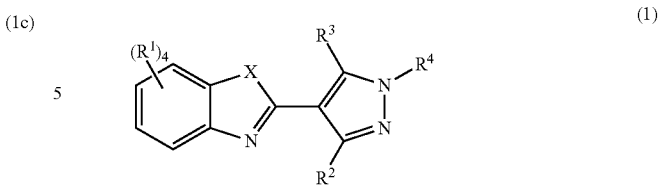

(1)

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$, $R^2$ and $R^3$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; and $R^4$ is selected from hydrogen, heteroalkyl, heteroaryl, and hydrocarbyl. In various optional embodiments of the present invention, the compositions containing a compound of formula (1) may be described as containing a compound of formula (1) wherein one or more of the following criteria are used to describe the compounds of formula (1), where any two or more of these criteria may be combined in describing a group of compounds of formula (1) that may be present in the pharmaceutical composition of the invention: heteroalkyl is one or more of the following: aminohydrocarboyl (i.e., —NH—C(═O)-Hy), amido (i.e., —C(═O)—$NH_2$), carboxylic acid (i.e., —COOH), cyano (i.e., —CN), dihydrocarbylamido (i.e., —C(═O)—N(Hy)(Hy)), dihydrocarbylamino (i.e., —N(Hy)(Hy)), di(hydrocarbyl)phosphido, formyl (i.e., —C(═O)H), hydrocarboyl (i.e., —C(═O)-Hy), hydrocarboyloxy (i.e., —O—C(═O)-Hy) hydrocarbylamino (i.e., —NH-Hy), hydrocarbyloxy (i.e., —O-Hy), hydrocarbyloxycarbonyl (i.e., —C(═O)—O-Hy) hydrocarbylsiloxy, hydrocarbylsilylamino, hydrocarbylsulfido (i.e., —S-Hy), hydrocarbylthio, hydrocarbylamido (i.e., —C(═O)—N(H)(Hy)), isothiocyanate, N-heterocycle, perfluorohydrcarbyl, thiocyanate, and hydrocarbyl substituted with one or more groups selected from alkylamino, amino, aminosulfinyl, aminosulfonyl, azido, dialkylamino, halogen, heteroalkyl, heteroaryl, hydrazinyl, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; hydrocarbyl is one or more of the following: alkyl, alkenyl, alkynyl, cycloalkyl, cycloalkylene, and aryl, where alkyl, alkenyl and alkynyl is optionally substituted with one or more $Hy^1$ groups selected from cycloalkyl, cycloalkylene and aryl, where each $Hy^1$ group is optionally substituted with one or more $Hy^2$ groups selected from alkyl, alkenyl, alkynyl, cycloalkyl, cycloalkylene, and aryl; and cycloalkyl, cycloalkylene and aryl is optionally substituted with one or more $Hy^2$ groups, provided that when $Hy^2$ is selected from alkyl, alkenyl or alkynyl, then $Hy^2$ may be substituted with one or more $Hy^3$ groups selected from cycloalkyl, cycloalkylene and aryl, where each $Hy^3$ group is optionally substituted with one or more $Hy^4$ groups selected from alkyl, alkenyl, alkynyl, cycloalkyl, cycloalkylene, and aryl, and when $Hy^2$ is selected from cycloalkyl, cycloalkylene and aryl then $Hy^2$ is optionally substituted with one or more $Hy^4$ groups, and further provided that aryl includes an aryl ring fused to a non-aromatic hydrocarbocyclic ring; $R^1$ at each occurrence is hydrogen; $R^4$ is hydrogen; $R^4$ is $C_1$-$C_8$ hydrocarbyl; $R^2$ is hydrogen; $R^2$ is selected from lower alkyl and lower haloalkyl; $R^2$ is amino; $R^2$ is heterocycle; $R^2$ is N-heterocycle; $R^2$ is hydrocarbyl; $R^3$ is hydrogen; $R^3$ is selected from phenyl and substituted phenyl; $R^3$ is phenyl substituted with one or more substituents selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is phenyl substituted with one or more substituents selected from hydroxyl, lower alkoxy, and lower alkyl; $R^3$ is heteroalkyl; $R^3$ is selected from amino, hydrocarbylamino and dihydrocarbylamino; $R^3$ is hydrocarbylamino where hydrocarbyl is aralkyl; $R^3$ is hydrocarbylamino where hydrocarbyl is alkyl; $R^3$ is amino; $R^3$ is hydrocarbyl. Optionally, one or more of the following compounds are excluded from the scope of compound useful in the pharmaceutical compositions of the present invention: 1H-pyrazole-3,5-diamine, 4-(2-benzothiazolyl); 1H-pyrazole-3,5-diamine, 4-(2-benzothiazolyl)-N-3-(4-methylphenyl); 1H-pyrazole-3,5-diamine, 4-(2-benzothiazolyl)-N-3-phenyl; and 3H-pyrazol-3-one, 4-(2-benzothiazolyl)-1,2-dihydro-5-(4-nitrophenyl).

The present invention also provides compounds that may be used in the methods disclosed herein. In one aspect, the present invention provides a compound of formula (1)

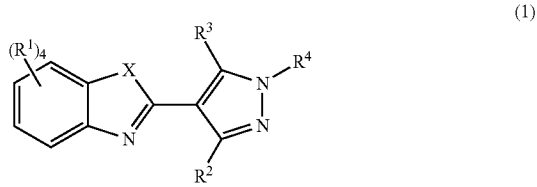

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ and $R^2$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is heterocycle; and $R^4$ is selected from hydrogen, heteroalkyl, heteroaryl, and hydrocarbyl. In various optional embodiments of this aspect of the present invention, one or more of the following criteria may be used to describe the compounds, where any two or more of the criteria may be combined in describing a group of compounds, however if two criteria are inconsistent then those inconsistent criteria may only be combined in the alternative: $R^1$ is hydrogen at each of 4 occurrences; $R^1$ is hydrogen at 3 out of 4 occurrences; $R^1$ is hydrogen at 2 out of 4 occurrences; $R^2$ is amino; $R^2$ is heteroalkyl; $R^2$ is heteroaryl; $R^2$ is hydrocarbyl; $R^2$ is hydrogen; $R^2$ is hydroxyl; $R^3$ is N-heterocycle, i.e., the heterocyclic ring at $R^3$ contains nitrogen as a ring atom, and this nitrogen atom is directly bonded to the pyrazole ring; $R^3$ contains 1-3 heteroatoms selected from O, S and N, and 1-5 carbon atoms; $R^4$ is hydrogen; $R^4$ is hydrocarbyl; $R^4$ is alkyl; $R^4$ is $C_1$-$C_8$ alkyl.

In another aspect, the present invention provides a compound of formula (1):

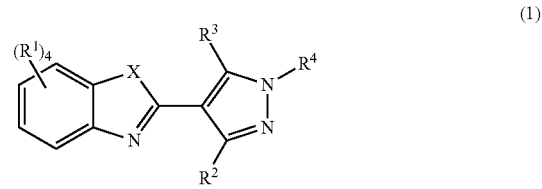

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^2$ is amino; $R^3$ is selected from hydrocarbyl, —O-hydrocarbyl and —S-hydrocarbyl; and $R^4$ is selected from hydrogen, heteroalkyl, heteroaryl, and hydrocarbyl. In various optional embodiments of this aspect of the present invention, one or more of the following criteria may be used to describe the compounds, where any two or more of the criteria may be combined in describing a group of compounds, however if two criteria are inconsistent then those inconsistent criteria may only be combined in the alternative: $R^1$ is hydrogen at each of 4 occurrences; $R^1$ is hydrogen at 3 out of 4 occurrences; $R^1$ is hydrogen at 2 out of 4 occurrences; $R^3$ is hydrocarbyl; $R^3$ is —O-hydrocarbyl; $R^3$ is —S-hydrocarbyl; the hydrocarbyl portion of $R^3$ is selected from one or more of the following, where any two or more of the following radicals may be combined in order to form a group from which the hydrocarbyl portion of $R^3$ is selected: alkyl, alkenyl, alkynyl, cycloalkyl, cycloalkylene, and aryl, where alkyl, alkenyl and alkynyl is optionally substituted with one or more $Hy^1$ groups selected from cycloalkyl, cycloalkylene and aryl, where each $Hy^1$ group is optionally substituted with one or more $Hy^2$ groups selected from alkyl, alkenyl, alkynyl, cycloalkyl, cycloalkylene, and aryl; and cycloalkyl, cycloalkylene and aryl is optionally substituted with one or more $Hy^2$ groups, provided that when $Hy^2$ is selected from alkyl, alkenyl or alkynyl, then $Hy^2$ may be substituted with one or more $Hy^3$ groups selected from cycloalkyl, cycloalkylene and aryl, where each $Hy^3$ group is optionally substituted with one or more $Hy^4$ groups selected from alkyl, alkenyl, alkynyl, cycloalkyl, cycloalkylene, and aryl, and when $Hy^2$ is selected from cycloalkyl, cycloalkylene and aryl then $Hy^2$ is optionally substituted with one or more $Hy^4$ groups, and further provided that aryl includes an aryl ring fused to a non-aromatic hydrocarbocyclic ring; $R^4$ is hydrogen; $R^4$ is heteroalkyl; $R^4$ is heteraryl; $R^4$ is hydrocarbyl; $R^4$ is alkyl; $R^4$ is $C_1$-$C_8$ alkyl. Optionally, in this aspect of the invention, the compounds of the invention exclude 1H-pyrazol-5-amine, 4-(2-benzothiazolyl)-1,3-diphenyl.

In another aspect, the present invention provides compounds of formula (1):

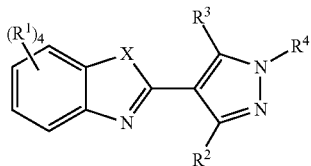

(1)

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ and $R^2$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is hydrogen; and $R^4$ is selected from hydrogen, heteroalkyl, heteroaryl, and hydrocarbyl. In various optional embodiments of this aspect of the present invention, one or more of the following criteria may be used to describe the compounds, where any two or more of the criteria may be combined in describing a group of compounds, however if two criteria are inconsistent then those inconsistent criteria may only be combined in the alternative: $R^1$ is hydrogen at each of 4 occurrences; $R^1$ is hydrogen at 3 out of 4 occurrences; $R^1$ is hydrogen at 2 out of 4 occurrences; $R^2$ is amino; $R^2$ is heteroalkyl; $R^2$ is phenyl; $R^2$ is substituted phenyl; $R^2$ is phenyl substituted with one or more substituents selected from any two or more of the following: amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^2$ is heteroaryl; $R^2$ is hydrocarbyl; $R^2$ is hydrogen; $R^2$ is hydroxyl; $R^4$ is hydrogen; $R^4$ is hydrocarbyl; $R^4$ is alkyl; $R^4$ is $C_1$-$C_8$ alkyl. Optionally, one or more of the following compounds are excluded from the scope of compounds within this aspect of the present invention: 3H-pyrazol-3-one, 4-(2-benzothiazolyl)-2,4-dihydro; 1,3-benzenediol, 4-[4-(2-benzothiazolyl)-1H-pyrazol-3-yl]; 1,3-benzenediol, 4-[4-(2-benzothiazolyl)-1H-pyrazol-3-yl]-6-ethyl-1-methanesulfonate; benzothiazole, 2-(1H-pyrazol-4-yl); phenol, 2-[4-(2-benzothiazolyl)-1H-pyrazol-3-yl]-5-methoxy-4-propyl; phenol, 2-[4-(2-benzothiazolyl)-1H-pyrazol-3-yl]5-[(4-nitrophenyl)methoxy]; 1H-pyrazol-3-amine, 4-(2-benzothiazolyl); 1,3-benzenediol, 4-[4-(2-benzothiazolyl)-1H-pyrazol-3-yl]-6-ethyl; 1H-pyrazol-5-amine, 4-(2-benzothiazolyl)-1-phenyl; and benzothiazole, 2-(1-phenyl-1H-pyrazol-4-yl).

In another aspect, the present invention provides a compound of formula (1):

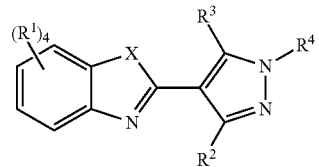

(1)

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ and $R^2$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is hydrocarbyl; and $R^4$ is selected from hydrogen, heteroalkyl, heteroaryl, and hydrocarbyl. In various optional embodiments of this aspect of the present invention, one or more of the following criteria may be used to describe the compounds, where any two or more of the criteria may be combined in describing a group of compounds, however if two criteria are inconsistent then those inconsistent criteria may only be combined in the alternative: $R^1$ is hydrogen at each of 4 occurrences; $R^1$ is hydrogen at 3 out of 4 occurrences; $R^1$ is hydrogen at 2 out of 4 occurrences; $R^2$ is hydrogen; $R^2$ is hydrocarbyl; $R^2$ is heteroalkyl; $R^2$ is hydroxyl; $R^2$ is heteroaryl; $R^2$ is amino; $R^2$ is phenyl; $R^2$ is substituted phenyl, where the substituents is selected from a group that consists of any two or more of the following: amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ (and, independently, $R^2$ when $R^2$ is hydrocarbyl) is selected from one or more of the following, where any two or more of the following radicals may be combined in order to form a group from which the hydrocarbyl is selected: alkyl, alkenyl, alkynyl, cycloalkyl, cycloalkylene, and aryl, where alkyl, alkenyl and alkynyl is optionally substituted with one or more $Hy^1$ groups selected from cycloalkyl, cycloalkylene and aryl, where each $Hy^1$ group is optionally substituted with one or more $Hy^2$ groups selected from alkyl, alkenyl, alkynyl, cycloalkyl, cycloalkylene, and aryl; and cycloalkyl, cycloalkylene and aryl is optionally substituted with one or more $Hy^2$ groups, provided that when $Hy^2$ is selected from alkyl, alkenyl or alkynyl, then $Hy^2$ may be substituted with one or more $Hy^3$ groups selected from cycloalkyl, cycloalkylene and aryl, where each $Hy^3$ group is optionally substituted with one or more $Hy^4$ groups selected from alkyl, alkenyl, alkynyl, cycloalkyl, cycloalkylene, and aryl, and when $Hy^2$ is selected from cycloalkyl, cycloalkylene and aryl then $Hy^2$ is optionally substituted with one or more $Hy^4$ groups, and further provided that aryl includes an aryl ring fused to a non-aromatic hydrocarbocyclic ring; $R^4$ is hydrogen; $R^4$ is heteroalkyl; $R^4$ is heteraryl; $R^4$ is hydrocarbyl; $R^4$ is alkyl; $R^4$ is $C_1$-$C_8$ alkyl. Optionally, one or more of the following compounds may be excluded from the scope of compounds within this aspect of the present invention: 1H-pyrazol-5-amine, 4-(2-benzothiazolyl)-1,3-diphenyl; 1,3-benzenediol, 4-[4-(2-benzothiazolyl)-5-methyl-1H-pyrazol-3-yl]-6-propyl; phenol, 2-[4-(2-benzothiazolyl)-5-methyl-1H-pyrazol-3-yl]-4-ethyl-5-methoxy; 1,3-benzenediol, 4-[4-(2-benzothiazolyl)-5-methyl-1H-pyrazol-3-yl]-2-methyl; benzothiazole, 2-(1,3-dimethyl-5-phenyl-1H-pyrazol-4-yl); 1,3-benzenediol, 4-[4-(2-benzothiazolyl)-5-methyl-1H-pyrazol-3-yl]-6-ethyl; 1,3-benzenediol, 4-[4-(2-benzothiazolyl)-5-methyl-1H-pyrazol-3-yl; 1,3-benzenediol, and 4-(4-(2-benzothiazolyl)-5-methyl-1H-pyrazol-3-yl]-6-ethyl-2[(1,3,3-trimethyl-6-azabicyclo[3.2.1]oct-6-yl)methyl.

In another aspect, the present invention provides compounds of formula (1)

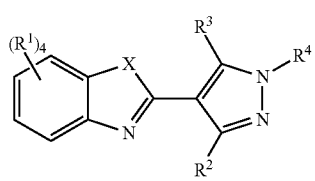

(1)

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$, $R^2$ and $R^3$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido, with the proviso that $R^1$ is not hydrogen in at least one occurrence of $R^1$; and $R^4$ is selected from hydrogen, heteroalkyl, heteroaryl, and hydrocarbyl. In various optional embodiments of this aspect of the present invention, the compounds of formula (1) may be described as meeting one or more of the following criteria, where any two or more of these criteria may be combined in describing a group of compounds of formula (1): heteroalkyl is one or more of the following: aminohydrocarboyl (i.e., —NH—C(=O)-Hy), amido (i.e., —C(=O)—NH$_2$), carboxylic acid (i.e., —COOH), cyano (i.e., —CN), dihydrocarbylamido (i.e., —C(=O)—N(Hy)(Hy)), dihydrocarbylamino (i.e., —N(Hy)(Hy)), di(hydrocarbyl)phosphido, formyl (i.e., —C(=O)H), hydrocarboyl (i.e., —C(=O)-Hy), hydrocarboyloxy (i.e., —O—C(=O)-Hy) hydrocarbylamino (i.e., —NH-Hy), hydrocarbyloxy (i.e., —O-Hy), hydrocarbyloxycarbonyl (i.e., —C(=O)—O-Hy) hydrocarbylsiloxy, hydrocarbylsilylamino, hydrocarbylsulfido (i.e., —S-Hy), hydrocarbylthio, hydrocarbylamido (i.e., —C(=O)—N(H)(Hy)), isothiocyanate, N-heterocycle, perfluorohydrcarbyl, thiocyanate, and hydrocarbyl substituted with one or more groups selected from alkylamino, amino, aminosulfinyl, aminosulfonyl, azido, dialkylamino, halogen, heteroalkyl, heteroaryl, hydrazinyl, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; hydrocarbyl is one or more of the following: $R^1$ is selected from amino, aminosulfinyl, aminosulfonyl, aryl, azido, halogen, heteroalkyl, heteroaryl, hydrazinyl, hydrocarbyl, hydrogen, hydroxyl, nitro, nitroso and thiol; in at least one occurrence, $R^1$ is amino, or $R^1$ is aminosulfinyl, or $R^1$ is aminosulfonyl, or $R^1$ is aryl, or $R^1$ is azido, or $R^1$ is halogen, or $R^1$ is heteroalkyl, or $R^1$ is heteroaryl, or $R^1$ is hydrazinyl, or $R^1$ is hydrocarbyl, or $R^1$ is hydrogen, or $R^1$ is hydroxyl, or $R^1$ is nitro, or $R^1$ is nitroso, or $R^1$ is thiol; $R^2$ is hydrogen; $R^2$ is selected from lower alkyl and lower haloalkyl; $R^2$ is amino; $R^2$ is heterocycle; $R^2$ is N-heterocycle; $R^2$ is hydrocarbyl; $R^3$ is hydrogen; $R^3$ is selected from phenyl and substituted phenyl; $R^3$ is phenyl substituted with one or more substituents selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is phenyl substituted with one or more substituents selected from hydroxyl, lower alkoxy, and lower alkyl; $R^3$ is heteroalkyl; $R^3$ is selected from amino, hydrocarbylamino and dihydrocarbylamino; $R^3$ is hydrocarbylamino where hydrocarbyl is aralkyl; $R^3$ is hydrocarbylamino where hydrocarbyl is alkyl; $R^3$ is amino; $R^3$ is hydrocarbyl; $R^4$ is hydrogen; and $R^4$ is $C_1$-$C_8$ hydrocarbyl.

In another aspect, the present invention provides compounds of formula (1)

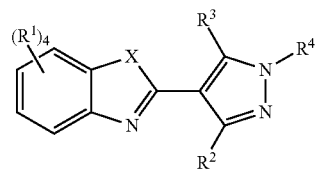

(1)

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ and $R^2$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^3$ is halogen-substituted hydrocarbyl; and $R^4$ is selected from hydrogen, heteroalkyl, heteroaryl, and hydrocarbyl. In optional embodiments of this aspect of the present invention, one or more of the following criteria may be used to describe the compounds, where any two or more of the following criteria may be combined: $R^1$ is hydrogen at each of 4 occurrences; $R^1$ is hydrogen at 3 out of 4 occurrences; $R^1$ is hydrogen at 2 out of 4 occurrences; $R^2$ is amino; $R^2$ is heteroalkyl; $R^2$ is phenyl; $R^2$ is substituted phenyl; $R^2$ is phenyl substituted with one or more substituents selected from any two or more of the following: amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^2$ is heteroaryl; $R^2$ is hydrocarbyl; $R^2$ is hydrogen; $R^2$ is hydroxyl; $R^2$ is trifluoromethyl; $R^3$ comprises 1 fluorine; $R^3$ comprises 2 fluorines, $R^3$ comprises 3 fluorines; $R^3$ is perfluorinated; $R^4$ is hydrogen; $R^4$ is hydrocarbyl; $R^4$ is alkyl; $R^4$ is $C_1$-$C_8$ alkyl.

In another aspect, the present invention provides compounds of formula (2)

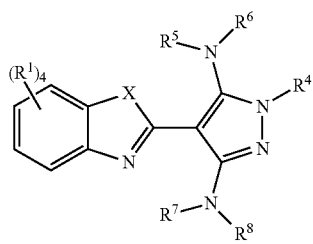

(2)

as a single tautomer, a mixture of tautomers, a single stereoisomer, a mixture of stereoisomers, or a racemic mixture; or a pharmaceutically acceptable salt or solvate thereof; wherein: X is selected from S, O and $NR^9$; $R^9$ is selected from hydrogen, heteroalkyl, heteroaryl, and hydrocarbyl; $R^1$ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfonyl, sulfoxido, thiol, thioureido, and ureido; $R^4$ is selected from hydrogen, heteroalkyl, heteroaryl, and hydrocarbyl; and $R^5$, $R^6$, $R^7$ and $R^8$ at each occurrence is independently selected from heteroalkyl, heteroaryl, hydrocarbyl and hydrogen, with the proviso that $R^7$ and $R^8$ may join together to form a heterocyclic ring including the nitrogen to which they are both bonded. In optional embodiments of the invention, one or more of the following criteria may be used to describe the compound in this aspect of the invention, where any two or more of these criteria may be combined: $R^1$ is hydrogen at each occurrence; $R^1$ excludes hydrogen at one occurrence; $R^1$ excludes hydrogen at two occurrences; $R^4$ is hydrogen; $R^4$ is hydrocarbyl; $R^4$ is $C_1$-$C_8$ hydrocarbyl; $R^4$ is alkyl; $R^4$ is $C_1$-$C_8$alkyl; $R^5$ is hydrogen; $R^6$ is hydrogen; $R^7$ is hydrogen; $R^8$ is hydrocarbyl; $R^8$ is heteroalkyl; and $R^8$ is heteroaryl. Optionally, one or more of the following compounds is excluded from the scope of this aspect of the present invention: 1H-pyrazole-3,5-diamine, 4-(2-benzothiazolyl); 1H-pyrazole-3,5-diamine, 4-(2-benzothiazolyl)-N3-(4-methylphenyl); and 1H-pyrazole-3,-5-diamine, 4-(2-benzothiazolyl)-N3-phenyl.

In each of the compounds and compositions and methods of the present invention, in one aspect, X is S (i.e., the compound is a benzothiazole compound). In each of the compounds, compositions and methods of the present invention, in one aspect, X is O (i.e., the compound is a benzooxozole compound). In each of the compounds, compositions and methods of the present invention, in one aspect X is $NR^9$ (i.e., the compound is a benzoimidazole compound) where $R^9$ is selected from hydrogen, heteroalkyl, heteroaryl, and hydrocarbyl, and in various optional embodiments of this aspect of the invention, $R^9$ is hydrogen, or $R^9$ is hydrocarbyl, or $R^9$ is heteroalkyl, or $R^9$ is heteroaryl, e.g., X may be —N(H)—.

Preparation of the Compounds of the Invention

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of formula (1), as described above in the Summary of the Invention, may not possess pharmacological activity as such, they may be administered to a mammal with cancer or inflammation and thereafter metabolized in the body to form compounds of the invention which are pharmacologically active. Such derivatives may therefore be described as "prodrugs". All prodrugs of compounds of formula (I) are included within the scope of the invention.

The following Reaction Schemes illustrate methods to make compounds of formula (1). It is understood that one of ordinary skill in the art would be able to make the compounds of formula (1) by similar methods or by methods known to one skilled in the art. In general, starting components may be obtained from sources such as Aldrich, or synthesized according to sources known to those of ordinary skill in the art (see, e.g., Smith and March, *March's Advanced Organic Chemistry: Reactions, Mechanisms, and Structure,* 5th edition (Wiley Interscience, New York)). Moreover, groups $R^1$ through $R^5$ are selected from components as indicated in the specification heretofore, and may be attached to starting components, intermediate components, and/or final products according to schemes known to those of ordinary skill in the art. In the following Reaction Schemes, $R^1$, $R^2$, $R^3$, $R^4$ and $R^5$ are as defined above in the Summary of the Invention and R represents either hydrogen or a lower alkyl group.

Compounds as set forth in compositions and methods of the present invention may be prepared by methods disclosed in the literature, and/or as summarized in the following schemes:

Reaction Scheme 1

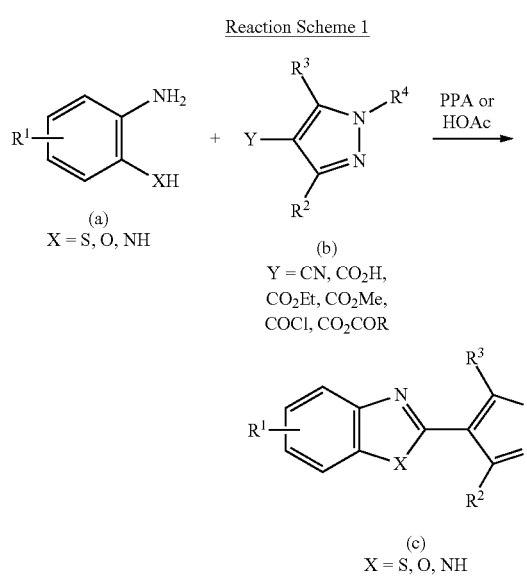

(a) X = S, O, NH (b) Y = CN, CO$_2$H, CO$_2$Et, CO$_2$Me, COCl, CO$_2$COR (c) X = S, O, NH

In general, compounds of formula (c) (2-(1H-pyrazol-4-yl)benzothiazoles (X=S), benzoxazoles (X=O), benzimidazoles (X=NH)) can be prepared via the reaction of a substituted 2-aminobenzenethiol, or a 2-aminophenol, or a 1,2-phenyldiamine with a substituted 1H-pyrazole-4-carboxylic acid or a carboxylic acid derivative in an acid such as acetic acid or polyphosphoric acid at elevated temperature similar to the procedure described in the literature (Shi, D.-F.; Bradshaw, T. D.; Wrigley, S. et al. *J. Med. Chem.* (1996), 39, 3375). The solution is diluted with water and neutralized with an ammonia solution. The product is isolated by filtration or by extraction and, if necessary, is purified by flash chromatography or preparative TLC.

Alternatively, the compounds of this invention can be prepared as described in Reaction Scheme 2.

Reaction Scheme 2

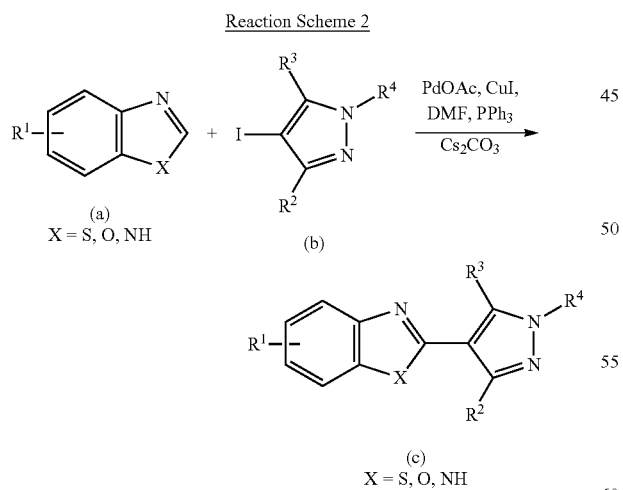

(a) X = S, O, NH (b)

(c) X = S, O, NH

In general, compounds of formula (c) ((2-(1H-pyrazol-4-yl)benzothiazoles (X=S), (2-(1H-pyrazol-4-yl)benzoxazoles (X=O), and (2-(1H-pyrazol-4-yl)benzimidazoles (X=NH)) can be prepared by coupling of a compound of formula (a) with a substituted 4-iodopyrazole of formula (b) in a solvent such as DMF and in the presence of a transition metal catalyst, such as palladium acetate and copper iodide, and triphenylphosphine and a base such as Cs$_2$CO$_3$ as described in the literature (Pivsa-Art, S.; Satoh, T.; Kawamura, Y. *Bull. Chem. Soc. Jpn.*, (1998) 71, 467).

Alternatively, the compounds of this invention can be prepared as described in Reaction Scheme 3.

Reaction Scheme 3

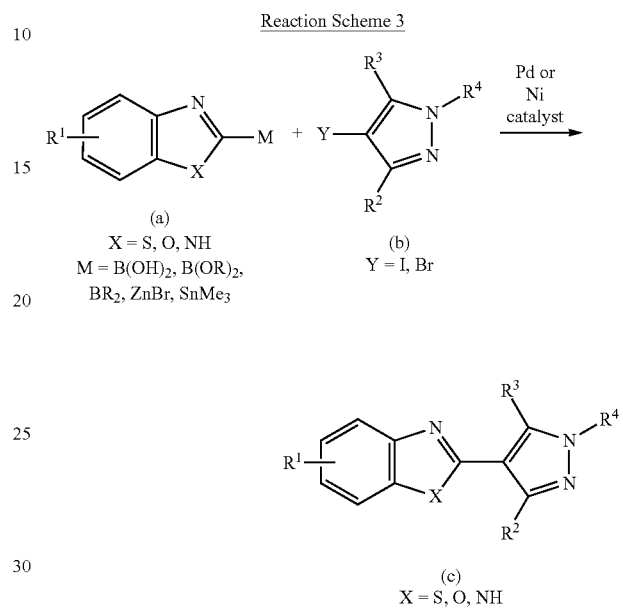

(a) X = S, O, NH M = B(OH)$_2$, B(OR)$_2$, BR$_2$, ZnBr, SnMe$_3$ (b) Y = I, Br (c) X = S, O, NH

In general, compounds of formula (c) ((2-(1H-pyrazol-4-yl)benzothiazoles (X=S), (2-(1H-pyrazol-4-yl)benzoxazoles (X=O), and (2-(1H-pyrazol-4-yl)benzimidazoles (X=NH)) can be prepared through the coupling of a metallated compound of formula (a) with a substituted 4-halopyrazole of formula (b) in the presence of a transition metal catalyst such as palladium, nickel, or others. The metallated compound of formula (a) may be prepared by the usual routes known to those skilled in the art, such as by metallation using an organometallic reagent, or by metal halogen exchange, or by transmetallation. The metal element can be boron, zinc, tin, magnesium, lithium or others.

Alternatively, the compounds of this invention can be prepared as described in Reaction Scheme 4.

Reaction Scheme 4

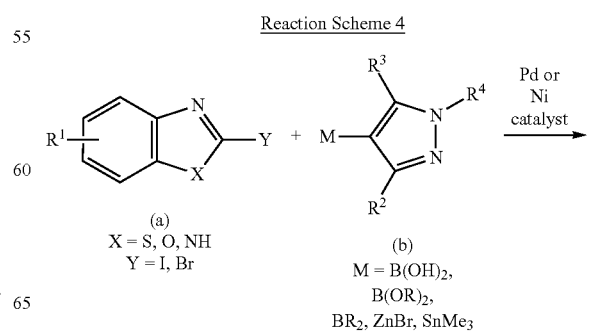

(a) X = S, O, NH Y = I, Br (b) M = B(OH)$_2$, B(OR)$_2$, BR$_2$, ZnBr, SnMe$_3$

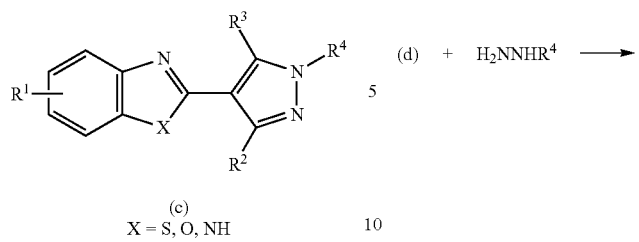

(c)
X = S, O, NH

In general, compounds of formula (c) ((2-(1H-pyrazol-4-yl)benzothiazoles (X=S), (2-(1H-pyrazol-4-yl)benzoxazoles (X=O), and (2-(1H-pyrazol-4-yl)benzimidazoles (X=NH)) can be prepared through the coupling of a metallated compound of formula (b) with a substituted 2-halobenzothiazole in the presence of a transition metal catalyst such as palladium, nickel, or others. The metallated compound of formula (a) may be prepared by the usual routes known to those skilled in the art, such as by metallation using an organometallic reagent, or by metal halogen exchange, or by transmetallation. The metal element can be boron, zinc, tin, magnesium, lithium or others.

Alternatively, the compounds of this invention can be prepared as described in Reaction Scheme 5.

Reaction Scheme 5

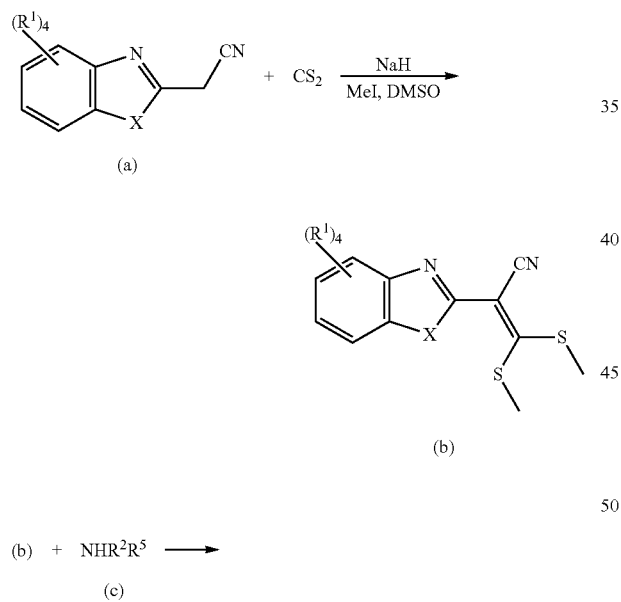

In general, compounds of formula (b) are prepared from substituted acetonitriles of formula (a) reacting with carbon disulfide in the presence of a base, such as sodium hydride, and an alkylating agent, such as methyl iodide as described in the literature (Augustin, M.; Doelling, W.; *J. Prakt. Chem.* (1982) 1, 3). The obtained compounds of formula (b) can then be substituted with a nucleophile of formula (c) as described in the literature (Augustin, M.; Doelling, W. supra;) to afford compounds of formula (d). Compounds of formula (d) can then react with hydrazine or a substituted hydrazine in a solvent such as ethanol, THF or dioxane to afford compounds of formula (e) in a similar way as described in literature (Fadda, A. A.; Amer, F. A.; Zaki, M. E. A.; Samir, K. H.; *Phosphorus, Sulfur Silicon Relat. Elem.* (1999), 155, 59). The compounds can be purified by recrystallization or flash chromatography and can be isolated as free bases or as salts.

Compounds of formula (a) can be prepared according to one of the methods shown in Reaction Scheme 6.

Reaction Scheme 6

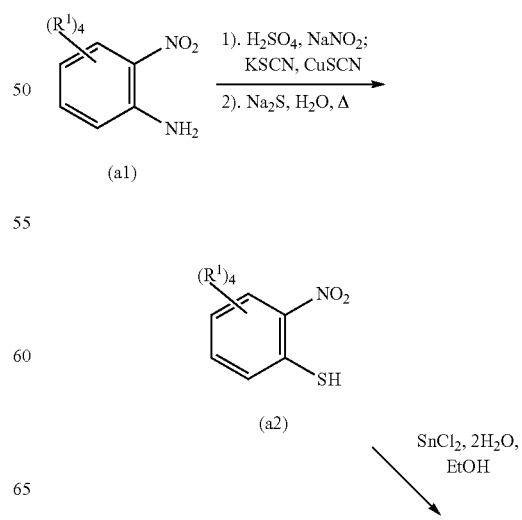

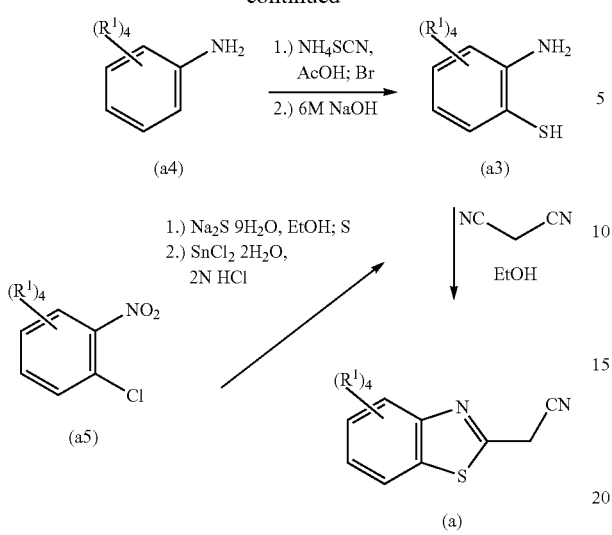

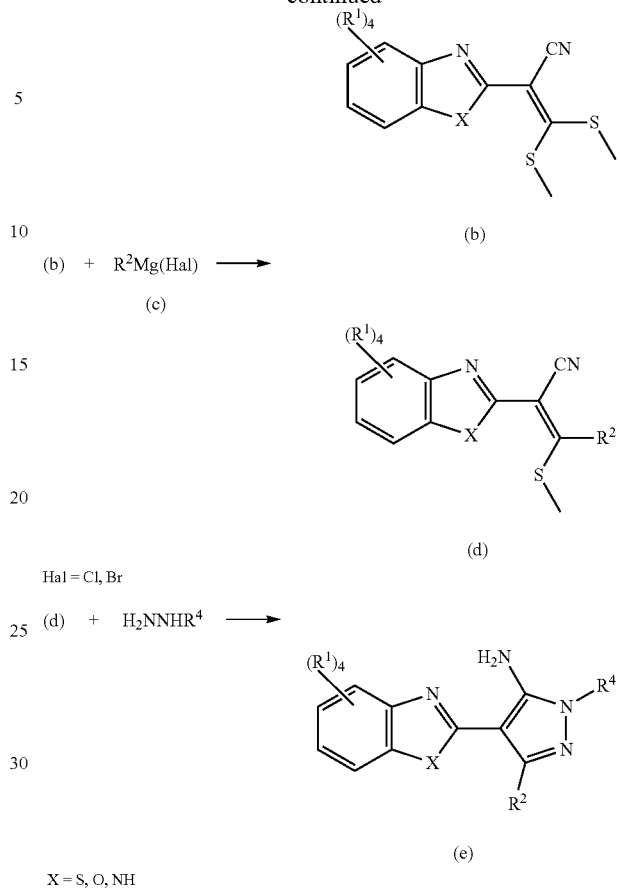

Hal = Cl, Br

A 2-nitroaniline of formula (a1) can be diazotized and then be reacted with potassium thiocyanate and cuprous thiocyanate. The resulting product can be reduced in the presence of sodium sulfide to give a compound of formula (a2). The resulting substituted nitrobenzene of formula (a2) can be reduced in the presence of tin (II) chloride dihydrate by refluxing the material in a suitable solvent such as ethanol to afford a compound of formula (a3). Alternatively, a compound of formula (a3) can be prepared by reacting a substituted aniline of formula (a4) with ammonium thiocyanate in acetic acid followed by the addition of bromine. The resulting product can be hydrolyzed by the use of a suitable source of hydroxide such as a 6M solution of sodium hydroxide. A compound of formula (a3) can also be produced by the reaction of a substituted 2-chloronitrobenzene of formula (a5) and a solution of sodium disulphide which is generated by dissolving sodium sulfide nonahydrate in hot ethanol followed by the addition of sulfur. This reaction generates a disulfide which can be reduced by refluxing the intermediate in the presence of tin (II) chloride dihydrate and 2N hydrochloric acid to produce a compound of formula (a3).

The compound of formula (a) can then be prepared by treating a compound of formula (a3) with malononitrile in refluxing ethanol. The product can be isolated by filtration and purified by recrystallization or flash chromatography.

Alternatively, the compounds of this invention can be prepared as described in Reaction Scheme 7.

X = S, O, NH

In general, compounds of formula (b) are prepared from substituted acetonitiles of formula (a) reacting with carbon disulfide in the presence of a base, such as sodium hydride, and an alkylating agent, such as methyl iodide as described in the literature (Augustin, M.; Doelling, W.; supra). The obtained compounds of formula (b) can then be substituted with a Gringard reagent of formula (c) or with an organolithium compound to afford compounds of formula (d). Compounds of formula (d) can then react with hydrazine or a substituted hydrazine in a solvent such as ethanol, THF or dioxane to afford compounds of formula (e) in a similar way as described in literature (Fadda, A. A.; Amer, F. A.; Zaki, M. E. A.; Samir, K. H.; *Phosphorus, Sulfur Silicon Relat. Elem.* (1999), 155, 59). The compounds can be purified by recrystallization or flash chromatography and can be isolated as free bases or as salts.

Alternatively, the compounds of this invention can be prepared as described in Reaction Scheme 8.

Reaction Scheme 7

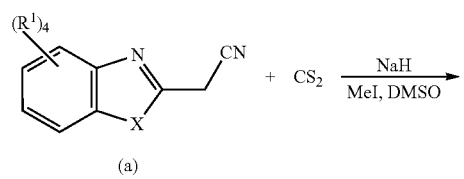

Reaction Scheme 8

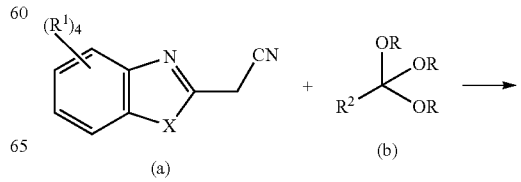

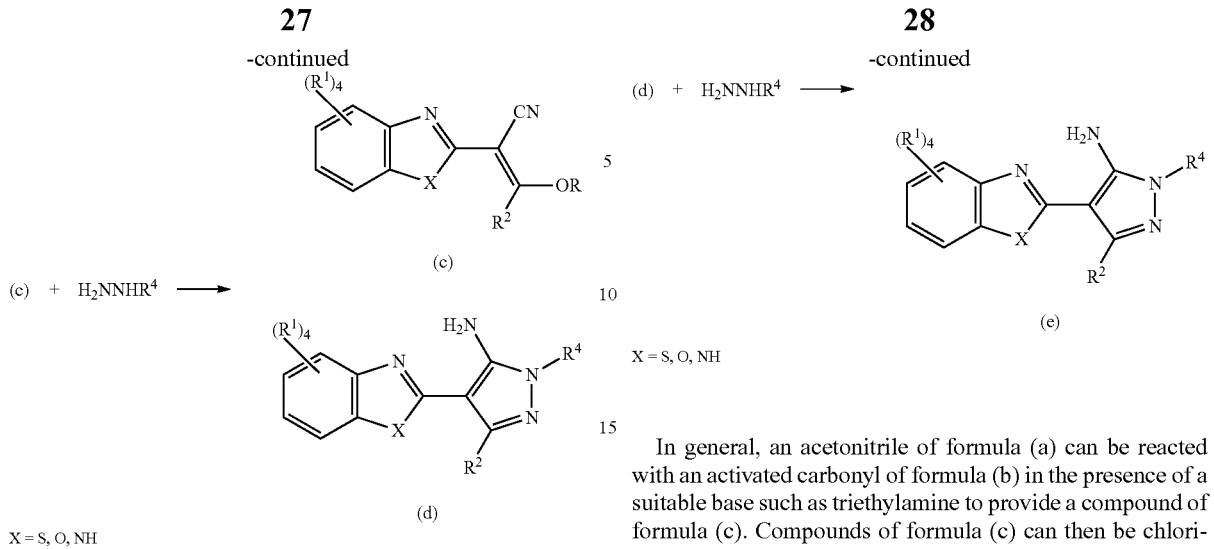

In general, compounds of formula (c) can be prepared from substituted acetonitriles of formula (a) via the reaction with substituted orthoester of formula (b) in a media such as acetic anhydride as described in the literature (Bontems, R. J.; Anderson, J. D.; Smee, D. F.; Jin, A.; Alaghamandan, H. A. *J. Med. Chem.* (1990), 8, 2174). Compounds of formula (c) can then be reacted with hydrazine or a substituted hydrazine in a solvent such as ethanol, THF or dioxane to afford compounds of formula (d). The products can be purified by recrystallization or flash chromatography and may be isolated as a free base or as a salt.

Alternatively, the compounds of this invention can be prepared as described in Reaction Scheme 9.

In general, an acetonitrile of formula (a) can be reacted with an activated carbonyl of formula (b) in the presence of a suitable base such as triethylamine to provide a compound of formula (c). Compounds of formula (c) can then be chlorinated to give compounds of formula (d) by reacting the material in neat phosphorous oxychloride at 100° C. Additionally, compounds of formula (d) can be produced by the reaction of compounds of formula (c) with triphenylphosphine, either neat or bound to a resin, and carbon tetrachloride in the presence of a suitable base such as triethylamine. Compounds of formula (e) can then be prepared from compounds of formula (d) by the reaction with hydrazine or a substituted hydrazine in a solvent such as ethanol, THF or dioxane.

Alternatively, the compounds of this invention can be prepared as described in Reaction Scheme 10.

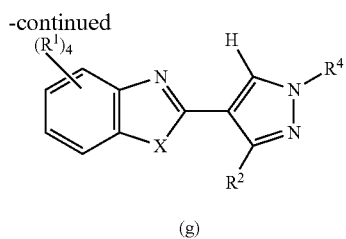

X = S, O, NH

In general, compounds of formula (c) can be prepared by reacting the appropriate compound of formula (a) with a base such as n-BuLi and treating the resulting anion with an ester of formula (b) in a suitable aprotic solvent such as THF (Fogagnolo, M.; Giovannini, P. P.; Guerrini, A.; Medici, A.; Pedrini, P.; Colombi, N. *Tetrahedron Asymmetry*, (1998) 9, 2317). The resulting intermediate was condensed with DMF dimethyl acetal and hydrazine, as its hydrate or acid salt, or an appropriately substituted hydrazine in a solvent such as ethanol, THF or dioxane to produce the desired product (as described for the preparation of 4-Benzothiazol-2-yl-2H-pyrazol-3-ylamine in Dawood, K. M.; Kandeel, Z. E.; Farag, A. M. *J. Chem. Res. Synop.* (1998), 4, 208).

Preparation of specific compounds of the invention is described in more detail below in the Examples.

Pharmaceutical Formulations

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intrathecal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well tolerated by the host. The implant containing the inhibitory compounds is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided inhibitory compounds and other cytotoxic agents has the advantages that the required dosages for the individual drugs is lower, and the effect of the different drugs complementary. Depending on the patient and condition being treated and on the administration route, the subject inhibitory compounds may be administered in dosages of 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with other pharmaceutically active agents, particularly other anti-metastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cis-platinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

Methods of Use

The subject compounds are administered to a subject having a hyperproliferative disorders, e.g. to inhibit tumor growth, to inhibit angiogenesis, to decrease inflammation associated with a lymphoproliferative disorder, to inhibit graft rejection, or neurological damage due to tissue repair, etc. The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g., to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one h and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the cell burden, and may be continued until there are essentially none of the undesirable cells detected in the body.

The compounds also find use in the specific inhibition of signaling pathway mediated by protein kinases. Protein kinases are involved in signaling pathways for such important cellular activities as responses to extracellular signals and cell cycle checkpoints. Inhibition of specific protein kinases provides a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in signaling mediated by protein kinases. Such conditions include those associated with defects in cell cycle regulation or in response to extracellular signals, e.g. hyperglycemia and diabetes Type I and Type II, immunological disorders, e.g. autoimmune and immunodeficiency diseases; hyperproliferative disorders, which may include psoriasis, arthritis, inflammation, angiogenesis, endometriosis, scarring, cancer, etc.

The compounds of the present invention are active in inhibiting purified kinase proteins, i.e. there is a decrease in the phosphorylation of a specific substrate in the presence of the compound. A protein kinase of particular interest in integrin linked kinase (ILK). ILK is a serine threonine kinase. The DNA and predicted amino acid sequence may be accessed at Genbank, no. U40282, or as published in Hannigan et al. Nature (1996) 379:91-96. ILK regulates integrin extracellular activity (ECM interactions) from inside the cell via its direct interaction with the integrin subunit. Interfering with ILK activity allows the specific targeting of integrin function, while leaving other essential signaling pathways intact. Increased levels of cellular ILK activity short circuits the normal requirement for adhesion to extracellular membrane in regulating cell growth. Thus, inhibiting ILK activity may inhibit anchorage-independent cell growth.

It is also known that many cell types undergo apoptosis if the appropriate contacts with extracellular matrix proteins are not maintained (anoikis). The induction of apoptosis by the subject compounds in such cells predicts an association with the ILK signaling pathway.

The compounds of the present invention bind to protein kinases at a high affinity, and find use as affinity reagents for the isolation and/or purification of such kinases. Affinity chromatography is used as a method of separating and purifying protein kinases and phosphatases using the biochemical affinity of the enzyme for inhibitors that act on it. The compounds are coupled to a matrix or gel. Preferably a microsphere or matrix is used as the support. Such supports are known in the art and commercially available. The inhibitor-coupled support is used to separate an enzyme that binds to the inhibitor from a complex mixture, e.g. a cell lysate, that may optionally be partially purified. The sample mixture is contacted with the inhibitor coupled support under conditions that minimize non-specific binding. Methods known in the art include columns, gels, capillaries, etc. The unbound compounds are washed free of the resin, and the bound proteins are then eluted in a suitable buffer.

The compounds of the invention may also be useful as reagents for studying signal transduction or any of the clinical disorders listed throughout this application.

Hyper-Proliferative Disorders of Interest

There are many disorders associated with a dysregulation of cellular proliferation. The conditions of interest include, but are not limited to, the following conditions.

The subject methods are applied to the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g. uterine, testicular and ovarian carcinomas, endometriosis, squamous and glandular epithelial carcinomas of the cervix, etc. are reduced in cell number by administration of the subject compounds Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature. Angiogenesis may be inhibited by affecting the cellular ability to interact with the extracellular environment and to migrate, which is an integrin-specific function, or by regulating apoptosis of the endothelial cells. Integrins function in cell-to-cell and cell-to-extracellular matrix (ECM) adhesive interactions and transduce signals from the ECM to the cell interior and vice versa. Since these properties implicate integrin involvement in cell migration, invasion, intra- and extravasation, and platelet interaction, a role for integrins in tumor growth and metastasis is obvious.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include breast cancers, which are primarily adenocarcinoma subtypes. Ductal carcinoma in situ (DCIS) is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

In one aspect of the invention, the pyrazolylbenzothiazole compounds disclosed herein may be used to inhibit integrin-linked kinase (ILK) for the treatment of inflammatory diseases and autoimmune conditions such as psoriasis in which the immune system directly contributes to disease pathogenesis. Integrin-linked kinase (ILK) is a 59 kDa serine/threonine kinase that associates with the cytoplasmic tail portions of $\beta 1$ and $\beta 3$ integrins, molecules that mediate adhesion of different cells to other cells or various components of the extracellular matrix. Furthermore, ILK associates with and interacts with a number of intracellular proteins. The enzymatic activity of ILK is modulated by the interaction of ILK-expressing cells with the extracellular matrix (ECM) component fibronectin, integrin clustering as well as a variety of growth factors. ILK activity is associated with a number of downstream signaling events. Upon adhesion to ECM, integrins and a selective group of cytoskeletal and signaling proteins are recruited to cell matrix contact sites where they serve to link the actin cytoskeleton to the ECM. These links function to mediate communication between the intracellular and extracellular compartments.

Thus, in one aspect the present invention relates to therapeutic compositions and methods for the treatment of inflammatory disorders including autoimmune diseases using compounds that inhibit ILK activity. Such disorders and diseases include, but are not limited to, psoriasis, rheumatoid arthritis, multiple sclerosis, scleroderma, systemic lupus erythematosus, Sjögren's syndrome, atopic dermatitis, asthma, and allergy. Target cells susceptible to the treatment include cells involved in instigating autoimmune reactions as well as those suffering or responding from the effects of autoimmune attack or inflammatory events.

As mentioned above, pyrazolylbenzothiazole compounds that function as ILK inhibitors may be formulated into a variety of compositions. Suitable excipients for use with ILK inhibitors include water, saline, dextrose, glycerol, Cremaphor™, ethanol and the like. These compositions may comprise further components such as conventional delivery agents and excipients including isotonising agents, pH regulators, solvents, solubilizers, dyes, gelling agents, thickeners, buffers and combinations thereof. To ameliorate inflammatory/autoimmune diseases such as psoriasis, inhibitors of ILK are administered by an appropriate means including, but not limited to, oral, intravenous, subcutaneous, intramuscular or topical routes. The local delivery, such as topical, of an ILK inhibitor provides high concentrations at the treatment site while lowering the likelihood of unwanted non-specific or other undesirable effects that might be associated with systemic delivery of such compounds. For the local delivery of pyrazolylbenzothiazole compounds for psoriasis and other cutaneous inflammatory or autoimmune conditions, the compounds may be administered in excipients containing concentrations of about 0.01 to about 10 mg/ml directly applied to the skin. If systemic delivery is required, a dose range of 0.1 mg/kg to 100 mg/kg body weight, preferably less than 10 mg/kg, is administered. The pyrazolylbenzothiazole compound may be given up to 3 times daily. Oral delivery may be given in tablets, capsules, liquid suspensions or solutions.

Although psoriasis is not life threatening, the social stigma and reduction in quality of life associated with disease are profound issues for these patients and their families. Established anti-psoriasis therapies have been grouped into suppressive and remittive types. Suppressive therapies (e.g. cyclosporine, topical calcitriol, methotrexate, retinoids), produce plaque clearance although these medications are not associated with a complete normalization of skin pharmacodynamic markers or large reductions in plaque T cell numbers. Phototherapy with ultraviolet (UV) B (280-320 nm) light alone or in combination with coal tar derivatives and photochemotherapy with 8-methoxypsoralen combined with UVA (320-400 nm) light (PUVA) are classified as remittive-type anti-psoriasis therapies. UVB light and PUVA are typically delivered in multiple treatment sessions, often several times weekly, until plaque clearance is achieved. The present invention provides pyrazolylbenzothiazole compounds that may be administered in combination with established anti-psoriasis therapies.

Renal Disorders

In one aspect of the invention, the pyrazolylbenzothiazole compounds disclosed herein may be used to modulate integrin-linked kinase (ILK) for the treatment of renal diseases. Thus, the present invention provides therapeutic compositions and methods for treating renal disease, and specifically provides therapeutic compositions and methods directed to modulating, and especially inhibiting, the activity of ILK so as to ameliorate glomerular renal disease states which may result in proteinuria, or states characterized by tubular or tubulo-interstitial damage. Preferred pyrazolylbenzothiazole compounds may be identified by screening for biological activity in an ILK-based functional assay, e.g. in vitro or in vivo ILK kinase activity.

According to current therapies, chronic progression of renal disease can be slowed for 6-12 months using angiotensin-converting enzyme (ACE) inhibitors, but there is no other satisfactory treatment at this time besides dialysis and ultimately transplantation of the organ. According to the present invention, pyrazolylbenzothiazole compounds may be administered at an appropriate time, before, concurrent or after, in relation to a second therapy for treating renal disorder, where that second therapy includes, but is not limited to, administration of an ACE inhibitor, or a pharmaceutically acceptable salt thereof, and a pharmaceutically acceptable carrier to a mammal in need thereof. Ace inhibitors include, but are not limited to, captopril, benazepril, enalapril, fosinopril, lisinopril, quinapril, ramipril, imidapril, perindopril, erbumine, and trandolapril. ACE Receptor Blockers may also be used in place of, or as well as, ACE inhibitors, and these include losartan, irbesartan, candesartan, cilexetil, and valsartan.

Thus, in one aspect, the present invention provides a method for treating a patient with renal dysfunction comprising administering to the patient an effective amount of a pyrazolylbenzothiazole compound or composition including a pyrazolylbenzothiazole compound as disclosed herein. In various embodiments, the compound is administered orally, or the compound is administered intravenously, or the compound is administered intraperitoneally. The compound may be administered intralumenally in or around the kidney. The patient may also be treated with an ACE inhibitor.

In one aspect, the present invention provides a method for lowering the protein levels in urine, comprising administering to that patient an effective amount of a pyrazolylbenzothiazole compound, or composition containing an pyrazolylbenzothiazole compound as disclosed herein. In various embodiments, the compound is administered orally, or intravenously, or intraperitoneally. The compound may be administered intralumenally in or around the kidney. The patient may also be treated with an ACE inhibitor.

Eye Disorders

In one aspect, the present invention relates to the use of pyrazolylbenzothiazoles as disclosed herein in the treatment of various eye diseases with underlining pathology of neovascularization of cornea, iris, retina or choroids. The subject methods are used for prophylactic or therapeutic purposes to treat ocular diseases to prevent, reduce or reverse the loss of visual acuity as well as loss of vision secondary to neovascularization of cornea, iris, retina or choroid. The term "treating" is used to refer to both prevention of disease, and treatment of pre-existing conditions. While treatment during early stages is desirable, the adverse symptoms of the disease may be at least partially alleviated by treatment during later stages In one aspect, pyrazolylbenzothiazole compounds that modulate the activity of integrin linked kinase (ILK) are administered systemically or locally to treat ophthalmic diseases with an underlining pathology that is characteristic of ocular neovascularization. Such a treatment is used alone as single therapy or in combination with a second therapy as an adjunct to prevent, to reduce or to reverse the loss of visual acuity as well as loss of vision secondary to neovascularization of cornea, iris, retina or choroids.

For example, in one aspect the invention is directed to a method to prevent, to reduce or to reverse ocular neovascularization in an eye of an animal having a neovascular lesion, comprising the steps of identifying said lesion in the eye of the animal, administering to the animal an amount of a pyrazolylbenzothiazole compound as disclosed herein sufficient to allow said compound to localize in said lesion. Methods utilizing local administration that provides for a prolonged localized concentration, which may utilize sustained release implants, viscous solutions, or other topical formulation, are of particular interest. A pyrazolylbenzothiazole compound can be administered alone as single therapy, or in combination with a second therapy, for example at an appropriate time, before, concurrent or after, in relation to a second therapy including but not limited to Visudyne™ therapy, photocoagulation or transpupillary thermotherapy as an adjunct treatment for ocular neovascularization.

Some examples of ocular disorders that may be treated by various embodiments of the present invention include, without limitation: retinal diseases (diabetic retinopathy, chronic glaucoma, retinal detachment, sickle cell retinopathy, age related macular degeneration (AMD) due to subretinal neovascularization); rubeosis iritis; inflammatory diseases; chronic uveitis; neoplasms (retinoblastoma, pseudoglioma); Fuchs' heterochromic iridocyclitis; neovascular glaucoma; corneal neovascularization (inflammatory, transplantation, developmental hypoplasia of the iris); neovascularization resulting following a combined vitrectomy and lensectomy; vascular diseases (retinal ischemia, choroidal vascular insufficiency, choroidal thrombosis, carotid artery ischemia); neovascularization of the optic nerve; and neovascularization due to penetration of the eye or contusive ocular injury.

In practicing the method of treatment or use of a pyrazolylbenzothiazole compound in an ophthalmic diseases with an underlining pathology that is characteristic of ocular neovascularization, a therapeutically effective amount of a pyrazolylbenzothiazole compound is administered to a subject afflicted with a disease or disorder related to neovascularization, or to a tissue that has been neovascularized. The inhibitor may be administered in accordance with the method of the invention either alone or in combination with other known therapies for neovascularization. When co-administered with one or more other therapies, the pyrazolylbenzothiazole compound may be administered either simultaneously with the other treatment(s), or sequentially. If administered sequentially, the attending physician will decide on the appropriate sequence of administration, which may be before or after a second therapy.

Secondary therapies of interest include photodynamic therapy, for example verteporfin (VISUDYNE™) therapy, see, for example Madreperla (2001) *Arch Ophthalmol.* 119 (11):1606-1610; Harding (2001) *Eye* 15(Pt 3):407-12; Sharma (2001) *Can Fam Physician* 47:955, 963. Photocoagulation or transpupillary thermotherapy, see, e.g., Rogers et al. (2001) *Curr Opin Ophthalmol* 12(3): 212-5; Ardjomand et al. (2001) *Ophthalmologica* 215(3):241-4; Mainster et al. (2000) *Ophthalmic Surg Lasers* 31(5):359-73. Other therapies include, without limitation, those set forth in U.S. Pat. No. 6,297,228, "Use of angiostatic steroids in photodynamic therapy", U.S. Pat. No. 6,271,233 "Method for treating ocular neovascular diseases"; U.S. Pat. No. 6,248,734 "Use of photodynamic therapy for prevention of secondary cataracts"; U.S. Pat. RE37,180 "Photochemotherapeutical obstruction of newly-formed blood vessels"; U.S. Pat. No. 6,225,303 "Use of green porphyrins to treat neovasculature in the eye"; U.S. Pat. No. 6,217,895 "Method for treating and/or preventing retinal diseases with sustained release corticosteroids"; U.S. Pat. No. 6,214,819 "Method for treating ocular neovascular diseases", and the like.

Some eye diseases lend themselves to acute treatment while others require longer term therapy. Proliferative retinopathy can reach a threshold in a matter of days as seen in ROP, some cases of diabetic retinopathy, and neovascular glaucoma. Premature infants are at risk for neovascularization around what would be 35 weeks gestation, a few weeks after birth, and will remain at risk for a short period of time until the retina becomes vascularized. Diabetic retinopathy can be acute but may also smolder in the proliferative phase for considerably longer. Suitable animal models exist for determination of appropriate dosage, although the efficacy of a therapeutic effect for different mammals varies widely, for example doses typically are 20, 30 or even 40 times smaller (per unit body weight) in man than in the rat. Similarly the mode of administration can have a large effect on dosage. A murine model of oxygen-induced retinal neovascularization has been established which occurs in 100% of treated animals and is quantifiable (Smith et al. (1994) *Invest. Ophthalmol. Vis. Sci* 35:101-111). Bioactivity can be determined by methods including the Miles vessel permeability assay (Miles and Miles, J. *Physiol.* (Lond.) (1952) 118:228), which measures vessel permeability, and endothelial cell mitogenicity, which measures cell growth.

For local application, a range of about 0.05 to 0.2 or about 0.5 mg/ml of a pyrazolylbenzothiazole compound in an appropriate formulation is administered either intra-ocularly (intra-vitreous, subretinal, intra-anterior chamber, intra-scleral), peri-ocularly, or topically onto the cornea. For systemic application, a range of 0.05 to 100 mg/kg body weight, preferably less than about 10 mg/kg is administered to treat eye disease. For intra- or peri-ocular administration, a pyrazolylbenzothiazole compound in an injectable formulation is administered by either an intra-ocular injection at above-described concentrations and at a frequency of once every 2-6 months or by an intra-ocular implantation of a device or a specific formulation of an ILK inhibitor allowing sustained release of the ILK inhibitor over a period of time. For corneal application, an ILK inhibitor in an appropriate formulation is applied topically onto the cornea at a frequency of once very 4-6 hours. For systemic application, an ILK inhibitor in appropriate formulation is administered orally 1-3 times a day.

Thus, in one aspect, the present invention provides a method for treating ocular neovascularization, the method comprising administering a pyrazolylbenzothiazole compound or composition comprising such a compound as described herein to treat ocular neovascularization. Optionally, the treatment reduces or reverses the loss of visual acuity secondary to neovascularization of cornea, iris, retina or choroid. The methoer may further comprise administering a second therapy for ocular neovascularization, where a suitable second therapy is selected from the group consisting of photodynamic therapy, photocoagulation and transpupillary thermotherapy. In the present method, the ocular neovascularization may be selected from the group consisting of diabetic retinopathy, chronic glaucoma, retinal detachment, sickle cell retinopathy, age related macular degeneration (AMD) due to subretinal neovascularization; rubeosis iritis; inflammatory diseases; chronic uveitis; neoplasms; Fuchs' heterochromic iridocyclitis; neovascular glaucoma; corneal neovascularization; neovascularization resulting following a combined vitrectomy and lensectomy; retinal ischemia, choroidal vascular insufficiency, choroidal thrombosis, carotid artery ischemia; neovascularization of the optic nerve; and neovascularization due to penetration of the eye or contusive ocular injury. In various embodiments, the pyrazolylbenzothiazole compound is administered systemically, or intra-ocularly, or peri-ocularly, or is administered topically onto the cornea, or is administered by intra-ocular injection, or is administered by intra-ocular implantation.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric. The starting materials used in the examples can be purchased from a chemical supplier such as Aldrich and Lancaster or can be prepared following the preparation procedures described herein:

EXAMPLES

Example 1

Preparation 1: Synthesis of 2-Amino-4-fluorobenzenethiol

To a solution of 2-chloro-5-fluoronitrobenzene (1.81 g, 10.31 mmol) dissolved in 30 mL of deionized water at room temperature was added sodium sulfide nonahydrate (9.90 g, 41.24 mmol) in a single portion. The resulting solution was heated to reflux and stirred under nitrogen for 32 hours. The resulting light yellow solution was then cooled to room temperature and was washed with 5×50 mL of ethyl acetate. The organic phase was dried over anhydrous magnesium sulfate, filtered, and evaporated to yield a yellow oil. The crude material was purified by flash chromatography eluting with $CH_2Cl_2$:MeOH=10:1 to yield 0.36 g (25%) of the title compound. MS (m/z, ES+): 144.0 (M+1, 100%); IR (KBr): 3430, 3340, 1615, 1573, 1482, 1281, 1248, 1172, 1124, 1044, 975, 840, 792 $cm^{-1}$; $^1H$ NMR (300 MHz, ppm, DMSO-$d_6$) δ: 6.89 (dt, 1H), 6.50 (dd, 1H), 6.21 (dt, 1H), 5.80 (br s, 2H).

Preparation 2: Synthesis of Thiazolo[5,4-b]pyridin-2-ylamine

A suspension of 2-chloro-3-aminopyridine (3 g, 23 mmole), and ammonium thiocyanate (3.5 g, 46.5 mmole) in 23 mL of ethanol was acidified with conc. HCl to pH ~1 (~1.8 mL). The reaction mixture was heated to 85° C. for 3 days. At this point, the solvent was evaporated and residual water was removed aziotropically by the distillation of 2-propanol. The yellow residue was mixed with 12 mL of 7 M ammonium hydroxide and 7 mL of chloroform. The solid was isolated by filtration to yield 1.50 g (43%) of the product as a white powder. MS (m/z, ES+): 152 (M+1, 100%).

Preparation 3: Synthesis of 4-Fluorobenzothiazol-2-ylamine

To a suspension of (2-fluorophenyl)thiourea (1.7 g, 10.0 mmol) in chloroform (25 ml) was added a solution of bromine (0.51 mL; 10.0 mmol) dropwise at room temperature. The resulting mixture was heated under reflux for 3 hrs. The solvent was evaporated, water was added and the mixture was neutralized with ammonium hydroxide. The resulting white precipitation was collected by filtration and dried to yield 1.2 g (72%) of the title compound which was used in the subsequent step without further purification.

Preparation 4: Synthesis of 7-Chloro-4-methoxybenzothiazol-2-ylamine

The title compound was prepared from (5-chloro-2-methoxyphenyl)thiourea (2.17 g, 10.0 mmol) using a procedure analogous to that described in Preparation 3. The title compound was isolated in a yield of 2.1 g (98%).

Preparation 5: Synthesis of 4-Amino-2-fluorobenzoic acid

To a solution of 2-fluoro-4-nitrobenzoic acid (1.0 g, 5.4 mmol) in 20 mL of a mixture of acetic acid and methanol (1:1), was added a catalytic amount of palladium on charcoal (25 mg). The reaction was stirred under an atmosphere of hydrogen gas at room temperature overnight. The mixture was then filtered through celite and the solvent was removed by evaporation to yield 0.86 g (100%) of the title compound as a cream coloured solid.

Preparation 6: Synthesis of 4-Amino-2-fluoro-N-methylbenzenesulfonamide

A solution of N-(3-fluorophenyl)acetamide (20.0, 0.13 mol) in chlorosulfonic acid (150 mL) was heated to 75° C. for 1 hr. The solution was allowed to cool to room temperature and was poured over ice. The resulting slurry was extracted with dichloromethane. The combined organic extracts were dried over magnesium sulfate, filtered and evaporated to yield 15.5 g (47%) of 4-acetylamino-2-fluorobenzenesulfonyl chloride as a paste. The crude material was used in the subsequent step without further purification.

The above prepared 4-acetylamino-2-fluorobenzenesulfonyl chloride (2 g, 7.9 mmol) was dissolved in dichloromethane and methylamine (9.9 mL of a 2M solution in THF, 19.9 mmol) was added. The reaction was stirred at room temperature for 2 hrs. The solvent was then evaporated under reduced pressure and the resulting solid was suspended in 50 mL of water. The solid was isolated by filtration and dried to yield 1.55 g (79%) of N-(3-fluoro-4-methylsulfamoylphenyl) acetamide which was used in the subsequent step without further purification.

The above prepared N-(3-fluoro-4-methylsulfamoylphenyl)acetamide (1.55 g, 6.3 mmol) was suspended in 40 mL of 6M HCl and heated to reflux for 1 hr. The reaction was cooled in an ice bath and an NaOH solution was added to adjust the mixture to pH 5. The resulting white precipitate was isolated by filtration and was washed with water and dried to yield 1.07 g (83%) of the title compound. MS (m/z, ES+): 205.0 (M+1, 100%); $^1H$ NMR (500 MHz, ppm, DMSO-$d_6$): 7.35 (m, 1H), 7.12 (m, 1H), 6.40 (m, 2H), 6.23 (s, 2H), 2.40 (s, 3H).

Preparation 7: Synthesis of 4-Amino-N-methylbenzenesulfonamide

To an ice cold solution of 4-nitrobenzenesulfonyl chloride (2.7 g, 12 mmol) and triethylamine (27 mmol) in 60 mL of dry THF was added methylamine (8 mL of a 2 M solution in THF, 16 mmol). The mixture was stirred at room temperature overnight. Brine was added and the reaction solution was extracted with ethyl acetate. The combined organic extracts were dried over sodium sulfate, filtered, and evaporated to yield 4-nitrobenzenesulfonic acid methylamide as an oil. The crude material was used in the subsequent reaction without further purification.

To a solution of the crude 4-nitrobenzenesulfonyl methylamide prepared above in 45 mL of ethanol, was added a 1 mL slurry of Raney Nickel. Hydrazine monohydrate (18 mmol) was added slowly in several portions. A change in the solution colour from yellow to colourless indicated the reaction was complete. The mixture was stirred for an additional 1 hr. The solids were removed by filtration and the solvent was evaporated. The resulting crude material was purified by flash column chromatography eluting with $CH_2Cl_2$:MeOH=10:1 to yield 2.09 g (90% for two steps) of the title compound as a pale orange powder.

Preparation 8: Synthesis of 2-Aminobenzothiazole-7-carboxylic acid

3-Isothiocyanatobenzoic acid (1.0 g, 5.6 mmol) in 40 mL of ethanol was stirred at room temperature for 1 hr while ammonia gas was bubbled through the solution. The resulting white precipitate was isolated by filtration. The volume of the filtrate was reduced to induce the precipitation of additional white solid that was also isolated by filtration. The total yield of 3-thioureidobenzoic acid was 1.06 g (97%).

To a suspension of 3-thioureidobenzoic acid (1.06 g, 5.41 mmol) in chloroform (25 mL) was added a solution of bromine (0.4 mL, 8.0 mmol) dropwise at room temperature. The resulting mixture was heated under reflux for 3 hrs and allowed to stir at room temperature for 60 hrs. The solvent was evaporated, water was added and the resulting solids were isolated by filtration. The crude product was washed with water and dried to yield 1.03 g (98%) of the title compound as a gray solid.

Preparation 9: Synthesis of
2-Cyanomethylbenzothiazole-6-sulfonic acid amide

1. To a suspension of 4-amino-N-methylbenzenesulfonamide (43 g, 250 mmol) in 400 mL acetic acid was added ammonium thiocyanate (49 g, 650 mmol) in several portions. After the mixture had been stirred at room temperature for 30 min, a solution of bromine (13 mL, 250 mmol) in 160 mL of acetic acid was added dropwise. The reaction was then stirred at room temperature for 64 hrs. The resulting solids were isolated by filtration, washed with saturated $NaHCO_3$ solution and water, and dried to yield 60 g of material. The filtrate was evaporated to dryness, the residue was suspended in a saturated $NaHCO_3$ solution and additional product was extracted into ethyl acetate. The organic extracts were dried over sodium sulfate, filtered, and evaporated to yield an additional 6.2 g of product to give a total of 66 g of 2-aminobenzothiazole-6-sulfonic acid amide.

2. A solution of 2-aminobenzothiazole-6-sulfonic acid amide (66 g, 287 mmol) and NaOH (90 g, 2.3 mol) in 400 mL of water was refluxed under argon overnight. The reaction solution was cooled in ice bath and was acidified to approximately pH 3 by the addition of concentrated HCl (~180 mL). The resulting precipitate was isolated by filtration and dried to yield 74 g of 4-amino-3-mercaptobenzenesulfonamide as a white powder. MS (m/z, ES+): 205 (M+1, 100%).

3. A suspension of 4-amino-3-mercaptobenzenesulfonamide (74 g, 208 mmol) and malononitrile (25 g, 375 mmol) in 650 mL of ethanol with 1.3 mL of conc. HCl was refluxed under argon overnight. The dark brown solids were isolated by filtration and were washed with ethanol and ether to yield approximately 30 g of the crude product. The volume of the filtrate was reduced by evaporation and the solids that precipitated were isolated by filtration to yield an additional 12 g of product. The crude material was purified by flash column chromatography eluting with $CH_2Cl_2$:MeOH:ammonia (60:20:1 mL) to yield a total of 22.2 g (35% for three steps) of the title compound as an orange powder.

Preparation 10: Synthesis of
(5-Fluoro-6-methoxybenzothiazol-2-yl)acetonitrile

The title compound was prepared two steps starting from 6-fluoro-5-methoxyaniline (1.41 g, 10 mmol) and ammonium thiocyanate (1.83 g, 24 mmol) using a procedure analogous to that described in Preparation 9. The title compound was isolated in a yield of 240 mg (10% for 3 steps).

Preparation 11: Synthesis of
(6-Methoxybenzothiazol-2-yl)acetonitrile

The title compound was prepared two steps starting from 6-methoxybenzothiazol-2-ylamine (10 g, 55 mmol) using a procedure analogous to that described in Preparation 9. The title compound was isolated in a yield of 8.5 g (75% for 2 steps).

Preparation 12: Synthesis of 2-(5-Fluoro-6-methoxybenzolthiazole)-3,3-bis-methylsulfanylacrylonitrile To a stirred cool solution of 2-(5-fluoro-6-methoxybenzolthiazole)acetonitrile, (1.48 g, 6.65 mmol), carbon disulfide (0.90 mL, 15 mmol) and iodomethane (1.7 mL, 27 mmol) in anhydrous dimethylsulfoxide (40 mL) was added sodium hydride (540 mg of a 60% slurry in mineral oil, 13.5 mmol) in portions under an inert atmosphere. The dark red reaction mixture was stirred at 5° C. for 30 minutes and then at room temperature for 2 hrs before it was quenched with saturated aqueous ammonium chloride (20 mL) and diluted with distilled water. The resulting orange precipitate was isolated by filtration, washed with water, suspended in isopropanol and re-filtered. The precipitate was then dried under vacuum to yield 1.61 g (74%) of the title compound as a yellow solid. MS (m/z, ES+): 328 (M+1, 100%).

Preparation 13: Synthesis of 2-(6-Methoxybenzolthiazole)-3,3-bis-methylsulfanylacrylonitrile The title compound was prepared from 2-(6-methoxybenzolthiazole)-acetonitrile (1.50 g, 7.34 mmol) using a procedure analogous to that described in Preparation 12. The title compound was isolated in a yield of 1.63 g (72%). MS (m/z, ES+): 309 (M+1, 60%), 465 (by-product, 100%).

Preparation 14: Synthesis of 2-Benzothiazol-2-yl-3,3-bismethylsulfanylacrylonitrile The title compound was prepared from benzothiazol-2-ylacetonitrile (1.74 g, 10 mmol) using a procedure analogous to that described in Preparation 12. The title compound was isolated in a yield of 1.25 g (45%). MS (m/z, ES+): 279 (M+1, 100%). m/z Preparation 15: Synthesis of
Benzoxazol-2-ylacetonitrile Compound prepared by this procedure in Sakamoto, M.; Nozaka, A.; Shimamoto, M.; Ozaki, H.; Suzuki, Y.; Yoshioka, S.; Nagano, M.; Okamura, K.; Date, T.; Tamura, O. *J. Chem. Soc. Perkin Trans. I*(1995), 1759 and references therein.

To a solution of 2-aminophenol (5.0 g, 45.8 mmol) dissolved in 115 mL of anhydrous ethanol and 8 mL of glacial acetic acid was added malonitrile (9.08 g, 140 mmol) at 100° C. The resulting homogeneous solution was refluxed for 24 hours and the solvent was removed in vacuo to yield a red/brown oil. The oil was diluted with $CH_2Cl_2$ (100 mL) and any remaining solids were then removed by filtration. The mother liquor was washed twice with a saturated sodium bicarbonate solution and twice with water, dried over magnesium sulfate, filtered and evaporated to yield 5.2 g (71%) of the product as a yellow oil. This material was used in the subsequent reaction without further purification.

Preparation 16: Synthesis of 2-Benzoxazol-2-yl-3,3-bismethylsulfanylacrylonitrile (Augustin, M.; Doelling, W.; *J. Prakt. Chem.* (1982) 1, 3).

To a solution of benzoxazol-2-ylacetonitrile (2.07 g, 13.1 mmol) dissolved in 35 mL of DMSO at room temperature under argon atmosphere was added carbon disulfide (1.10 g, 14.4 mmol) followed by iodomethane (5.20 g, 36.7 mmol). This solution was then cooled to 10° C. and sodium hydride (1.05 g, 60% by wt in oil, 26.3 mmol) was added over a period of several minutes. The solution was allowed to warm to room temperature and stirred overnight. The reaction was then quenched with an ammonium chloride solution and was extracted with 5×50 mL of ethyl acetate. The ethyl acetate was washed with brine solution (3×50 mL) and water (3×30 mL). The organic phase was dried over magnesium sulfate, filtered, and evaporated to yield a red oil. The crude material was purified by flash column chromatography eluting with $CH_2Cl_2$:MeOH=98:2 to yield 1.96 g (57%) of the desired product as a yellow oil. MS (m/z, ES+): 236.68 (M+1, 100%). The following examples illustrate the preparation of compounds disclosed in this invention.

Example 2

Synthesis of
4-Benzothiazol-2-yl-1H-pyrazol-3-ylamine

A mixture of 2-aminobenzenethiol (100 mg, 0.8 mmol) and 3-aminopyrazole-4-carbonitrile (86 mg, 0.8 mmol) in 3 g of polyphosphoric acid was heated at 200° C. for 3 hours. The mixture was then poured into ice water and was neutralized with conc. Ammonium hydroxide solution. The resulting yellow solid was isolated by filtration and washed with cold water to yield the title compound (70 mg, 40%). MS (m/z, ES+): 217 (M+1, 100%); $^1$H NMR (300 MHz, ppm, DMSO-$d_6$): δ 7.97 (d, $^3$J=7.8 Hz, 1H), 7.88 (s, 1H), 7.84 (d, $^3$J=8.0 Hz, 1H), 7.42 (m, 1H), 7.29 (m, 1H), 6.3 (br s, 2H).

The following compounds were prepared in a manner analogous to the procedure described in Example 2.

4-(1H-Benzoimidazol-2-yl)-1H-pyrazol-3-ylamine: The title compound (0.031 g) was prepared starting from 0.30 g (2.8 mmol) 1,2-phenyldiamine and 0.30 g (2.8 mmol) 3-aminopyrazole-4-carbonitrile. MS (m/z, ES+): 200 (M+1, 100%). Yield=6%.

4-(1H-Benzoimidazol-2-yl)-1H-pyrazole-3,5-diamine: The title compound (0.047 g) was prepared starting from 0.46 g (4.22 mmol) of 1,2-phenyldiamine and 0.52 g (4.22 mmol) of 3,5-diaminopyrazole-4-carbonitrile. MS (m/z, ES+): 215 (M+1, 100%). Yield=5%.

2-(1H-Pyrazol-4-yl)-benzothiazole: The title compound (0.055 g) was prepared starting from 0.11 g (0.090 mmol) of 2-aminophenol and 0.10 g (0.90 mmol) of 4-pyrazolecarboxylic acid in 5 mL of anhydrous ethanol and 1 mL of glacial acetic acid at reflux for 24 hours. MS (m/z, ES+): 202 (M+1, 100%); $^1$H NMR (400 MHz, ppm, DMSO-$d_6$) 13.45 (br s, 1H), 8.32 (br s, 2H), 8.00 (dd, 2H), 7.43 (dt, 2H). Yield=34%.

Example 3

Synthesis of 4-(6-Bromobenzothiazol-2-yl)-5-methyl-2H-pyrazol-3-ylamine

1. A mixture of 4-bromoaniline (1.72 g 10 mmol) and ammonium thiocyanate (3.05 g, 40 mmol) in acetic acid (15 mL) was stirred for approximately 15 minutes until a homogeneous solution was obtained. A solution of bromine (1.6 g, 10 mmol) in acetic acid (7 mL) was then added to the resulting mixture over a period of 20 minutes. The reaction mixture was stirred overnight at room temperature. The resulting precipitate was isolated by filtration and dried under high vacuum to afford the crude product which was used in the following reaction without further purification.

2. A suspension of 6-bromobenzothiazol-2-ylamine (2.29 g, 10 mmol) prepared above in sodium hydroxide (40 mL of a 6 M solution, 240 mmol) was refluxed under argon overnight. The reaction mixture was cooled in an ice bath and was acidified to between pH 3 and 5 with conc. HCl. The resulting precipitate was isolated by filtration, washed with water and dried under high vacuum to afford the crude product that was used in the following reaction without further purification.

3. A mixture of 2-amino-5-bromobenzenethiol (1.29 g, 6.3 mmol) and malononitrile (0.66 g, 10 mmol) in ethanol (20 mL) was heated to reflux overnight. The reaction was then cooled to room temperature and the resulting precipitate was isolated by filtration to afford the crude product that was used in the following reaction without further purification.

4. A mixture of (6-bromobenzothiazol-2-yl)acetonitrile (4.9 mmol) and trimethyl orthoacetate (0.71 g, 5.88 mmol) in acetic anhydride (12 mL) was heated at 100° C. for 5 h. The reaction mixture was then cooled to room temperature. The resulting precipitate was isolated by filtration to afford the crude product which was used in the following reaction without further purification.

5. A solution of 2-(6-bromobenzothiazol-2-yl)-3-methoxybut-2-enenitrile (0.96 g, 3.1 mmol) and hydrazine hydrate (0.3 mL, 5.4 mmol) in methanol (30 mL) was heated to reflux overnight. The reaction was then cooled to room temperature. The resulting solid was isolated by filtration and was purified by flash chromatography to yield the title product. MS (m/z, ES+): 308.9 (Br$^{79}$M+1, 100%), 310.9 (Br$^{81}$M+1, 100%). Yield=5%.

The following compounds were prepared in a manner analogous to the procedure described in Example 3.

2-(3-Amino-5-methyl-1H-pyrazol-4-yl)-benzothiazole-6-sulfonic acid amide: The title compound (23 mg) was prepared in five steps starting from 3.4 g (20 mmole) of 4-aminobenzenesulfonamide. MS (m/z, ES+): 310 (M+1, 100%). $^1$H NMR (300 MHz, ppm, DMSO-$d_6$): 11.78 (br s, 1H), 8.47 (s, 1H), 7.98 (d, 1H), 7.86 (d, 1H), 6.68 (br s, 2H), 7.37 (s, 2H), 2.41 (s, 3H).

4-(6-Methanesulfonylbenzothiazol-2-yl)-5-methyl-1H-pyrazol-3-ylamine: The title compound (46 mg) was prepared in four steps starting from 1.0 g (4.4 mmol) of 2-amino-6-methanesulfonylbenzothiazol. MS (m/z, ES+): 309 (M+1, 100%).

4-(6-Methoxybenzothiazol-2-yl)-5-methyl-1H-pyrazol-3-ylamine: The title compound (32 mg) was prepared in two steps starting from 140 mg (0.68 mmol) of (6-methoxybenzothiazol-2-yl)acetonitrile. MS (m/z, ES+): 261 (M+1, 100%).

4-(6-Fluorobenzothiazol-2-yl)-5-methyl-1H-pyrazol-3-ylamine: The title compound (55 mg) was prepared in four steps starting from 1.0 g (5.95 mmol) of 2-amino-6-fluorobenzothiazole. MS (m/z, ES+): 248 (M+1, 100%).

5-Methyl-4-thiazolo[5,4-b]pyridin-2-yl-1H-pyrazol-3-ylamine: The title compound (162 mg) was prepared in four steps starting from 1.5 g (10 mmol) of thiazolo[5,4-b]pyridin-2-ylamine. MS (m/z, ES+): 232 (M+1, 100%).

4-Benzothiazol-2-yl-5-methyl-1H-pyrazol-3-ylamine: The title compound (42 mg) was prepared in two steps starting from 174 mg (1.0 mmol) of benzothiazol-2-ylacetonitrile. MS (m/z, ES+) 231 (M+1, 100%).

4-(5-Fluoro-6-methoxybenzothiazol-2-yl)-5-methyl-1H-pyrazol-3-ylamine (474-98E): The title compound (32 mg) was prepared in two steps starting from 0.24 g (0.86 mmol) of (5-fluoro-6-methoxybenzothiazol-2-yl)acetonitrile. MS (m/z, ES+): 279.1 (M+1, 100%).

2-(5-Amino-3-methyl-1H-pyrazol-4-yl)-benzothiazole-6-carboxylic acid amide (574-3B): The title compound (64 mg)

was prepared in five steps starting from 1.4 g (10 mmol) of 4-aminobenzamide. MS (m/z, ES+): 274.0 (M+1, 100%).

N-[2-(5-Amino-3-methyl-1H-pyrazol-4-yl)-benzothiazol-6-yl]acetamide (574-8E): The title compound (160 mg) was prepared in five steps starting from 1.5 g (10 mmol) of N-(4-aminophenyl)acetamide. MS (m/z, ES+): 245.1 (M−42, 100%); MS (m/z, ES−): 243.2 (M−44, 100%); $^1$H NMR (300 MHz, ppm, DMSO-$d_6$): δ 11.9-11.6 (br s, 1H), 7.79 (s, 1H), 7.73 (d, 1H), 7.24 (d, 1H), 6.50 (br s, 1H), 5.78 (br s, 1H), 2.41 (s, 3H), 2.38 (br s, 3H); IR (KBr): 3518, 3207, 1607 (vs), 1544, 1506, 1023, 963, 821 cm$^{-1}$.

4-(6-Chlorobenzothiazol-2-yl)-5-methyl-2H-pyrazol-3-ylamine (598-38): The title compound (396 mg) was prepared in four steps starting from 1.0 g (5.4 mmol) of 6-chloro-2-aminobenzothiazole. During the final step, 4 drops of conc HCl were added while the solution was under reflux to form the pyrazole ring. MS (m/z, ES+): 265.0 (Cl$^{35}$ M+1, 100%), 267.0 (Cl$^{37}$ M+1, 50%).

4-(4-Fluorobenzothiazol-2-yl)-5-methyl-2H-pyrazol-3-ylamine (598-45): The title compound (325 mg) was prepared in four steps starting from 1.22 g (7.3 mmol) of 4-fluorobenzothiazol-2-ylamine. During the final step, 4 drops of conc HCl were added while the solution was under reflux to form the pyrazole ring. The solid was removed by filtration and the resulting solution was evaporated to afford the title compound. MS (m/z, ES+): 249.0 (M+1, 100%).

4-(5-Trifluoromethylbenzothiazol-2-yl)-5-methyl-2H-pyrazol-3-ylamine (598-66): The title compound (621 mg) was prepared in three steps starting from 1.0 g (4.4 mmol) of 2-amino-4-trifluoromethylbenzenethiol hydrochloride. During the final step, 4 drops of conc HCl were added while the solution was under reflux to form the pyrazole ring. MS (m/z, ES+): 299.0 (M+1, 100%).

4-(7-Chloro-4-methoxybenzothiazol-2-yl)-5-methyl-2H-pyrazol-3-ylamine (598-58): The title compound (176 mg) was prepared in four steps starting from 2.1 g (9.8 mmol) of 7-chloro-4-methoxybenzothiazol-2-ylamine. During the final step, a catalytic amount of p-toluenesulfonic acid was added while the solution was under reflux to form the pyrazole ring. MS (m/z, ES+): 295.0 (Cl$^{35}$M+1, 100%), 297.0 (Cl$^{37}$M+1, 50%).

2-(3-Amino-5-methyl-1H-pyrazol-4-yl)-benzothiazole-6-carboxylic acid (574-26E1): The title compound (1.58 g) was prepared in five steps starting from 16.5 g (100 mmol) of 4-aminobenzoic acid ethyl ester. During the final step, 4 drops of conc. HCl were added while the solution was under reflux to form the pyrazole ring. MS (m/z, ES+): 275 (M+1, 100%).

4-(6-Bromo-5-fluorobenzothiazol-2-yl)-5-methyl-1H-pyrazol-3-ylamine (574-28E): The title compound (765 mg) was prepared in five steps starting from 5.0 g (26.3 mmol) of 4-bromo-3-fluoroaniline. During the final step, a catalytic amount of p-toluenesulfonic acid was added while the solution was under reflux to form the pyrazole ring. MS (m/z, ES+): 327.0 (Br$^{79}$M+1, 100%), 329.0 (Br$^{81}$M+1, 100%).

2-(3-Amino-5-methyl-1H-pyrazol-4-yl)-benzothiazole-6-sulfonic acid (2,6-dimethyl-pyrimidin-4-yl)-amide (474-92B): The title compound (93 mg) was prepared in five steps starting from sulfisomidine with the exception that in step 2 KOH was replace with sodium sulfide (5.0 g). MS (m/z, ES+): 416.0 (M+1, 100%).

2-(3-Amino-5-methyl-1H-pyrazol-4-yl)-benzothiazole-6-sulfonic acid methylamide (503-55B): The title compound (168 mg) was prepared in five steps starting from 2.0 g (11 mmole) of 4-amino-N-methylbenzenesulfonamide. MS (m/z, ES+): 324.0 (M+1, 100%). $^1$H NMR (400 MHz, ppm, DMSO-$d_6$): δ 11.80-12.15 (br, 1H), 8.46 (s, 1H), 7.99-5.87 (br m, 2H), 7.79 (d, 1H), 7.74 (dd, 1H), 6.72 (br s, 2H), 2.43 (s, 3H), 2.42 (s, 3H).

2-(3-Amino-5-methyl-1H-pyrazol-4-yl)-5-fluorobenzothiazole-6-sulfonic acid methylamide (574-37E): The title compound (3 mg) was prepared in five steps starting from 1.9 g (10 mmol) of 4-amino-2-fluoro-N-methylbenzenesulfonamide. MS (m/z, ES+): 342.2 (M+1, 100%).

4-(5-Fluoro-6-methylbenzothiazol-2-yl)-5-methyl-2H-pyrazol-3-ylamine (610-89): The title compound (24 mg) was prepared in five steps starting from 3-fluoro-4-methylaniline. MS (m/z, ES+): 263.04 (M+1, 100%).

5-Methyl-4-(4,5,6-trifluorobenzothiazol-2-yl)-1H-pyrazol-3-ylamine (598-75): The title compound (520 mg) was prepared in five steps starting from 3.0 g (20 mmol) of 2,3,4-trifluoroaniline. During the final step, 4 drops of conc. HCl were added while the solution was under reflux to form the pyrazole ring. MS (m/z, ES+): 285.0 (M+1, 100%).

2-(3-Amino-5-methyl-1H-pyrazol-4-yl)benzothiazole-7-carboxylic acid methyl ester (598-85): The title compound (33 mg) was prepared in two steps starting from 1.1 g (5.6 mmol) 2-aminobenzothiazole-7-carboxylic acid. Excess trimethyl orthoacetate (8.0 mmol) was used to convert the acid group to the methyl ester. During the final step, a catalytic amount of p-toluenesulfonic acid was added while the solution was under reflux to form the pyrazole ring. MS (m/z, ES+): 289.2 (M+1, 100%).

2-(3-Amino-5-methyl-1H-pyrazol-4-yl)-5-fluorobenzothiazole-6-carboxylic acid methyl ester (574-45F): The title compound (50 mg) was prepared in five steps starting from 860 mg (5.5 mmol) of 4-amino-2-fluorobenzoic acid. Excess trimethyl orthoacetate was used to convert the acid group to a methyl ester during step 4. During the final step, 4 drops of conc. HCl were added while the solution was under reflux to form the pyrazole ring. MS (m/z, ES+): 307.0 (M+1, 100%).

4-(5-Trifluoromethylbenzothiazol-2-yl)-1H-pyrazol-3-ylamine: The title compound (29 mg) was prepared in three steps starting from 1.1 g (5.0 mmol) of 2-amino-4-trifluoromethylbenzenethiol hydrochloride. Triethyl orthorcarbonate (1.2 equiv.) was substituted for trimethyl orthoacetate. MS (m/z, ES+): 285 (M+1, 100%).

4-(6-Fluorobenzothiazol-2-yl)-1H-pyrazol-3-ylamine (474-67B): The title compound (37 mg) was prepared in four steps starting from 2-amino-6-fluorobenzathiazole. Triethyl orthorcarbonate (1.2 equiv.) was substituted for trimethyl orthoacetate. MS (m/z, ES+): 235.0 (M+1, 100%).

2-(3-Amino-1H-pyrazol-4-yl)-5-fluorobenzothiazole-6-sulfonic acid amide (574-42B): The title compound (58 mg) was prepared in five steps starting from 4-amino-2-fluoro-N-methyl-benzenesulfonamide. Triethyl orthorcarbonate (1.2 equiv.) was substituted for trimethyl orthoacetate. MS (m/z, ES+): 314.0 (M+1, 100%); $^1$H NMR (300 MHz, ppm, DMSO-$d_6$): δ 12.16 (br s, 1H), 8.46 (d, 7.1 Hz, 1H), 7.82 (d, 1H), 7.8-8.0 (m, 1H), 7.63 (s, 2H), 6.7-5.5 (2H).

4-(5-Fluoro-6-methylbenzothiazol-2-yl)-2H-pyrazol-3-ylamine (610-93): The title compound (54 mg) was prepared in five steps starting from 3-fluoro-4-methylaniline. Triethyl orthorcarbonate (1.2 equiv.) was substituted for trimethyl orthoacetate. MS (m/z, ES+): 249.05 (M+1, 100%).

2-(5-Amino-1H-pyrazol-4-yl)-benzothiazole-6-sulfonic acid methylamide (599-77B2): The title compound (107 mg) was prepared in five steps starting from 4-amino-N-methyl-benzenesulfonamide. N,N-Dimethylformamide dimethyl acetal (1.2 equiv.) was substituted for trimethyl orthoacetate. MS (m/z, ES+): 310.0 (M+1, 100%); $^1$H NMR (300 MHz, ppm, DMSO-d$_6$): δ 12.1 (br s, 1H), 8.43 (d, 1H), 8.0 (br s, 1H), 7.97 (d, 1H), 7.78 (dd, 1H), 7.38 (q, 1H), 6.5 (br s, 1H), 5.9 (br s, 1H), 2.44 (d, 3H).

4-Benzothiazol-2-yl-5-ethyl-1H-pyrazol-3-ylamine: The title compound (75 mg) was prepared in two steps starting from 174 mg (1.0 mmol) of benzothiazol-2-ylacetonitrile and 211 mg (1.2 mmol) of triethyl orthopropionate. MS (m/z, ES+): 245 (M+1, 100%).

Example 4

Synthesis of 2-(5-Amino-3-methyl-1H-pyrazol-4-yl)-benzothiazole-5-sulfonic acid methylamide (574-12E)

1. To a solution of 4-chloro-3-nitrobenzenesulfonyl chloride (2.0 g, 7.8 mmol) in THF (10 mL) was added excess methylamine (2M solution in THF). The reaction solution was stirred at room temperature for 1 hr. Water was then added and the product was extracted into chloroform. The combined extracts were washed, dried over sodium sulfate, filtered and evaporation to yield 2.3 g of the crude 4-chloro-N-methyl-3-nitrobenzenesulfonamide as an oil. The crude material was used in the subsequent step without further purification.

2. An ethanolic solutions of sodium disulphide was prepared by dissolving sodium sulfide nonahydrate (2.0 g, 8.5 mmol) in hot ethanol (9 mL) and then adding sulfur (0.27 g, 8.5 mmol). This was cooled to room temperature and added dropwise to a solution of the above prepared crude 4-chloro-N-methyl-3-nitrobenzenesulfonamide (2.3 g) in ethanol (15 mL). After the addition had been completed, the resulting precipitate was isolated by filtration and was washed with ethanol to yield 1.5 g (79% for two steps) of 4,4'-dithiobis(N-methyl-3-nitrobenzenesulfonamide) as a yellow powder. MS (m/z, ES−): 492.9 (M−1, 100%).

3. To a solution of 4,4'-dithiobis(N-methyl-3-nitrobenzenesulfonamide) (1.5 g, 3.1 mmol) in ethanol (70 mL) was added a solution of tin chloride dihydrate (5.5 g) in hydrochloric acid (10 mL of a 2N solution). The reaction mixture was heated to reflux over night and then malononitrile (660 mg, 10 mmol) was added. The resulting mixture was refluxed for an additional 5 hrs and was then cooled to room temperature and diluted with water. The solid was isolated by filtration and was purified by flash column chromatography to yield 120 mg (8%) of 2-cyanomethylbenzothiazole-5-sulfonic acid methylamide.

4. A mixture of 2-cyanomethylbenzothiazole-5-sulfonic acid methylamide (120 mg, 0.45 mmol) and trimethyl orthoracetate (270 mg, 2.2 mmol) in acetic anhydride (2 mL) was heated at 100° C. for 5 hrs. The reaction mixture was cooled to room temperature. The resulting precipitate was isolated by filtration to yield 120 mg (83%) of 2-(1-cyano-2-methoxypropenyl)benzothiazole-5-sulfonic acid methylamide. The product was used in the subsequent step without further purification. MS (m/z, ES+): 324 (M+1, 100%).

5. To a suspension of 2-(1-cyano-2-methoxypropenyl)benzothiazole-5-sulfonic acid methylamide (120 mg, 0.37 mmol) in 4 mL of methanol, was added hydrazine hydrate (20 μL). The mixture was heated to reflux for 5 hrs and then 1 drop of conc. hydrochloric acid was added to the reaction mixture. The mixture was refluxed for an additional 5 min and was then allowed to cool. The volume of solvent was reduced under reduced pressure and a solid formed. The solid was isolated by filtration and was washed with methanol and then water and dried to yield 51 mg (43%) of the title compound as a cream coloured powder. MS (m/z, ES+): 324.0 (M+1, 100%).

The following compounds were prepared in a manner analogous to the procedure described in Example 4.

2-(5-Amino-3-methyl-1H-pyrazol-4-yl)benzothiazole-5-carboxylic acid ethyl ester (574-19): The title compound (0.50 g) was prepared in four steps starting from 5.0 g (22 mmol) of 4-chloro-3-nitrobenzoic acid ethyl ester. MS (m/z, ES+): 303 (M+1, 100%).

Example 5

Synthesis of 4-(5-Fluorobenzothiazol-2-yl)-5-methyl-2H-pyrazol-3-ylamine

1. To a solution of 4-fluoro-2-nitroaniline (1.6 g, 10 mmol) in conc. sulfuric acid (3 mL) and water (3 mL) at 5° C. was added a solution of sodium nitrite (760 mg, 11 mmol) in 3 mL of water. After stirring for 40 minutes, a solution of potassium thiocyanate (1.0 g, 10 mmol) in 2 mL of water was added. The solution was then poured into a vigorously stirring suspension of cuprous thiocyanate (1.8 g, 15 mmol) in 6 mL of water at 5° C. The resulting mixture was stirred for 2 hrs and left to stand in the refrigerator overnight. The resulting solid was isolated by filtration and was washed with hot dichloromethane. The dichloromethane extracts were dried with sodium sulfate, filtered and evaporated to yield 1.90 g (96%) of a yellow solid which was used in the subsequent reaction without further purification. IR (KBr disc): 2158 (m) cm$^{-1}$.

2. To a suspension of the crude product prepared above (1.90 g) in ethanol (10 mL) was added a solution of sodium sulfide in water (30 mL). The resulting deep red mixture was heated to reflux for 1 hr. The mixture was cooled, acidified to approximately pH 5 and extracted with dichloromethane. The organic extracts were combined, washed with water, dried over sodium sulfate, filtered, and evaporated to yield 2.1 g of crude 4-fluoro-2-nitrobenzenethiol which was used in the subsequent step without further purification. MS (m/z, ES+): 174.0 (M+1, 100%).

3. To a solution of 2.1 g of the crude 4-fluoro-2-nitrobenzenethiol prepared above in ethanol was added SnCl$_2$ dihydrate (6.7 g, ca. 3 equi.). The mixture was heated to reflux overnight. To this mixture was added molanonitrile (400 mg). After refluxing for an additional 5 hrs, the reaction mixture was cooled and filtered. The volume of solvent was reduced by evaporation and water was added to induce the formation of a precipitate. The crude product (940 mg) was isolated by filtration and was then purified by flash chromatography eluting with hexanes:EtOAc=1:1 to yield 360 mg (19% for 3 steps) of 5-fluorobenzothiazol-2-yl)acetonitrile as a pale greenish solid. MS (m/z, ES+): 193 (M+1, 100%).

4. A mixture of 5-fluorobenzothiazol-2-yl)acetonitrile (360 mg, 1.9 mmol) and trimethyl orthoracetate (270 mg, 2.3 mmol) in acetic anhydride (2 mL) was heated at 100° C. for 5 hrs. The reaction mixture was cooled and the resulting precipitate was isolated by filtration, washed with ether, and dried to yield 330 mg (71%) of 2-(5-fluorobenzothiazol-2-yl)-3-methoxybut-2-enenitrile as a red solid. MS (m/z, ES+): 249 (M+1, 100%).

5. A suspension of 2-(5-fluorobenzothiazol-2-yl)-3-methoxybut-2-enenitrile (330 mg, 1.3 mmol) and hydrazine hydrate (70 μL) in methanol (40 mL) was heated to reflux overnight. The solution was then cooled to room temperature and the resulting solid was isolated by filtration. The crude material was recrystallized from ethanol to yield 260 mg (78%, 10% for five steps) of the title compound. MS (m/z, ES+): 249.0 (M+1, 100%).

The following compounds were prepared in a manner analogous to the procedure described in Example 5.

4-(5-Methoxy-benzothiazol-2-yl)-5-methyl-2H-pyrazol-3-ylamine (574-7E): The title compound (16 mg) was prepared in five steps starting from 1.6 g (7.6 mmol) of 4-methoxy-2-nitroaniline. MS (m/z, ES+): 261.0 (M+1, 100%).

Example 6

Synthesis of 4-Benzothiazol-2-yl-5-methylsulfanyl-1H-pyrazol-3-ylamine

To a suspension of 2-benzothiazol-2-yl-3,3-bismethylsulfanylacrylonitrile (50 mg, 0.18 mmol) in ethanol (2 mL) was added hydrazine hydrate (15 μL). The mixture was heated to reflux for 2 hours. The reaction mixture was then cooled and water was added. The resulting precipitate was isolated by filtration to yield 21 mg (44%) of the title compound as a yellow solid. MS (m/z, ES+): 263 (M+1, 100%).

Example 7

Synthesis of 4-Benzothiazol-2-yl-1H-pyrazole-3,5-diamine

To a suspension of 2-benzothiazol-2-yl-3,3-bismethylsulfanylacrylonitrile (140 mg, 0.5 mmol) in ethanol (5 mL) was added a solution of ammonia (6 mL of a 2 N solution in ethanol, 12 mmol). The reaction was heated to 70° C. for 5 hours in a sealed reaction vessel. After cooling to room temperature, hydrazine hydrate (60 μL, 1.7 mmol) was added and the reaction was heated to reflux for 2 days. The solvent was then evaporated and the crude material was purified by flash chromatography eluting with $CHCl_3$:MeOH=9:1 to yield 0.027 g (23%) of the title compound as a pale pink powder. MS (m/z, ES+): 232 (M+1, 100%). $^1$H NMR (ppm, 300 MHz, DMSO-$d_6$): δ 10.85 (br s, 1H), 7.98 (d, $^3J$=7.8 Hz, 1H), 7.78 (d, $^3J$=8.0 Hz, 1H), 7.39 (dd, $^3J$=7.8 Hz, $^3J$=8.0 Hz, 1H), 7.23 (dd, $^3J$=7.8 Hz, $^3J$=8.0 Hz, 1H), 5.55 (br s, 4H).

Example 8

Synthesis of 4-Benzoxazol-2-yl-1H-pyrazole-3,5-diamine

The title compound (0.020 g) was prepared according to the procedure as described in Example 7 starting from 1.90 g (7.3 mmol) of 2-benzoxazol-2-yl-3,3-bismethylsulfanylacrylonitrile with the following modifications. A 300 mL of a saturated ammonium solution in ethanol was used and the reaction was refluxed for 1 hr prior to the evaporation of the solvent and purification of the resulting crude material. This intermediate was then treated with hydrazine hydrate to afford the product. MS (m/z, ES+): 216.72 (M+1, 100%). Yield=1%.

Example 9

Synthesis of 4-Benzothiazol-2-yl-$N^5$-benzyl-1H-pyrazole-3,5-diamine

A solution of 2-benzothiazol-2-yl-3,3-bismethylsulfanylacrylonitrile (200 mg, 0.73 mmol) and benzylamine (160 mg, 1.5 mmol) in 50 mL of ethanol was heated to reflux for 90 minutes. Hydrazine hydrate (35 μL, 1.0 mmol) was then added to the reaction mixture. The solution was heated to reflux until the reaction was complete as determined by TLC analysis. The reaction solution was allowed to cool to room temperature and the title compound (124 mg) was isolated by filtration, washed with ethanol and dried under high vacuum. MS (m/z, ES+): 322 (M+1, 100%); $^1$H NMR (300 MHz, ppm, DMSO-$d_6$): δ μ11.32 (br s, 1/3H), 10.89 (s, br., 2/3H), 7.98 (d, $^3J$=7.7 Hz, 1H), 7.82 (d, $^3J$=8.0 Hz, 1H), 7.41-7.28 (m, 6H), 7.22 (m, 1H), 6.15 (br s, 9/10H), 4.95 (br s, 1/10H), 4.48 (d, $^3J$=4.7 Hz, 1H). Yield=53%.

The following compounds were prepared in a manner analogous to the procedure described in Example 9.

4-Benzothiazol-2-yl-5-pyrrolidin-1-yl-1H-pyrazol-3-ylamine: The title compound (53 mg) was prepared in two steps starting from 140 mg (0.50 mmol) of 2-benzothiazol-2-yl-3,3-bis-methylsulfanylacrylonitrile and 53 mg (0.75 mmol) of pyrrolidine. MS (m/z, ES+): 286 (M+1, 100%). Yield=37%.

4-Benzothiazol-2-yl-$N^5$-ethyl-1H-pyrazole-3,5-diamine (48 mg) was prepared in two steps starting from 139 mg (0.50 mmol) of 2-benzothiazol-2-yl-3,3-bis-methylsulfanylacrylonitrile and 0.059 mL of a 70% w/w solution (0.75 mmol) of ethylamine in water. MS (m/z, ES+): 260 (M+1, 100%). Yield=37%.

4-Benzothiazol-2-yl-5-morpholin-4-yl-1H-pyrazol-3-ylamine: The title compound (46 mg) was prepared in two steps starting from 139 mg (0.50 mmol) of 2-benzothiazol-2-yl-3,3-bis-methylsulfanylacrylonitrile and 62 mg (0.75 mmol) of morpholine. MS (m/z, ES+): 302 (M+1, 100%). Yield=30%.

4-Benzothiazol-2-yl-5-(4-methylpiperazin-1-yl)-1H-pyrazol-3-ylamine: The title compound (7 mg) was prepared in two steps starting from 139 mg (0.50 mmol) of 2-benzothiazol-2-yl-3,3-bismethylsulfanylacrylonitrile and 75 mg (0.75 mmol) of 1-methylpiperazine. MS (m/z, ES+): 315 (M+1, 100%). Yield=4%.

4-Benzothiazol-2-yl-$N^5$-(3,5-dichlorophenyl)-1H-pyrazole-3,5-diamine: The title compound (30 mg) was prepared in two steps starting from 100 mg (0.36 mmol) of 2-benzothiazol-2-yl-3,3-bismethylsulfanylacrylonitrile and 117 mg (0.72 mmol) of 3,5-dichlorophenylamine. MS (m/z, ES+): 376 ($Cl^{35}Cl^{35}$M+1, 100%), 378 ($Cl^{37}Cl^{35}$M+1, 70%). Yield=22%.

4-Benzothiazol-2-yl-$N^5$-(3-trifluoromethanesulfonylphenyl)-1H-pyrazole-3,5-diamine: The title compound (9 mg) was prepared in two steps starting from 100 mg (0.36 mmol) of 2-benzothiazol-2-yl-3,3-bismethylsulfanylacrylonitrile, 81 mg (0.72 mmol) of 3-trifluoromethane-sulfonylphenylamine and 0.04 mL of triethylamine. MS (m/z, ES+): 440 (M+1, 100%). Yield=6%.

4-(5-Amino-4-benzothiazol-2-yl-2H-pyrazol-3-ylamino)-N-thiazol-2-yl-benzenesulfonamide: The title compound (20 mg) was prepared in two steps starting from 100 mg (0.36 mmol) of 2-benzothiazol-2-yl-3,3-bismethylsulfanylacrylonitrile and 93 mg (0.36 mmol) of 4-amino-N-thiazol-2-ylbenzenesulfonamide. MS (m/z, ES+): 470 (M+1, 100%). Yield=12%.

4-Benzothiazol-2-yl-$N^5$-quinolin-6-yl-1H-pyrazole-3,5-diamine: The title compound (91 mg) was prepared in two steps starting from 100 mg (0.36 mmol) of 2-benzothiazol-2-yl-3,3-bismethylsulfanylacrylonitrile and 103 mg (0.72 mmol) of 6-aminoquinoline. MS (m/z, ES+): 359 (M+1, 100%). Yield=70%.

4-Benzothiazol-2-yl-$N^3$-quinolin-5-yl-1H-pyrazole-3,5-diamine: The title compound (33 mg) was prepared in two steps starting from 100 mg (0.36 mmol) of 2-benzothiazol-2-yl-3,3-bismethylsulfanylacrylonitrile and 103 mg (0.72 mmol) of 5-aminoquinoline. MS (m/z, ES+): 359 (M+1, 100%). Yield=25%.

4-Benzothiazol-2-yl-$N^5$-pyridin-3-yl-1H-pyrazole-3,5-diamine: The title compound (69 mg) was prepared in two steps starting from 100 mg (0.36 mmol) of 2-benzothiazol-2-yl-3,3-bismethylsulfanylacrylonitrile and 68 mg (0.72 mmol) of 3-aminopyridine. MS (m/z, ES+): 309 (M+1, 100%). Yield=62%.

trans-2-(5-Amino-4-benzothiazol-2-yl-2H-pyrazol-3-ylamino)cyclopentanol: The title compound (69 mg) was prepared in two steps starting from 139 mg (0.50 mmol) of 2-benzothiazol-2-yl-3,3-bismethylsulfanylacrylonitrile and 75 mg (0.75 mmol) of trans-2-amino-cyclopentanol. MS (m/z, ES+): 316 (M+1, 100%). Yield=44%.

4-Benzothiazol-2-yl-$N^5$-pyridin-4-ylmethyl-1H-pyrazole-3,5-diamine: The title compound (32 mg) was prepared in two steps starting from 83 mg (0.30 mmol) of 2-benzothiazol-2-yl-3,3-bismethylsulfanylacrylonitrile and 64 mg (0.60 mmol) of 4-(aminomethyl)pyridine. MS (m/z, ES+): 323 (M+1, 100%). Yield=33%.

4-Benzothiazol-2-yl-$N^5$-pyridin-3-ylmethyl-1H-pyrazole-3,5-diamine (474-42B): The title compound (33 mg) was prepared in two steps starting from 83 mg (0.30 mmol) of 2-benzothiazol-2-yl-3,3-bis-methylsulfanylacrylonitrile and 64 mg (0.60 mmol) of 3-(aminomethyl)pyridine. MS (m/z, ES+): 323.1 (M+1, 100%). Yield=34%.

4-Benzothiazol-2-yl-$N^5$-(2-morpholin-4-ylethyl)-1H-pyrazole-3,5-diamine (474-42C): The title compound (40 mg) was prepared in two steps starting from 83 mg (0.30 mmol) of 2-benzothiazol-2-yl-3,3-bis-methylsulfanylacrylonitrile and 78 mg (0.60 mmol) of 2-morpholin-4-ylethylamine. MS (m/z, ES+): 345.2 (M+1, 100%). Yield=43%.

4-Benzothiazol-2-yl-$N^3$-(3-imidazol-1-ylpropyl)-1H-pyrazole-3,5-diamine (590-13-2): The title compound (69 mg) was prepared in two steps starting from 280 mg (1.0 mmol) of 2-benzothiazol-2-yl-3,3-bis-methylsulfanylacrylonitrile and 260 mg (2.1 mmol) of histamine. MS (m/z, ES+): 340.1 (M+1, 65%), 272 (M−67, 100%). Yield=43%.

4-Benzothiazol-2-yl-$N^3$-(3-dimethylaminopropyl)-1H-pyrazole-3,5-diamine (590-14): The title compound (130 mg) was prepared in two steps starting from 140 mg (0.50 mmol) of 2-benzothiazol-2-yl-3,3-bis-methylsulfanylacrylonitrile and 82 mg (0.80 mmol) of N,N-dimethylaminopropylamine. MS (m/z, ES+): 317.1 (M+1, 100%). Yield=80%.

4-Benzothiazol-2-yl-$N^3$-(2-pyrrolidin-1-ylethyl)-1H-pyrazole-3,5-diamine (590-18): The title compound (126 mg) was prepared in two steps starting from 140 mg (0.50 mmol) of 2-benzothiazol-2-yl-3,3-bis-methylsulfanylacrylonitrile and 62 mg (0.55 mmol) of 1-(2-aminoethyl)pyrrolidine. MS (m/z, ES+): 329.1 (M+1, 100%), 258.1 (M—$C_4H_8N$, 40%). Yield=88%.

4-Benzothiazol-2-yl-$N^3$-(2-methoxyethyl)-1H-pyrazole-3,5-diamine (590-27): The title compound (10 mg) was prepared in two steps starting from 100 mg (0.36 mmol) of 2-benzothiazol-2-yl-3,3-bis-methylsulfanylacrylonitrile and 30 mg (0.40 mmol) of 2-methoxyethylamine. MS (m/z, ES+): 290.1 (M+1, 100%). Yield=10%.

3-(5-Amino-4-benzothiazol-2-yl-1H-pyrazol-3-ylamino)propan-1-ol (590-28): The title compound (83 mg) was prepared in two steps starting from 100 mg (0.36 mmol) of 2-benzothiazol-2-yl-3,3-bis-methylsulfanylacrylonitrile and 30 mg (0.40 mmol) of 3-propanolamine. MS (m/z, ES+): 290.1 (M+1, 100%). Yield=80%.

4-[(5-Amino-4-benzothiazol-2-yl-1H-pyrazol-3-ylamino)-methyl]benzenesulfonamide (590-29): The title compound (35 mg) was prepared in two steps starting from 100 mg (0.37 mmol) of 2-benzothiazol-2-yl-3,3-bis-methyl-sulfanylacrylonitrile, 93 mg (0.42 mmol) of 4-(aminomethyl)benzenesulfonamide hydrochloride hydrate, and 100 mg (1.0 mmol) of triethylamine. MS (m/z, ES+): 401.1 (M+1, 100%). Yield=24%.

N-[2-(5-Amino-4-benzothiazol-2-yl-1H-pyrazol-3-ylamino)-ethyl]acetamide (590-33): The title compound (93 mg) was prepared in two steps starting from 140 mg (0.50 mmol) of 2-benzothiazol-2-yl-3,3-bis-methylsulfanylacrylonitrile and 93 mg (0.55 mmol) of N-acetylethylenediamine. MS (m/z, ES+): 317.1 (M+1, 99%), 299.1 (M−17, 100%). Yield=59%.

4-(5-Amino-4-benzothiazol-2-yl-1H-pyrazol-3-ylamino)butan-1-ol (590-44): The title compound (54 mg) was prepared in two steps starting from 100 mg (0.36 mmol) of 2-benzothiazol-2-yl-3,3-bis-methylsulfanylacrylonitrile and 40 mg (0.45 mmol) of 4-amino-1-butanol. MS (m/z, ES+): 304.1 (M+1, 100%). Yield=50%.

4-Benzothiazol-2-yl-5-piperazin-1-yl-2H-pyrazol-3-ylamine (590-58): The title compound (50 mg) was prepared in two steps starting from 75 mg (0.30 mmol) of 2-benzothiazol-2-yl-3,3-bis-methylsulfanylacrylonitrile and 28 mg (0.36 mmol) of piperazine. MS (m/z, ES+): 301.1 (M+1, 100%). Yield=55%.

4-Benzothiazol-2-yl-$N^3$-piperidin-4-ylmethyl-1H-pyrazole-3,5-diamine (610-38E): The title compound (14 mg) was prepared in two steps starting from 100 mg (0.36 mmol) of 2-benzothiazol-2-yl-3,3-bis-methylsulfanylacrylonitrile and 47 mg (0.41 mmol) of 4-aminomethylpiperidine. MS (m/z, ES+): 329.2 (M+1, 25%), 244.1 (M−84, 45%), 232.1 (M−96, 100%). Yield=12%.

4-(5-Amino-4-benzothiazol-2-yl-1H-pyrazol-3-ylamino)butyric acid (523-29-B): The title compound (50 mg) was prepared in two steps starting from 530 mg (2.0 mmol) of 2-benzothiazol-2-yl-3,3-bis-methylsulfanylacrylonitrile, 250 mg (2.3 mmol) of 4-aminobutyric acid and 0.6 mL of triethylamine. MS (m/z, ES+): 318.1 (M+1, 100%), 300.1 (M-H2O, 95%); $^1$H NMR (300 MHz, ppm, DMSO-$d_6$): δ 11.5 (br s, 2H), 7.8 (d, 1H), 7.7 (d, 1H), 7.4 (d, 1H), 7.2 (d, 1H), 6.0 (br s, 1H), 5.5 (br s, 2H), 3.2 (m, 2H), 2.3 (t, 2H), 1.8 (m, 2H). Yield=8%.

4-Benzothiazol-2-yl-N3-[2-(1H-imidazol-4-yl)-ethyl]-1H-pyrazole-3,5-diamine (523-31C): The title compound (310 mg) was prepared in two steps starting from 530 mg (2.0 mmol) of 2-benzothiazol-2-yl-3,3-bis-methylsulfanylacrylonitrile, 500 mg (4.5 mmol) of histamine and 0.6 mL of triethylamine. MS (m/z, ES+): 326.09 (M+1, 100%). Yield=48%.

2-(5-Amino-4-benzothiazol-2-yl-1H-pyrazol-3-ylamino)-ethanol (523-34A): The title compound (140 mg) was prepared in two steps starting from 530 mg (2.0 mmol) of 2-benzothiazol-2-yl-3,3-bis-methylsulfanylacrylonitrile, 500 mg (8.0 mmol) of monoethanolamine and 0.5 mL of triethylamine. MS (m/z, ES+): 276.02 (100%, M+1). Yield=25%.

4-[2-(5-Amino-4-benzothiazol-2-yl-1H-pyrazol-3-ylamino)-ethyl]-phenol (523-36): The title compound (210 mg) was prepared in two steps starting from 530 mg (2.0 mmol) of 2-benzothiazol-2-yl-3,3-bis-methylsulfanylacrylonitrile, 0.60 g (4.4 mmol) of 4-(2-aminoethyl)-phenol and 0.6 mL of triethylamine. MS (m/z, ES+): 352.05 (M+1, 100%). Yield=30%.

4-Benzothiazol-2-yl-$N^3$-(3-methylbutyl)-1H-pyrazole-3,5-diamine (523-27A): The title compound (150 mg) was prepared in two steps starting from 530 mg (2.0 mmol) of 2-benzothiazol-2-yl-3,3-bis-methylsulfanylacrylonitrile, 220 mg (3.0 mmol) of N,N-dimethylaminoethylendiamine and 0.6 mL of triethylamine. MS (m/z, ES+): 303.2 (M+1, 100%). Yield=25%.

4-Benzothiazol-2-yl-$N^3$-[2-(1H-indol-3-yl)-ethyl]-1H-pyrazole-3,5-diamine (590-37): The title compound (45 mg) was prepared in two steps starting from 100 mg (0.36 mmol)

of 2-benzothiazol-2-yl-3,3-bis-methylsulfanylacrylonitrile and 62 mg (0.39 mmol) of tryptamine. MS (m/z, ES+): 375.1 (M+1, 100%). Yield=49%.

4-(5-Fluoro-6-methoxybenzothiazol-2-yl)-$N^3$-[2-(3H-imidazol-4-yl)-ethyl]-1H-pyrazole-3,5-diamine (597-33A): The title compound (35 mg) was prepared in two steps starting from 80 mg (0.25 mmol) of 2-(5-fluoro-6-methoxybenzothiazole)-3,3-bis-methylsulfanylacrylonitrile and 30 mg (0.27 mmol) of histamine. MS (m/z, ES+): 374.1 (M+1, 100%). Yield=35%.

N-{2-[5-Amino-4-(5-fluoro-6-methoxybenzothiazole)-1H-pyrazol-3-ylamino]-ethyl}acetamide (597-35): The title compound (200 mg) was prepared in two steps starting from 350 mg (1.1 mmol) of 2-(5-fluoro-6-methoxybenzothiazole)-3,3-bis-methylsulfanylacrylonitrile and 140 µL, (1.3 mmol) of N-acetylethylenediamine. MS (m/z, ES+): 365.1 (M+1, 100%). Yield=51%.

4-(5-Fluoro-6-methoxybenzothiazole)-5-piperizin-1-yl-2H-pyrazol-3-ylamine (597-36): The title compound (20 mg) was prepared in two steps starting from 120 mg (0.37 mmol) of 2-(5-fluoro-6-methoxybenzothiazole)-3,3-bis-methylsulfanylacrylonitrile and 40 mg (0.46 mmol) of piperizine. MS (m/z, ES+): 349.1 (M+1, 100%). Yield=16%.

$N^3$-(2-Dimethylaminoethyl)-4-(5-fluoro-6-methoxybenzothiazole)-1H-pyrazole-3,5-diamine (597-40A): The title compound (35 mg) was prepared in two steps starting from 100 mg (0.31 mmol) of 2-(5-fluoro-6-methoxybenzothiazole)-3,3-bis-methylsulfanylacrylonitrile and 40 µL (0.36 mmol) of N,N-dimethylethylenediamine. MS (m/z, ES+): 351.1 (M+1, 100%). Yield=33%.

$N^3$-(3-Dimethylaminopropyl)-4-(5-fluoro-6-methoxybenzothiazole)-1H-pyrazole-3,5-diamine (597-40B): The title compound (40 mg) was prepared in two steps starting from 100 mg (0.31 mmol) of 2-(5-fluoro-6-methoxybenzothiazole)-3,3-bis-methylsulfanylacrylonitrile and 46 µL (0.37 mmol) of 3-(dimethylamino)propylamine. MS (m/z, ES+): 365.1 (M+1, 100%). Yield=35%.

3-[5-Amino-4-(5-fluoro-6-methoxybenzothiazol-2-yl)-1H-pyrazol-3-ylamino]-propanol (597-45): The title compound (72 mg) was prepared in two steps starting from 100 mg (0.31 mmol) of 2-(5-fluoro-6-methoxybenzothiazole)-3,3-bis-methylsulfanylacrylonitrile and 30 µL (0.39 mmol) of 3-aminopropanol. MS (m/z, ES+): 338.3 (M+1, 100%). Yield=70%.

$N^3$-[2-(3H-Imidazol-4-yl)-ethyl]-4-(6-methoxybenzothiazol-2-yl)-1H-pyrazole-3,5-diamine (597-42): The title compound (72 mg) was prepared in two steps starting from 100 mg (0.32 mmol) of 2-(6-methoxybenzothiazole)-3,3-bis-methylsulfanylacrylonitrile and 36 mg (0.32 mmol) of histamine. MS (m/z, ES+): 356.1 (M+1, 100%). Yield=28%.

4-(6-Methoxybenzothiazole)-5-piperizin-1-yl-2H-pyrazol-3-ylamine (597-43): The title compound (39 mg) was prepared in two steps starting from 100 mg (0.32 mmol) of 2-(6-methoxybenzothiazole)-3,3-bis-methylsulfanylacrylonitrile and 28 mg (0.33 mmol) of piperizine. MS (m/z, ES+): 331.1 (M+1, 100%). Yield=36%.

Example 10

Synthesis of $N^3$-(4-Amino-phenyl)-4-benzothiazol-2-yl-1H-pyrazole-3,5-diamine (590-24)

1. A mixture of 2-benzothiazol-2-yl-3,3-bis-methylsulfanyl-acrylonitrile (140 mg, 0.50 mmol) and 4'-acetylaminoaniline (90 mg, 0.60 mmol) in ethanol (5 mL) was refluxed for 3 hrs. A yellow solid formed upon cooling of the reaction mixture. The resulting precipitate was isolated by filtration and was washed with ethanol to yield 150 mg (78%) of N-[4-(2-benzothiazol-2-yl-2-cyano-1-methylsulfanylvinylamino)phenyl]acetamide. MS (m/z, ES+): 381.1 (M+1, 100%).

2. The product from the above reaction (150 mg, 0.39 mmol) and hydrazine hydrate (50 mg, 1.0 mmol) in ethanol (5 mL) were heated to reflux overnight. Upon evaporation of approximately half of the solvent, a solid formed. The solid was isolated by filtration and was washed with ethanol to yield 33 mg (23%) of N-[4-(5-amino-4-benzothiazol-2-yl-1H-pyrazol-3-ylamino)phenyl]acetamide. MS (m/z, ES+): 365.1 (M+1, 100%). The mother liquor was concentrated to yield an additional 110 mg of the crude product as a red solid.

3. The crude product isolated above (110 mg, 0.3 mmol) was refluxed in a mixture of ethanol (10 mL) and concentrated HCl (5 mL) for 1 hr. A yellow solid formed upon cooling. The solid was isolated by filtration and was washed with ethanol. The resulting hydrochloride salt (51 mg) was dissolved in water (10 mL) and adjusted to neutral pH by the addition of dilute NaOH solution. The product was extracted into ethyl acetate, the combined extracts were washed with brine, dried over anhydrous sodium sulfate, filtered and evaporated to yield 26 mg (27%) of the title compound as a cream coloured solid. MS (m/z, ES+): 323.1 (M+1, 100%).

The following compounds were prepared in a manner analogous to the procedure described in Example 10.

$N^3$-(2-Aminoethyl)-4-benzothiazol-2-yl-1H-pyrazole-3,5-diamine (590-46): The title compound (43 mg) was prepared in three steps starting from 140 mg (0.50 mmol) of 2-benzothiazol-2-yl-3,3-bis-methylsulfanylacrylonitrile and 65 mg (0.55 mmol) of N-acetylethylenediamine. MS (m/z, ES+): 275.1 (M+1, 100%). Yield=54%.

Example 11

4-Benzothiazol-2-yl-$N^3$-(2-ethylaminoethyl)-1H-pyrazole-3,5-diamine (590-73)

1. A mixture of 2-benzothiazol-2-yl-3,3-bis-methylsulfanylacrylonitrile (200 mg, 0.74 mmol) and N-acetylethylenediamine (83 mg, 0.81 mmol) in ethanol (10 mL) was refluxed for 90 min. To this solution was added hydrazine hydrate (61 mg, 1.2 mmol), and the resulting mixture was refluxed overnight. Solids formed upon cooling. The resulting crystals were filtered and washed with ethanol to yield 150 mg (66%) of N-[2-(5-amino-4-benzothiazol-2-yl-1H-pyrazol-3-ylamino)ethyl]acetamide. MS (ES+): 317.1 (M+1, 100%).

2. N-[2-(5-Amino-4-benzothiazol-2-yl-1H-pyrazol-3-ylamino)ethyl]acetamide (80 mg, 0.25 mmol) and lithium aluminum hydride (92 mg) were refluxed in anhydrous THF (10 mL) for 3 hrs. The resulting mixture was poured into a saturated ammonium chloride solution (50 mL). The aqueous phase was extracted with ethyl acetate (3×50 mL). The combined extracts were washed with brine, dried over anhydrous sodium sulfate, filtered and evaporated to yield 54 mg of crude product. The crude product was purified by flash column chromatography eluting with $CH_2Cl_2$:MeOH=5:1 with 0.5% $NH_3$. The title compound was isolated in a yield of 36 mg (48%). MS (m/z, ES+): 303.1 (M+1, 100%).

Example 12

Synthesis of 2-(5-Amino-3-methyl-1H-pyrazol-4-yl)-benzothiazole-6-sulfonic acid (2-hydroxyethyl)-amide (474-86D)

1. The starting material 4-benzothiazol-2-yl-5-methyl-2H-pyrazol-3-ylamine (500 mg, 2.2 mmol) was slowly added to neat chlorosulfonic acid (2.5 mL) which had been cooled in an ice bath. The solution was heated at 150° C. for 5 hrs. The reaction mixture was then poured over ice and the resulting solids were isolated by filtration. The solids were dried to yield 770 mg of the crude product as a 3:1 mixture of 2-(5-amino-3-methyl-1H-pyrazol-4-yl)benzothiazole-6-sulfonic acid and 2-(5-amino-3-methyl-1H-pyrazol-4-yl)benzothiazole-4-sulfonyl chloride. The crude product was used in the next step without further purification.

2. The crude product (130 mg, 0.39 mmol) from the preparation of 2-(5-amino-3-methyl-1H-pyrazol-4-yl)benzothiazole-6-sulfonyl chloride was suspended in chloroform. Triethylamine (0.1 mL) and 2-aminoethanol (26 mg, 0.43 mmol) were then added. The reaction mixture was stirred at room temperature overnight. The solvent was evaporated and the product was purified using preparative TLC eluting with EtOAc:hexanes:MeOH=6/4/0.3 to yield 22 mg (16%) of the product as a cream coloured powder. MS (m/z, ES+): 354 (M+1, 100%); $^1$H NMR (400 MHz, ppm, DMSO-d$_6$): δ 12.25-11.75 (br s, 1H, exchangeable), 8.47 (s, 1H), 7.99 (d, J=8.5 Hz, 1H), 7.81 (d, J=8.5 Hz, 1H), 7.59 (br s, 1H, SO$_2$NH, exchangeable), 7-5.5 (br s, 2H, exchangeable), 4.66 (t, J=5.6 Hz, 1H, OH, exchangeable), 3.34 (m, J=6.2 Hz, 2H), 2.80 (br s, 2H), 2.41 (s, 3H).

The following compounds were prepared in a manner analogous to the procedure described in Example 12.

5-Methyl-4-[6-(4-methylpiperazine-1-sulfonyl)-benzothiazol-2-yl]-2H-pyrazol-3-ylamine (474-86F): the title compound (30 mg) was prepared from crude 2-(5-amino-3-methyl-1H-pyrazol-4-yl)-benzothiazole-6-sulfonyl chloride (128 mg, 0.39 mmol), 4-methylpiperazine (39 mg, 0.43 mmol) and triethylamine (0.1 mL). MS (m/z, ES+): 393.1 (M+1, 100%). Yield=20%.

2-(5-Amino-3-methyl-1H-pyrazol-4-yl)-benzothiazole-6-sulfonic acid (2-methoxyethyl)-amide (551-8): the title compound (33 mg) was prepared from crude 2-(5-amino-3-methyl-1H-pyrazol-4-yl)-benzothiazole-6-sulfonyl chloride (75 mg, 0.23 mmol), 2-methoxyethylamine (39 mg, 0.43 mmol) and the polystyrene resin bound base N-3-(morpholino)propyl polystyrene sulfonamide (PS-NMM) (0.24 g, 0.45 mmol) in 4 mL of methanol. MS (m/z, ES+): 368.5 (M+1, 100%); $^1$H NMR (500 MHz, ppm, DMSO-d$_6$): δ 11.8-12.1 (br s, 1H), 8.5 (s, 1H), 7.99 (br d, 1H), 7.83 (d, 1H), 7.73 (t, 1H), 5.9-6.7 (br s, 3H), 3.30 (t, 2H), 3.15 (s, 3H), 2.94 (dt, 2H), 2.41 (br s, 3H). Yield=46%.

2-(5-Amino-3-methyl-1H-pyrazol-4-yl)-benzothiazole-6-sulfonic acid 4-fluoro-benzylamide (551-9): the title compound (8 mg) was prepared from crude 2-(5-amino-3-methyl-1H-pyrazol-4-yl)-benzothiazole-6-sulfonyl chloride (75 mg, 0.23 mmol), 4-fluorobenzylamine (29 μL, 0.25 mmol) and PS-NMM (0.22 g, 0.45 mmol) in 4 mL of chloroform. MS (m/z, ES+): 418.3 (M+1, 100%). Yield=9%.

2-(5-Amino-3-methyl-1H-pyrazol-4-yl)-benzothiazole-6-sulfonic acid (2-thiophen-2-ylethyl)-amide (551-10): the title compound (8 mg) was prepared from crude 2-(5-amino-3-methyl-1H-pyrazol-4-yl)-benzothiazole-6-sulfonyl chloride (75 mg, 0.23 mmol), 2-thiophen-2-ylethylamine (29 μL, 0.25 mmol) and PS-NMM (0.22 g, 0.45 mmol) in 4 mL of chloroform. MS (m/z, ES+): 420.4 (M+1, 100): $^1$H NMR (500 MHz, ppm, DMSO-d$_6$): δ 11.8-12.2 (br s, 1H), 8.5 (s, 1H), 8.0 (d, 1H), 7.8 (m, 2H), 7.32 (d, 1H), 6.93 (dd, 1H), 6.86 (d, 1H), 6.0 (br s, 2H), 3.03 (q, 2H), 2.92 (t, 2H), 2.43 (br s, 3H). Yield=8%.

2-(5-Amino-3-methyl-1H-pyrazol-4-yl)-benzothiazole-6-sulfonic acid 4-chlorobenzylamide (551-11B): the title compound (21 mg) was prepared from crude 2-(5-amino-3-methyl-1H-pyrazol-4-yl)-benzothiazole-6-sulfonyl chloride (100 mg, 0.30 mmol), 4-chlorobenzylamine (74 μL, 0.60 mmol) and PS-NMM (0.320 g, 0.60 mmol) in 5 mL of methanol. MS (m/z, ES+): 434.4 (Cl$^{35}$ M+1, 100%), 436.4 (Cl$^{37}$ M+1, 40%). Yield=16%.

2-(5-Amino-3-methyl-1H-pyrazol-4-yl)-benzothiazole-6-sulfonic acid 4-methoxybenzylamide (551-12B): the title compound (15 mg) was prepared from crude 2-(5-amino-3-methyl-1H-pyrazol-4-yl)-benzothiazole-6-sulfonyl chloride (100 mg, 0.30 mmol), 4-methoxybenzylamine (79 μL, 0.60 mmol) and PS-NMM (0.320 g, 0.60 mmol) in 5 mL of methanol. MS (m/z, ES+): 430.5 (M+1, 100%). Yield=11%.

2-(5-Amino-3-methyl-1H-pyrazol-4-yl)-benzothiazole-6-sulfonic acid benzylamide (551-13B): the title compound (16 mg) was prepared from crude 2-(5-amino-3-methyl-1H-pyrazol-4-yl)-benzothiazole-6-sulfonyl chloride (100 mg, 0.30 mmol), benzylamine (66 μL, 0.60 mmol) and PS-NMM (0.320 g, 0.60 mmol) in 5 mL of methanol. MS (m/z, ES+): 400.5 (M+1, 100%). Yield=13%.

2-(5-Amino-3-methyl-1H-pyrazol-4-yl)-benzothiazole-6-sulfonic acid phenethylamide (551-14B): the title compound (9 mg) was prepared from crude 2-(5-amino-3-methyl-1H-pyrazol-4-yl)-benzothiazole-6-sulfonyl chloride (100 mg, 0.30 mmol), phenethylamine (76 μL, 0.60 mmol) and PS-NMM (0.320 g, 0.60 mmol) in 5 mL of methanol. MS (m/z, ES+): 414.5 (M+1, 100%). Yield=7%.

2-(5-Amino-3-methyl-1H-pyrazol-4-yl)-benzothiazole-6-sulfonic acid [2-(4-aminophenyl)-ethyl]-amide (551-15B): the title compound (25 mg) was prepared from crude 2-(5-amino-3-methyl-1H-pyrazol-4-yl)-benzothiazole-6-sulfonyl chloride (100 mg, 0.30 mmol), phenethylamine (80 μL, 0.60 mmol) and PS-NMM (0.320 g, 0.60 mmol) in 5 mL of methanol. MS (m/z, ES+): 429.5 (M+1, 100%). Yield=19%.

2-(5-Amino-3-methyl-1H-pyrazol-4-yl)-benzothiazole-6-sulfonic acid (2-morpholin-4-ylethyl)-amide (551-16): the title compound (56 mg) was prepared from crude 2-(5-amino-3-methyl-1H-pyrazol-4-yl)-benzothiazole-6-sulfonyl chloride (100 mg, 0.30 mmol), 2-morpholin-4-ylethylamine (80 μL, 0.60 mmol) and PS-NMM (0.320 g, 0.60 mmol) in 5 mL of methanol. MS (m/z, ES+): 423.5 (M+1, 100%). Yield=43%.

2-(5-Amino-3-methyl-1H-pyrazol-4-yl)-benzothiazole-6-sulfonic acid (2,2,2-trifluoroethyl)-amide (551-17B): the title compound (11 mg) was prepared from crude 2-(5-amino-3-methyl-1H-pyrazol-4-yl)-benzothiazole-6-sulfonyl chloride (100 mg, 0.30 mmol), 2,2,2-trifluoroethylamine (48 μL, 0.60 mmol) and PS-NMM (0.320 g, 0.60 mmol) in 5 mL of methanol. MS (m/z, ES+): 392.4 (M+1, 100%). Yield=9%.

2-(5-Amino-3-methyl-1H-pyrazol-4-yl)-benzothiazole-6-sulfonic acid cyclopropylmethylamide (551-18B): the title compound (27 mg) was prepared from crude 2-(5-amino-3-methyl-1H-pyrazol-4-yl)-benzothiazole-6-sulfonyl chloride (100 mg, 0.30 mmol), C-cyclopropylmethylamine (53 μL, 0.60 mmol) and PS-NMM (0.320 g, 0.60 mmol) in 5 mL of methanol. MS (m/z, ES+): 364.5 (M+1, 100%). Yield=21%.

2-(5-Amino-3-methyl-1H-pyrazol-4-yl)-benzothiazole-6-sulfonic acid [2-(3H-imidazol-4-yl)-ethyl]-amide (551-19B): the title compound (8 mg) was prepared from crude 2-(5-amino-3-methyl-1H-pyrazol-4-yl)-benzothiazole-6-sulfonyl chloride (100 mg, 0.30 mmol), 2-(3H-imidazol-4-yl)-ethylamine (68 mg, 0.60 mmol) and PS-NMM (0.320 g, 0.60 mmol) in 5 mL of methanol. MS (m/z, ES+): 404.3 (M+1, 100%). Yield=6%.

2-(5-Amino-3-methyl-1H-pyrazol-4-yl)-benzothiazole-6-sulfonic acid 4-aminobenzylamide (551-20): the title compound (15 mg) was prepared from crude 2-(5-amino-3-methyl-1H-pyrazol-4-yl)-benzothiazole-6-sulfonyl chloride (100 mg, 0.30 mmol), 4-aminomethylphenylamine (69 μL, 0.60 mmol) and PS-NMM (0.320 g, 0.60 mmol) in 5 mL of methanol. MS (m/z, ES+): 415.4 (M+1, 100%). Yield=12%.

2-(5-Amino-3-methyl-1H-pyrazol-4-yl)-benzothiazole-6-sulfonic acid (pyridin-4-ylmethyl)-amide (551-21): the title compound (13 mg) was prepared from crude 2-(5-amino-3-methyl-1H-pyrazol-4-yl)-benzothiazole-6-sulfonyl chloride (100 mg, 0.30 mmol), C-pyridin-4-ylmethylamine (62 µL, 0.60 mmol) and PS-NMM (0.320 g, 0.60 mmol) in 5 mL of methanol. MS (m/z, ES+): 401.3 (M+1, 100%). Yield=11%.

2-(5-Amino-3-methyl-1H-pyrazol-4-yl)-benzothiazole-6-sulfonic acid (3-dimethylamino-propyl)-amide (551-22C): the title compound (2 mg) was prepared from crude 2-(5-amino-3-methyl-1H-pyrazol-4-yl)benzothiazole-6-sulfonyl chloride (100 mg, 0.30 mmol), $N^1,N^1$-dimethylpropane-1,3-diamine (77 µL, 0.60 mmol) and PS-NMM (0.320 g, 0.60 mmol) in 5 mL of methanol. MS (m/z, ES+): 395.3 (M+1, 100%). Yield=2%.

2-(5-Amino-3-methyl-1H-pyrazol-4-yl)-benzothiazole-6-sulfonic acid (acetic hydrazido) amide (551-23A): the title compound (13 mg) was prepared from crude 2-(5-amino-3-methyl-1H-pyrazol-4-yl)-benzothiazole-6-sulfonyl chloride (100 mg, 0.30 mmol), acetic acid hydrazide (45 mg, 0.60 mmol) and PS-NMM (0.320 g, 0.60 mmol) in 5 mL of methanol. MS (m/z, ES+): 367.3 (M+1, 100%). Yield=12%.

2-(5-Amino-3-methyl-1H-pyrazol-4-yl)-benzothiazole-6-sulfonic acid (2-dimethylamino-ethyl)-amide (551-24D): the title compound (11 mg) was prepared from crude 2-(5-amino-3-methyl-1H-pyrazol-4-yl)-benzothiazole-6-sulfonyl chloride (100 mg, 0.30 mmol), $N^1,N^1$-dimethylethane-1,2-diamine (67 µL, 0.60 mmol) and PS-NMM (0.320 g, 0.60 mmol) in 5 mL of methanol. MS (m/z, ES+): 381.4 (M+1, 50%). Yield=9%.

N-{2-[2-(5-Amino-3-methyl-1H-pyrazol-4-yl)-benzothiazole-6-sulfonylamino]-ethyl}-acetamide (551-25B): the title compound (52 mg) was prepared from crude 2-(5-amino-3-methyl-1H-pyrazol-4-yl)-benzothiazole-6-sulfonyl chloride (100 mg, 0.30 mmol), N-(2-aminoethyl)-acetamide (58 µL, 0.60 mmol) and PS-NMM (0.320 g, 0.60 mmol) in 5 mL of methanol. MS (m/z, ES+): 395.6 (M+1, 100%). Yield=43%.

2-(5-Amino-3-methyl-1H-pyrazol-4-yl)-benzothiazole-6-sulfonic acid (phenylhydrazino) amide (551-26B): the title compound (32 mg) was prepared from crude 2-(5-amino-3-methyl-1H-pyrazol-4-yl)-benzothiazole-6-sulfonyl chloride (100 mg, 0.30 mmol), phenylhydrazine (66 µL, 0.60 mmol) and PS-NMM (0.320 g, 0.60 mmol) in 5 mL of methanol. MS (m/z, ES+): 401.4 (M+1, 100%). Yield=26%.

2-(5-Amino-3-methyl-1H-pyrazol-4-yl)-5-fluoro-benzothiazole-6-sulfonic acid amide (574-14): The title compound (30 mg) was prepared in two steps from crude 2-(5-amino-3-methyl-1H-pyrazol-4-yl)-5-fluorobenzothiazole-6-sulfonic acid, which had been derived from the chlorosulfonation of 90 mg of 4-(5-fluorobenzothiazol-2-yl)-5-methyl-2H-pyrazol-3-ylamine, and a solution of excess ammonia dissolved in ethanol. MS (m/z, ES+): 328.0 (M+1, 100%). Yield=25%.

2-(5-Amino-3-methyl-1H-pyrazol-4-yl)-5-fluorobenzothiazole-6-sulfonic acid (2-hydroxy-ethyl)-amide (574-22A) and 2-(5-Amino-3-methyl-1H-pyrazol-4-yl)-5-fluorobenzothiazole-4-sulfonic acid (2-hydroxy-ethyl)-amide (574-22AA): The title compounds were prepared in two steps from crude 2-(5-amino-3-methyl-1H-pyrazol-4-yl)-5-fluorobenzothiazole-6-sulfonyl chloride, which had been derived from the chlorosulfonation of 50 mg of 4-(5-fluorobenzothiazol-2-yl)-5-methyl-2H-pyrazol-3-ylamine, 183 mg (0.30 mmol) of ethanolamine and triethylamine (0.50 mL) in chloroform. The crude material was purified by flash column chromatography eluting with $CHCl_3$:MeOH=9:1 to yield 12 mg (21%) of 2-(5-amino-3-methyl-1H-pyrazol-4-yl)-5-fluorobenzothiazole-6-sulfonic acid (2-hydroxy-ethyl)-amide. MS (m/z, ES+): 372.0 (M+1, 100%). 2-(5-amino-3-methyl-1H-pyrazol-4-yl)-5-fluorobenzothiazole-4-sulfonic acid (2-hydroxy-ethyl)-amide was isolated in a yield of 1 mg (2%). MS (m/z, ES+): 372.0 (M+1, 100%).

2-(5-Amino-3-methyl-1H-pyrazol-4-yl)-5-fluoro-benzothiazole-6-sulfonic acid (pyridin-4-ylmethyl)-amide (574-22B): The title compound (15 mg) was prepared from crude 2-(5-amino-3-methyl-1H-pyrazol-4-yl)-5-fluorobenzothiazole-6-sulfonyl chloride, which had been derived from the chlorosulfonation of 90 mg of 4-(5-fluorobenzothiazol-2-yl)-5-methyl-2H-pyrazol-3-ylamine, 32 mg (0.30 mmol) of C-pyridin-4-ylmethylamine, and triethylamine (0.50 mL) in chloroform. MS (m/z, ES+): 419.1 (M+1, 100%), 210.0 (100%). Yield=24%.

2-(5-Amino-3-methyl-1H-pyrazol-4-yl)-4-fluorobenzothiazole-6-sulfonic acid amide (598-49): The title compound (280 mg) was prepared from crude 2-(5-amino-3-methyl-1H-pyrazol-4-yl)-4-fluorobenzothiazole-7-sulfonyl chloride, which had been derived from the chlorosulfonation of 320 mg of 4-(4-fluorobenzothiazol-2-yl)-5-methyl-2H-pyrazol-3-ylamine, and a solution of excess ammonia dissolved in ethanol. MS (m/z, ES+): 328.0 (M+1, 100%). Yield=72%.

Example 13

Synthesis of
4-Benzothiazol-2-yl-5-phenyl-1H-pyrazol-3-ylamine

To a solution of 2-benzothiazol-2-yl-3,3-bismethylsulfanylacrylonitrile (278 mg, 1 mmol) in anhydrous THF (40 mL) was added phenylmagnesiumbromide (1 mmol) which was prepared from bromobenzene (152 mg, 1 mmol) and magnesium (25 mg, 1 mmol) in 10 mL of anhydrous THF. The mixture was stirred at room temperature for 60 minutes and then at 50° C. for 60 minutes. The resulting mixture was poured into a saturated ammonium chloride solution. The aqueous phase was extracted with ethyl acetate. The extract was washed, dried over magnesium sulfate, and evaporated. The residue was purified by flash chromatography eluting with hexanes:EtOAc=1:0-4:1 to yield 50 mg (16%) of the desired compound. MS (m/z, ES+): 309 (M+1, 100%).

The mixture of above prepared intermediate (50 mg, 0.16 mmol) and hydrazine hydrate (20 mg, 0.4 mmol) was refluxed in ethanol for 6 hours. The solvent was evaporated, and the resulting residue was purified by flash chromatography eluting with $CH_2Cl_2$:MeOH=1:0-9:1 to yield a yellow solid. The solid was stirred in diethyl ether and an insoluble material was removed by filtration. The ether phase was concentrated to yield 25 mg (53%) of the title compound as a yellow solid. MS (m/z, ES+): 293 (M+1, 100%).

Example 14

Synthesis of 4-Benzothiazol-2-yl-5-cyclopropyl-1H-pyrazol-3-ylamine

4-Benzothiazol-2-yl-5-cyclopropyl-1H-pyrazol-3-ylamine (23 mg) was prepared using the procedure as described in Example 13 starting from 556 mg (2.0 mmol) of 2-benzothiazol-2-yl-3,3-bismethylsulfanylacrylonitrile. Cyclopropylmagnesium bromide, which was prepared from cyclopropyl bromide (484 mg, 4 mmol) and magnesium (100 mg, 4 mmol) in 8 mL of anhydrous THF was added until the starting material had been consumed as determined by TLC. The title compound was isolated in a yield of 5%. MS (m/z, ES+): 257 (M+1, 100%).

Example 15

Synthesis of 4-Benzothiazol-2-yl-5-pyridin-3-yl-1H-pyrazol-3-ylamine

1. A yellow suspension of 3-pyridinyl lithium in THF was prepared according to the literature (Cama, L. D.; Wildonger, K. J.; Guthikonda, R.; Ratcliffe, R. W.; Christensen, B. G. *Tetrahedron* (1983), 39, 2531) by adding n-BuLi (0.25 mL of a 2 M solution in cyclohexane, 0.5 mmol) to a solution of 3-bromopyridine (87 mg, 0.5 mmol) in anhydrous ether (3 mL) at −78° C. To this slurry was rapidly added 2-benzothiazol-2-yl-3,3-bismethylsulfanylacrylonitrile (140 mg, 0.5 mmol) in anhydrous THF (5 mL) under argon. The resulting mixture was stirred at −78° C. for 1 hour, and then slowly warmed up to room temperature and stirred at that temperature for 2 hours. Upon completion of the reaction, the mixture was poured into a saturated $NH_4Cl$ aqueous solution. The aqueous phase was extracted with ethyl acetate. The organic phase was washed with brine, dried over magnesium sulfate, filtered and evaporated. The crude material was then purified by flash chromatography eluting with $CH_2Cl_2$:MeOH=1:0-19:1 to yield 100 mg (65%) of the desired product as a brown oil. MS (m/z, ES+): 310 (M+1, 25%), 263 (M−46, 100%).

2. The mixture of the above intermediate (100 mg, 0.32 mmol) and hydrazine hydrate (25 mg, 0.5 mmol) was heated at 70° C. in EtOH (10 mL) for 4 hours. The mixture was poured into a saturated $NH_4Cl$ aqueous solution. The aqueous phase was extracted with ethyl acetate. The resulting brown oil was purified by preparative TLC twice eluting with $CH_2Cl_2$:MeOH=1:10 to yield 21 mg (22%) of the title compound as a cream coloured solid. MS (m/z, ES+): 294 (M+1, 100%).

The following compounds were prepared in a manner analogous to the procedure described in Example 15.

4-Benzothiazol-2-yl-5-pyridin-4-yl-2H-pyrazol-3-ylamine (549-68B): The title compound (90 mg) was prepared in two steps starting from 560 mg (2.0 mmol) of 2-benzothiazol-2-yl-3,3-bis-methylsulfanyl-acrylonitrile and 390 mg (2.0 mmol) 4-bromopyridine hydrochloride. MS (m/z, ES+): 294.08 (M+1, 100%). Yield=15%.

Example 16

Synthesis of 4-Benzothiazol-2-yl-5-(4-nitrophenyl)-2H-pyrazol-3-ylamine

1. To a solution of benzothazole-2-acetonitrile (1.74 g, 10 mmol) in anhydrous dichloromethane (50 mL) was added triethylamine (1.95 g, 11 mmol) and 4-nitrobenzoyl chloride (1.88 g, 10 mmol) in anhydrous dichloromethane (20 mL) at room temperature. The resulting mixture was stirred at room temperature for 3 hrs. To the resulting suspension was added methanol (0.5 mL) and glacial acetic acid (0.5 mL). The resulting yellow solid was isolated by filtration and dried to yield 1.93 g (60%) of 2-benzothiazol-2-yl-3-hydroxy-3-(4-nitrophenyl)-acrylonitrile. MS (m/z, ES+): 324.0 (M+1, 100%).

2. The above prepared 2-benzothiazol-2-yl-3-hydroxy-3-(4-nitrophenyl)-acrylonitrile (500 mg, 1.55 mmol) was suspended in $POCl_3$ (12 mL). The suspension was heated at 100° C. for 4 hrs and was then poured into ice water (25 mL). The pH of the aqueous phase was adjusted to neutral. The solids were isolated by filtration and dried to yield 505 mg (95%) of 2-benzothiazol-2-yl-3-chloro-3-(4-nitrophenyl)-acrylonitrile. MS (m/z, ES+): 341.92 ($Cl^{35}$M+1, 100%), 343.92 ($Cl^{37}$M+1, 45%).

3. The 2-benzothiazol-2-yl-3-chloro-3-(4-nitrophenyl)-acrylonitrile (500 mg, 1.46 mmol) prepared above and hydrazine hydrate (150 mg, 3 mmol) were refluxed in ethanol (15 mL) for 6 hrs. The solvent was evaporated and the residue was purified by flash column chromatography eluting with $CH_2Cl_2$:MeOH=9:1 to yield 182 mg (37%) of the title compound as a yellow solid. MS (m/z, ES+): 338.04 (M+1, 100%).

The following compounds were prepared in a manner analogous to the procedure described in Example 16.

4-(5-Fluoro-6-methoxybenzothiazol-2-yl)-5-pyridin-4-yl-2H-pyrazol-3-ylamine (597-34): The title compound (260 mg) was prepared in three steps starting from 700 mg (3.15 mmol) of (5-fluoro-6-methoxy-benzothiazol-2-yl)-acetonitrile, 1.10 g (6.20 mmol) of isonicotinylchloride hydrochloride, 1.7 mL (12.2 mmol) of triethylamine and a catalytic amount of DMAP. MS (m/z, ES+): 342.1 (M+1, 100%). Yield=20%.

2-(5-Amino-3-pyridin-4-yl-1H-pyrazol-4-yl)-benzothiazole-6-sulfonic acid amide (590-62): The title compound (5 mg) was prepared in three steps starting from 102 mg (0.40 mmol) of 2-cyanomethylbenzothiazole-6-sulfonic acid amide, 70 mg (0.40 mmol) of isonicotinylchloride hydrochloride and 228 mL (1.6 mmol) of triethylamine. MS (m/z, ES+): 373.0 (M+1, 100%). Yield=3%.

Example 17

Synthesis of 5-(4-Aminophenyl)-4-benzothiazol-2-yl-2H-pyrazol-3-ylamine (549-82)

An aqueous solution of Raney Ni (1 mL) was added to a suspension of 4-benzothiazol-2-yl-5-(4-nitrophenyl)-2H-pyrazol-3-ylamine (115 mg, 0.34 mmol) in ethanol (20 mL). To the vigorously stirring solution was added hydrazine hydrate dropwise in 3 portions (3×50 mg, 3 mmol in total), and the resulting mixture was then stirred for 2 hrs. The solids were removed by filtration and the mother liquor was evaporated to afford the crude material. The residue was purified by flash column chromatography eluting with $CH_2Cl_2$:MeOH=9:1 to yield 26 mg (25%) of the title compound as a cream coloured solid. MS (m/z, ES+): 308.1 (M+1, 100%).

Example 18

Synthesis of N-[4-(5-Amino-4-benzothiazol-2-yl-1H-pyrazol-3-yl)-phenyl]-hydroxylamine (590-6)

To a solution of 4-benzothiazol-2-yl-5-(4-nitrophenyl)-2H-pyrazol-3-ylamine (218 mg, 0.65 mmol) in DMF (4 mL) and 95% ethanol (4 mL) at room temperature was added under rapid stirring a suspension of zinc powder (200 mg) in aqueous ammonium chloride (0.15 g in 2 mL of water). The resulting mixture was then stirred for 2 hrs. The residual zinc was removed by filtration and the mother liquor was poured into water (100 mL). A yellow solid was removed by filtration. The aqueous phase was extract with ethyl acetate (2×75 mL). The combined extracts were washed with water, brine, dried over anhydrous sodium sulfate, filtered and evaporated. The resulting crude material was purified by preparative TLC eluting with 10:1 $CH_2Cl_2$:MeOH=10:1 to yield 7 mg (4%) of the title compound as cream coloured solid. MS (m/z, ES+): 324.1 (M+1, 100%).

Example 19

Synthesis of 4-Benzothiazol-2-yl-5-furan-2-yl-2H-pyrazol-3-ylamine (549-92)

1. To a solution of benzothazole-2-acetonitrile (700 mg, 4 mmol) in anhydrous dichloromethane (25 mL) was added triethylamine (1.2 g, 11.9 mmol) and 2-furoyl chloride (522 mg, 4 mmol) dropwise at room temperature. The resulting mixture was stirred at room temperature for 5 hrs. Dichloromethane (100 mL) was then added. The organic phase was washed with 1% HCl aqueous solution, water, brine, and dried over anhydrous magnesium sulfate, filtered and evaporated. The resulting crude material was washed with methanol and dried to afford 590 mg (55%) of furan-2-carboxylic acid 2-benzothiazol-2-yl-2-cyano-1-furan-2-yl-vinyl ester as a yellow solid. MS (m/z, ES+): 363.01 (M+1, 100%).

2. A mixture of furan-2-carboxylic acid 2-benzothiazol-2-yl-2-cyano-1-furan-2-yl-vinyl ester (660 mg, 1.82 mmol) and KOH (108 mg, 1.93 mmol) in ethanol (20 mL) was stirred first at room temperature overnight and then at 50° C. for 2 hours. The resulting suspension was poured into water (200 mL), and the solution was adjusted to pH 7 using 5% HCl solution. The solids were isolated by filtration, washed with water, and air-dried to yield 474 mg (97%) of crude 2-benzothiazol-2-yl-3-furan-2-yl-3-hydroxy acrylonitrile which was used in the next step without further purification. MS (m/z, ES+): 268.98 (M+1, 100%).

3. 2-Benzothiazol-2-yl-3-furan-2-yl-3-hydroxyacrylonitrile (474 mg, 1.77 mmol) was suspended in $POCl_3$ (5 mL). The suspension was first stirred at 50° C. for 1 hr then refluxed for 30 min until the solid dissolved completely. The resulting brown solution was poured over crushed ice (200 mL). The resulting solids were isolated by filtration, washed with water until the pH of the wash water became neutral, and air-dried to yield 477 mg (94%) of 2-benzothiazol-2-yl-3-chloro-3-furan-2-ylacrylonitrile. MS (m/z, ES+): 287.0 ($Cl^{35}$M+1, 100%), 289.0 ($Cl^{37}$M+1, 45%).

4. The 2-benzothiazol-2-yl-3-chloro-3-furan-2-ylacrylonitrile (480 mg, 1.7 mmol) prepared above and hydrazine hydrate (100 mg, 2 mmol) were refluxed in methanol (15 mL) for 3 hrs. The solvent was then evaporated and the residue was purified by flash column chromatography eluting with $CH_2Cl_2$:MeOH=9:1 to afford 130 mg of material. This was further purified by preparative TLC eluting with $CH_2Cl_2$:MeOH=9:1 to yield 23 mg (5%) of the title compound. MS (m/z, ES+): 283.0 (M+1, 100%).

The following compounds were prepared in a manner analogous to the procedure described in Example 19.

4-Benzothiazol-2-yl-5-thiophen-2-yl-2H-pyrazol-3-ylamine (590-42): The title compound (30 mg) was prepared in four steps starting from 870 mg (5 mmol) of benzothazole-2-acetonitrile and 1.6 g (11 mmol) of 2-thiophenecarbonyl chloride. MS (m/z, ES+): 299.0 (M+1, 100%). Yield=19%.

Example 20

Synthesis of 4-(5-Fluoro-6-methoxybenzothiazol-2-yl)-5-furan-2-yl-2H-pyrazol-3-ylamine (549-60)

1. A solution of (5-fluoro-6-methoxybenzothiazol-2-yl)-acetonitrile (150 mg, 0.675 mmol), 2-furoyl chloride (135 μL, 1.37 mmol) and triethylamine (235 μL, 1.69 mmol) in anhydrous dichloromethane was stirred at room temperature for approximately three hours forming a dark brown solution. The crude product, furan-2-carboxylic acid 2-cyano-2-(5-fluoro-6-methoxybenzothiazol-2-yl)-1-furan-2-yl-vinyl ester, was identified by mass spectrometry. MS (m/z, ES+): 410.97 (M+1, 80%), 520.98 (100%).

2. To the above reaction mixture was added a catalytic amount of DMAP (~10 mg). The mixture was stirred for 2 hrs at room temperature. After the reaction was complete, as indicated by TLC analysis, a small amount of concentrated HCl (~1 mL) was added to precipitate the enol. The product was then isolated by filtration and washed with 10% methanol in dichloromethane to yield 175 mg (73%) of 2-(5-fluoro-6-methoxybenzothiazol-2-yl)-3-furan-2-yl-3-hydroxyacrylonitrile as an off white solid. MS (m/z, ES+): 317 (M+1, 100%).

3. To a suspension of 2-(5-fluoro-6-methoxybenzothiazol-2-yl)-3-furan-2-yl-3-hydroxyacrylonitrile (70 mg, 0.199 mmol) in anhydrous dichloromethane (3 mL) and carbon tetrachloride (2 mL) was added triphenylphosphine (175 mg, 0.667 mmol). The reaction mixture was stirred at reflux for three hours then at room temperature overnight to give a dark brown solution containing 3-chloro-2-(5-fluoro-6-methoxybenzothiazol-2-yl)-3-furan-2-ylacrylonitrile. Hydrazine monohydrate (30 μL, 0.62 mmol) and methanol (1 mL) were then added and the solution was refluxed for 2 hrs. At this point, conc. HCl (0.7 mL) was added and the solution was refluxed for an additional hour. The mixture was then cooled to room temperature and neutralized with ammonium hydroxide. The solvent was evaporated and the crude product was purified by flash column chromatography eluting with $CH_2Cl_2$:MeOH=9:1 to yield 15 mg (21%) of the title compound as a brown solid. MS (m/z, ES+): 331.1 (M+1, 100%).

Example 21

Synthesis of 5-Cyclopropyl-4-(5-Fluoro-6-methoxybenzothiazol-2-yl)-2H-pyrazol-3-ylamine (597-65)

To a 10 mL reaction vessel containing (5-fluoro-6-methoxybenzothiazol-2-yl)acetonitrile (100 mg, 0.45 mmol) in 4 mL of anhydrous dichloromethane were added cyclopropane carbonyl chloride (21 μL, 0.231 mmol), 1.35 equivalents of triethylamine (85 μL) and a catalytic amount of DMAP (10 mg). The reaction was agitated at room temperature for approximately 3 hrs. At this point the solvent was evaporated and $CCl_4$ (4 mL), 2.5 equivalents of polystyrene resin bound triphenylphosphine (725 mg, 1.55 mmol/g), and triethylamine (85 μL) were added. After agitation at 65° C. for a minimum of 3 hrs, the reaction mixture was concentrated. Ethanol (4 mL) and hydrazine monohydrate (40 μL, 1.8 equivalents) were then added and the mixture was refluxed for approximately 6 hrs. Several drops of concentrated HCl were then added to ensure complete cyclization of the pyrazole ring. After completion of the reaction, the solids were removed by filtration and the resin was washed three times with 10% methanol in dichloromethane. The filtrate was then concentrated and purified by flash column chromatography eluting with $CH_2Cl_2$:MeOH=50:1 to yield 40 mg (29%) of the title compound as a cream coloured solid. MS (m/z, ES+): 305.1 (M+1, 100%)

The following compounds were prepared in a manner analogous to the procedure described in Example 21.

4-(5-Fluoro-6-methoxybenzothiazol-2-yl)-5-phenyl-2H-pyrazol-3-ylamine (597-67A): The title compound (48 mg) was prepared starting from 100 mg (0.45 mmol) of (5-fluoro-6-methoxybenzothiazol-2-yl)-acetonitrile and 58 μL (0.50 mmol) of benzoyl chloride. MS (m/z, ES+): 341.1 (M+1, 100%). Yield=31%.

5-(2-Chloropyridin-3-yl)-4-(5-fluoro-6-methoxybenzothiazol-2-yl)-2H-pyrazol-3-ylamine (597-67C): The title compound (26 mg) was prepared starting from 100 mg (0.45 mmol) of (5-fluoro-6-methoxybenzothiazol-2-yl)-acetonitrile and 87 mg (0.50 mmol) of 2-chloronicotinoyl chloride. MS (m/z, ES+): 376.1 (Cl$^{35}$M+1, 100%), 378.1 (Cl$^{37}$M+1, 40%). Yield=15%.

4-(5-Fluoro-6-methoxybenzothiazol-2-yl)-5-(4-fluorophenyl)-2H-pyrazol-3-ylamine (597-67D): The title compound (26 mg) was prepared starting from 100 mg (0.45 mmol) of (5-fluoro-6-methoxybenzothiazol-2-yl)-acetonitrile and 59 μL (0.50 mmol) of 4-fluorobenzoyl chloride. MS (m/z, ES+): 359.1 (M+1, 100%). Yield=28%.

4-(5-Fluoro-6-methoxybenzothiazol-2-yl)-5-(3-fluorophenyl)-2H-pyrazol-3-ylamine (597-67E): The title compound (37 mg) was prepared starting from 100 mg (0.45 mmol) of (5-fluoro-6-methoxybenzothiazol-2-yl)-acetonitrile and 59 μL (0.50 mmol) of 3-fluorobenzoyl chloride. MS (m/z, ES+): 359.1 (M+1, 100%). Yield=22%.

4-(5-Fluoro-6-methoxybenzothiazol-2-yl)-5-(4-methoxyphenyl)-2H-pyrazol-3-ylamine (597-69A): The title compound (32 mg) was prepared starting from 80 mg (0.36 mmol) of (5-fluoro-6-methoxybenzothiazol-2-yl)-acetonitrile and 68 mg (0.4 mmol) of 4-methoxybenzoyl chloride. MS (m/z, ES+): 371.1 (M+1, 100%). Yield=24%.

4-(5-Fluoro-6-methoxybenzothiazol-2-yl)-5-isoxazol-5-yl-2H-pyrazol-3-ylamine (597-69F): The title compound (5 mg) was prepared starting from 80 mg (0.36 mmol) of (5-fluoro-6-methoxybenzothiazol-2-yl)-acetonitrile and 38 μL (0.4 mmol) of 5-isoxazolecarbonyl chloride. MS (m/z, ES+): 332.0 (M+1, 100%), 318.0 (enol, 30%). Yield=11%.

4-(5-Fluoro-6-methoxybenzothiazol-2-yl)-5-(3-nitrophenyl)-2H-pyrazol-3-ylamine (597-69B): The title compound (24 mg) was prepared starting from 80 mg (0.36 mmol) of (5-fluoro-6-methoxybenzothiazol-2-yl)-acetonitrile and 74 mg (0.4 mmol) of 3-nitrobenzoyl chloride. MS (m/z, ES+): 386.1 (M+1, 100%). Yield=17%.

4-(5-Fluoro-6-methoxybenzothiazol-2-yl)-5-(4-fluorophenyl)-2H-pyrazol-3-ylamine (597-69D): The title compound (26 mg) was prepared starting from 80 mg (0.36 mmol) of (5-fluoro-6-methoxybenzothiazol-2-yl)-acetonitrile and 47 μL (0.4 mmol) of 4-fluorobenzoyl chloride. MS (m/z, ES+): 359.0 (M+1, 100%). Yield=20%.

4-(5-Fluoro-6-methoxybenzothiazol-2-yl)-5-thiophen-2-yl-2H-pyrazol-3-ylamine (597-69E): The title compound (32 mg) was prepared starting from 80 mg (0.36 mmol) of (5-fluoro-6-methoxybenzothiazol-2-yl)-acetonitrile and 42 μL (0.4 mmol) of 2-thiophenecarbonyl chloride. MS (m/z, ES+): 347.0 (M+1, 100%). Yield=25%.

4-(5-Fluoro-6-methoxybenzothiazol-2-yl)-5-(5-mitrofuran-2-yl)-2H-pyrazol-3-ylamine (597-69G): The title compound (12 mg) was prepared starting from 80 mg (0.36 mmol) of (5-fluoro-6-methoxybenzothiazol-2-yl)-acetonitrile and 70 mg (0.4 mmol) of 5-nitro-2-furoyl chloride. MS (m/z, ES+): 376.0 (M+1, 100%). Yield=9%.

4-(5-Fluoro-6-methoxybenzothiazol-2-yl)-5-(2-phenylcyclopropyl)-2H-pyrazol-3-ylamine (597-71B): The title compound (5 mg) was prepared starting from 100 mg (0.45 mmol) of (5-fluoro-6-methoxybenzothiazol-2-yl)-acetonitrile and 75 μL (0.48 mmol) of trans-2-phenylcyclopropylcarbonyl chloride. MS (m/z, ES+): 381.1 (M+1, 100%). Yield=4%.

Example 22

Synthesis of 3-(5-Amino-4-benzothiazol-2-yl-2H-pyrazol-3-yl)-propan-1-ol

1. To a solution of benzothazole-2-acetonitrile (870 mg, 5 mmol) in anhydrous dichloromethane (50 mL) were first added triethylamine (1.11 g, 11 mmol), and then 4-bromobutyryl chloride (1.85 g, 10 mmol) dropwise at room temperature. The resulting mixture was stirred at room temperature for 4 hrs. Additional triethylamine (0.22 g) and 4-bromobutyryl chloride (0.48 g) were added and stirring was continued for an additional 2 hrs. The reaction solution was diluted with dichloromethane (100 mL). The organic phase was washed with 0.1% NaOH, water, brine, dried over anhydrous sodium sulfate, filtered and evaporated. The resulting crude material was washed with methanol and dried to afford 97 mg (6%) of benzothiazol-2-yl-(dihydrofuran-2-ylidene)-acetonitrile. MS (m/z, ES+): 343 (M+1, 100%).

2. The benzothiazol-2-yl-(dihydrofuran-2-ylidene)-acetonitrile (90 mg, 0.37 mmol) prepared above and hydrazine hydrate (25 mg, 0.5 mmol) were refluxed in ethanol (15 mL) for 10 hours. The solvent was evaporated and the resulting residue was triturated with dichloromethane. The solid was isolated by filtration and was then washed with dichloromethane and methanol to yield 60 mg (67%) of the title compound as a cream coloured solid. MS (m/z, ES+): 275.1 (M+1, 100). $^1$H NMR (300 MHz, ppm, DMSO-d$_6$): δ (ppm), 11.5-12.2 (br s, 1H), 8.00 (d, 1H), 7.86 (d, 1H), 7.77 (t, 2H), 7.29 (t, 1H), 7.00-5.20 (br m, 2H), 4.55 (s, 1H), 3.52 (q, 2H), 2.83 (br s, 2H), 1.84 (q, 2H).

The following compounds were prepared in a manner analogous to the procedure described in Example 22.

4-(5-Amino-4-benzothiazol-2-yl-1H-pyrazol-3-yl)-butan-1-ol: The title compound (47 mg) was prepared starting from 522 mg (3 mmol) of benzothazole-2-acetonitrile and 538 mg (3.6 mmol) of 5-bromopentanoyl chloride. MS (m/z, ES+): 289.1 (M+1, 100%). Yield=48%.

Example 23

Synthesis of 4-Benzothiazol-2-yl-5-(3-methylaminopropyl)-2H-pyrazol-3-ylamine

1. To a solution of concentrated H$_2$SO$_4$ (3 mL) and hydrobromic acid (6 mL of 48%) was added 3-(5-amino-4-benzothiazol-2-yl-2H-pyrazol-3-yl)-propan-1-ol (810 mg, 3.0 mmol). The resulting mixture was refluxed for 2 hrs. The mixture was cooled to room temperature, poured into ice water, and adjusted to pH 3-4 using 5% NaOH solution. The resulting sticky solid was isolated by filtration, washed with water and air-dried to yield 815 mg (80%) of 4-benzothiazol-2-yl-5-(3-bromopropyl)-2H-pyrazol-3-ylamine as a cream coloured solid. The crude material was used in the subsequent step without further purification. MS (m/z, ES+): 337.1 (Br$^{79}$M+1, 61%), 339.1 (Br$^{81}$M+1, 59%), 257.2 (M-HBr, 100%).

2. A mixture of 4-benzothiazol-2-yl-5-(3-bromopropyl)-2H-pyrazol-3-ylamine (130 mg, 0.39 mmol) and methylamine (5 mL of a 2 M solution in THF, 10 mmol) was stirred at room temperature for 60 hrs. The resulting solid was isolated by filtration, washed with THF, and then with water. The product was air dried to yield 38 mg (32%) of the title compound as an off white solid. MS (m/z, ES+): 288.2 (M+1, 100%).

The following compounds were prepared in a manner analogous to the procedure described in Example 23.

5-(3-Aminopropyl)-4-benzothiazol-2-yl-2H-pyrazol-3-ylamine (590-86A): The title compound (12 mg) was prepared using 130 mg (0.39 mmol) of 4-benzothiazol-2-yl-5-(3-bromopropyl)-2H-pyrazol-3-ylamine, which was derived from 3-(5-amino-4-benzothiazol-2-yl-1H-pyrazol-3-yl)-propan-1-ol, and a saturated solution of ammonia gas in ethanol. MS (m/z, ES+): 274.2 (M+1, 100%), 257.2 (M-NH2, 70%).

4-Benzothiazol-2-yl-5-(3-dimethylaminopropyl)-2H-pyrazol-3-ylamine (590-87A): The title compound (100 mg) was prepared using 200 mg (0.59 mmol) of 4-benzothiazol-2-yl-5-(3-bromopropyl)-2H-pyrazol-3-ylamine, which was derived from 3-(5-amino-4-benzothiazol-2-yl-1H-pyrazol-3-yl)-propan-1-ol, and 5 mL of a 2 M solution of dimethylamine in THF (10 mmol). MS (m/z, ES+): 302.1 (M+1, 100%).

4-Benzothiazol-2-yl-5-(4-methylaminobutyl)-2H-pyrazol-3-ylamine (590-94): The title compound (30 mg) was prepared using 185 mg (0.39 mmol) of 4-benzothiazol-2-yl-5-(4-bromobutyl)-2H-pyrazol-3-ylamine, which was derived from 4-(5-amino-4-benzothiazol-2-yl-1H-pyrazol-3-yl)-butan-1-ol, and 5 mL of a 2 M solution of methylamine in THF (10 mmol). MS (m/z, ES+): 302.4 (M+1, 100%).

4-Benzothiazol-2-yl-5-(4-dimethylaminobutyl)-2H-pyrazol-3-ylamine (590-95): The title compound (41 mg) was prepared using 185 mg (0.39 mmol) of 4-benzothiazol-2-yl-5-(4-bromobutyl)-2H-pyrazol-3-ylamine, which was derived from 4-(5-amino-4-benzothiazol-2-yl-1H-pyrazol-3-yl)-butan-1-ol, and 5 mL of a 2 M solution of dimethylamine in THF (10 mmol). MS (m/z, ES+): 316.4 (M+1, 100%).

Example 24

Synthesis of 4-Benzothiazol-2-yl-5-piperidin-4-yl-2H-pyrazol-3-ylamine (610-48)

1. To a solution of benzothazole-2-acetonitrile (700 mg, 4 mmol), triethylamine (1.1 g, 10.9 mmol), and a catalytic amount of DMAP, in 60 mL of anhydrous dichloromethane at room temperature under argon, was added 1-acetylpiperidine-4-carbonylchloride hydrochloride (1.1 g, 4.46 mmol) in small portions over 2 hrs. The resulting mixture was stirred at room temperature overnight. The reaction mixture was diluted with dichloromethane. The organic phase was washed with water, brine, dried over anhydrous sodium sulfate, filtered, and evaporated. The resulting crude product was purified by flash column chromatography eluting with $CH_2Cl_2$:MeOH=20:1 to yield 880 mg (67%) of 3-(1-acetylpiperidin-4-yl)-2-benzothiazol-2-yl-3-hydroxyacrylonitrile as a light brown solid. MS (ES+): 328.1 (M+1, 100%).

2. To a solution of the above prepared 3-(1-acetylpiperidin-4-yl)-2-benzothiazol-2-yl-3-hydroxyacrylonitrile (415 mg, 1.27 mmol) in anhydrous dichloromethane (20 mL) at room temperature under argon were added triethylamine (193 mg, 1.9 mmol) and tosyl chloride (303 mg, 1.59 mmol) in small portions. The resulting mixture was stirred at room temperature for 6 hrs. The reaction mixture was diluted with dichloromethane. The organic phase was washed with 1% HCl, 0.5% NaOH, water, brine, and dried over anhydrous sodium sulfate, filtered, and evaporated. The resulting crude product was purified by flash column chromatography eluting with $CH_2Cl_2$:MeOH=20:1 to yield 140 mg (23%) of toluene-4-sulfonic acid 1-(1-acetylpiperidin-4-yl)-2-benzothiazol-2-yl-2-cyanovinyl ester. MS (m/z, ES+): 482.1 (M+1, 100%).

3. A mixture of the above prepared toluene-4-sulfonic acid 1-(1-acetylpiperidin-4-yl)-2-benzothiazol-2-yl-2-cyanovinyl ester (140 mg, 0.29 mmol) and hydrazine hydrate (25 mg, 0.5 mmol) in methanol was refluxed overnight. The solvent was evaporated and the residue was purified by flash column chromatography eluting with $CH_2Cl_2$:MeOH=20:1 to yield 54 mg (55%) of 1-[4-(5-amino-4-benzothiazol-2-yl-1H-pyrazol-3-yl)-piperidin-1-yl]-ethanone. MS (ES+): 342.1 (M+1, 100%).

4. A solution of the above prepared 1-[4-(5-amino-4-benzothiazol-2-yl-1H-pyrazol-3-yl)-piperidin-1-yl]-ethanone (54 mg, 0.158 mmol) in 6N HCl (10 mL) was refluxed for 6 hrs and was allowed to cool to room temperature overnight. The resulting mixture was poured over crushed ice (20 mL) and the solution was adjusted to neutral pH using a 10% NaOH solution. The resulting solution was saturated with NaCl and was extracted with ethyl acetate (10×50 mL). The combined extracts were washed once with brine, dried over anhydrous sodium sulfate, filtered and evaporated. The resulting crude product was purified by flash column chromatography eluting with $CH_2Cl_2$:MeOH=20:1 with 1% ammonia to yield 15 mg (32%) of the title compound. MS (m/z, ES+): 300.14 (M+1, 100%).

Example 25

2-(3-Phenyl-1H-pyrazol-4-yl)benzothiazole

To a solution of 2-methylbenzothiazole (149 mg, 1 mmol) in THF was added n-BuLi (0.5 mL of a 2M solution in cyclohexane, 1 mmol) at −70° C. The mixture was stirred at this temperature for 1.5 hours and then ethyl benzoate (150 mg, 1 mmol) was added dropwise. After stirring for another 1.5 hours, a saturated solution of $NH_4Cl$ was added dropwise. The reaction was then allowed to warm to 5° C. and a precipitate obtained was isolated by filtration and washed with water. The resulting crude material was recrystallized from methanol to yield the desired intermediate.

A solution of the above prepared intermediate (147 mg, 0.58 mmol) and DMF dimethyl acetal (76 mg, 0.64 mmol) in 5 mL of toluene was stirred overnight at room temperature and was then heated to reflux for 2 hours. The mixture was concentrated in vacuo and the residue was purified by recrystallization to afford the desired product.

The above-prepared intermediate (86 mg, 0.28 mmol) was dissolved in methanol (10 mL) and then treated with hydrazine hydrate (30 mg, 0.6 mmol). The mixture was stirred at room temperature for 16 hours. At this point, the solvent was removed in vacuo and the residue was purified by recrystallization to afford 71 mg of the title compound. MS (m/z, ES+): 278 (M+1, 100%); $^1$H NMR (400 MHz, ppm, $CDCl_3$): δ 13.57 (br s, 1H), 8.6 and 8.1 (br, 1H), 7.99 (d, 1H), 7.91 (d, 1H), 7.72-7.66 (m, 2H), 7.55-7.40 (m, 4H), 7.35 (dd, 1H). Yield=27%.

The following compounds were prepared in a manner analogous to the procedure described in Example 25.

2-[3-(4-Methoxyphenyl)-1H-pyrazol-4-yl]benzothiazole: The title compound (457 mg) was prepared in three steps starting from 1.49 g (10 mmol) of 2-methylbenzothiazole and 1.66 g (10 mmol) of methyl 4-methoxybenzoate. MS (m/z, ES+): 308 (M+1, 100%). $^1$H NMR (400 MHz, ppm, $CDCl_3$): δ 8.28 (s, 1H), 8.00 (d, $^3J$=8.1 Hz, 1H), 7.75 (d, $^3J$=8.0 Hz, 1H), 7.57 (d, $^3J$=8.6 Hz, 2H), 7.44 (dd, $^3J$=7.4 Hz, $^3J$=8.1 Hz, 1H), 7.33 (dd, $^3J$=7.4 Hz, $^3J$=8.0 Hz, 1H), 7.00 (d, $^3J$=8.6 Hz, 2H), 3.87 (s, 3H). Yield=18%.

2-[3-(2-Methoxyphenyl)-1H-pyrazol-4-yl]benzothiazole: The title compound (430 mg) was prepared in four steps starting from 1.49 g (10 mmol) of 2-methylbenzothiazole and 1.66 g (10 mmol) of methyl 2-methoxybenzoate. After the reaction with hydrazine, the addition product was dissolved in methanol and heated to reflux with a catalytic amount of p-TSA (15 mg) for 2 hours to yield the title compound. MS (m/z, ES+): 308 (M+1, 100%). Yield=14%.

2-(3-Methyl-1H-pyrazol-4-yl)-benzothiazole (515-84): The title compound (970 mg) was prepared in three steps starting from 2-methylbenzothiazole and ethyl acetate. MS (m/z, ES+): 216.04 (M+1, 100%).

Example 26

Synthesis of 4-(4-Benzothiazol-2-yl-1H-pyrazol-3-yl)phenol

To a suspension of 2-[3-(4-methoxyphenyl)-1H-pyrazol-4-yl]benzothiazole (100 mg, 0.33 mmol) was slowly added tribromoborane (3.3 mL of a 1 M solution in $CH_2Cl_2$, 3.3 mmol). The mixture was stirred overnight. The reaction was then quenched by the addition of methanol. The mixture was neutralized with sodium carbonate solution and extracted three times with ethyl acetate. The organic extracts were combined, washed with brine, dried over $Na_2SO_4$, filtered, and evaporated. The crude material was recrystallized from ethyl acetate to yield 64 mg (66%) of the title compound as a yellow solid. MS (m/z, ES+): 294 (M+1, 100%). $^1$H NMR (400 MHz, ppm, DMSO-$d_6$): δ 13.5 (br s, 1H), 9.80 (br s, 1H), 8.22 (br s, 1H), 7.98 (d, $^3J$=8.1 Hz, 1H), 7.91 (d, $^3J$=8.0 Hz, 1H), 7.47 (d, $^3J$=8.0 Hz, 2H), 7.45 (dd, $^3J$=7.4 Hz, $^3J$=8.1 Hz, 1H), 7.34 (dd, $^3J$=7.4 Hz, $^3J$=8.0 Hz, 1H), 6.89 (d, $^3J$=8.0 Hz, 2H).

Example 27

Synthesis of 2-(4-Benzothiazol-2-yl-1H-pyrazol-3-yl)phenol 2-(4-Benzothiazol-2-yl-1H-pyrazol-3-yl)phenol (82 mg) was prepared in analogy to the procedure as described in Example 26 starting from 100 mg (0.33 mmol) of 2-[3-(2-methoxy-phenyl)-1H-pyrazol-4-yl]benzothiazole. MS (m/z, ES+): 294 (M+1, 100%). Yield=85%.

Example 28

Synthesis of 4-Benzothiazol-2-yl-2-methyl-2H-pyrazol-3-ylamine

A solution of benzothiazol-2-ylacetonitrile (522 mg, 3 mmol) and DMF dimethyl acetal (394 mg, 3.3 mmol) in toluene (6 mL) was heated to reflux for 3 hours and then stirred overnight at room temperature. The mixture was concentrated and the residue was purified by recrystallization from 2-propanol to yield 350 mg (51%) of the product as a pale yellow solid.

A mixture of the 2-benzothiazol-2-yl-3-dimethylaminoacrylonitrile prepared above (96 mg, 0.42 mmol) and triethylamine (0.3 mL) in EtOH (10 mL) was treated with methylhydrazine sulfate (180 mg, 1.25 mmol) and the mixture was heated to reflux for 2 days. The solution was concentrated in vacuo and the residue was purified by flash chromatography (hexanes:EtOAc=1:1) to yield 47 mg (49%) of the title compound as a yellow powder. MS (m/z, ES+): 231 (M+1, 100%).

Example 29

Synthesis of 2-(3-amino-5-methyl-1H-pyrazol-4-yl)-benzothiazole-6-carboxylic acid methyl ester (574-26E2)

A solution of 2-(3-amino-5-methyl-1H-pyrazol-4-yl)-benzothiazole-6-carboxylic acid (1.52 g, 5.5 mmol) in 500 mL of anhydrous methanol containing HCl gas was heated to reflux for 5 hrs. The excess methanol was removed by distillation and the solution was neutralized by the addition of a solution of saturated sodium carbonate. The resulting solids were isolated by filtration to yield 500 mg of the title compound as a yellow solid. MS (m/z, ES+): 289.1 (M+1, 100%).

Example 30

Synthesis of 2-(3-Amino-5-methyl-1H-pyrazol-4-yl)-4,5,6-trifluorobenzothiazole-7-sulfonic acid amide (598-79)

5-Methyl-4-(4,5,6-trifluorobenzothiazol-2-yl)-2H-pyrazol-3-ylamine (474 mg; 1.67 mmol) was heated at 140-150° C. in chlorosulfonic acid (4 ml) for 72 h. After cooling to room temperature, the mixture was poured over ice, and the product was extracted into ethyl acetate. The combined extracts were washed with water, dried over sodium sulfate, filtered and evaporated. The residue was dissolved in ethanol and a solution of ammonia in ethanol (15 ml) was added. The reaction mixture was stirred at room temperature for 1 hr, while ammonia gas was bubbled through the mixture. The volume of solvent was then reduced evaporated and water was added. The resulting beige precipitate was filtered off and dried in vacuum to yield 490 mg (81%) of the title compound. MS (m/z, ES+): 313.0 ($Cl^{35}$M+1, 100%), 315.0 ($Cl^{37}$M+1, 50%); $^1$H NMR (300 MHz, ppm, DMSO-$d_6$): δ 11.75 (br s, 1H), 7.80 (d, 1H, $J_{HF}$=11.4 Hz), 6.25 (s, 2H), 3.95 (s, 3H), 2.39 (s, 3H).

Example 31

Synthesis of 4-(7-Chloro-5-fluoro-6-methoxybenzothiazol-2-yl)-5-methyl-1H-pyrazol-3-ylamine (598-80)

4-(5-Fluoro-6-methoxybenzothiazol-2-yl)-5-methyl-2H-pyrazol-3-ylamine (596 mg; 2.14 mmol) was mixed with 4 mL of sulfuryl chloride. The reaction was stirred at room temperature for several hours and then the reaction was quenched by the addition of water. The resulting precipitate was isolated by filtration to yield 417 mg (62%) of the title compound. MS (m/z, ES+): 364.2 (M+1, 100%).

Example 32

Synthesis of 2-(5-Amino-3-methyl-1H-pyrazol-4-yl)-benzothiazol-5-ol (574-13)

To a suspension of 4-(5-methoxy-benzothiazol-2-yl)-5-methyl-2H-pyrazol-3-ylamine (60 mg, 0.23 mmol) in $CH_2Cl_2$ (5 mL) at 4° C. was slowly added tribromoborane (2.3 mL of a 1M solution in dichloromethane, 2.3 mmol). The reaction temperature was maintained at 4° C. and the solution was stirred overnight. The mixture was then neutralized with sodium carbonate solution. The resulting solids were isolated by filtration and were purified by flash chromatography eluting with $CHCl_3$:MeOH=9:1 to yield 10 mg (19%) of the title compound as a cream coloured solid. MS (m/z, ES+): 247.1 (M+1, 100%).

Example 33

Synthesis of [2-(5-Amino-3-methyl-1H-pyrazol-4-yl)-benzothiazol-5-yl]-methanol (574-21)

To a solution of 2-(5-amino-3-methyl-1H-pyrazol-4-yl)-benzothiazole-5-carboxylic acid ethyl ester (30 mg) in THF (1 mL) was added lithium aluminum hydride (4 mg). The reaction mixture was stirred at room temperature for 5 hrs at which point sodium sulfate nonahydrate was added. The resulting mixture was stirred for an additional 30 min. The solids were removed by filtration. The solvent was then evaporated and the residue was purified by flash column chromatography eluting with $CHCl_3$:MeOH=9:1 to yield 21 mg (81%) of the title compound as a cream coloured solid. MS (m/z, ES+): 261.1 (M+1, 100%).

The following compounds were prepared in a manner analogous to the procedure described in Example 33.

[2-(5-Amino-3-methyl-1H-pyrazol-4-yl)-benzothiazol-6-yl]-methanol (574-36A): The title compound (340 mg) was prepared starting from 470 mg (1.63 mmol) of 2-(3-amino-5-methyl-1H-pyrazol-4-yl)-benzothiazole-6-carboxylic acid methyl ester. The final product was purified by recrystallization from an ethanol/water mixture. MS (m/z, ES+): 261.0 (M+1, 100%). Yield=80%.

[2-(3-Amino-5-methyl-1H-pyrazol-4-yl)-5-fluorobenzothiazol-6-yl]-methanol (574-50A): The title compound (30 mg) was prepared starting from 54 mg (0.18 mmol) of 2-(3-amino-5-methyl-1H-pyrazol-4-yl)-5-fluorobenzothiazole-6-carboxylic acid methyl ester. The final product was purified by recrystallization from an ethanol/water mixture. MS (m/z, ES+): 279.1 (M+1, 100%). Yield=61%.

Example 34

Synthesis of 5-Methyl-4-(6-pyrrolidin-1-ylmethyl-benzothiazol-2-yl)-2H-pyrazol-3-ylamine (574-36C)

1. To a solution of concentrated $H_2SO_4$ (0.3 mL) and hydrobromic acid (0.6 mL, 48%) was added [2-(5-amino-3-methyl-1H-pyrazol-4-yl)-benzothiazol-6-yl]-methanol (52 mg, 0.2 mmol). The resulting mixture was refluxed for 2 hrs. Upon cooling to room temperature, the mixture was poured into ice water resulting a milky solution. The suspension was neutralized to pH 3-4 with 5% NaOH solution. The resulting cream coloured solid was isolated by filtration, washed with water and air-dried to yield 58 mg of 4-(6-bromomethylbenzothiazol-2-yl)-5-methyl-2H-pyrazol-3-ylamine. The crude material was used in the subsequent step without further purification.

2. To a suspension of 4-(6-bromomethylbenzothiazol-2-yl)-5-methyl-2H-pyrazol-3-ylamine (20 mg) in ethanol (1 mL) was added excess pyrrolidine. The reaction mixture was stirred at room temperature overnight. The solvent was then removed by evaporation and the residue was purified by flash column chromatography eluting with $CHCl_3$:MeOH=9:1 to yield 2.7 mg of the title compound as a cream coloured solid. MS (m/z, ES+): 314.1 (M+1, 45%), 243.0 (M-$C_4H_8N$, 100%).

The following compounds were prepared in a manner analogous to the procedure described in Example 34.

5-Methyl-4-(6-methylaminomethylbenzothiazol-2-yl)-2H-pyrazol-3-ylamine (574-36E): The title compound (1.6 mg) was prepared starting from 18 mg of 4-(6-bromomethylbenzothiazol-2-yl)-5-methyl-2H-pyrazol-3-ylamine and excess methylamine. MS (m/z, ES+): 274.1 (M+1, 100%), 243.1 (M-$CH_3NH$, 60%).

5-Methyl-4-[6-(4-methylpiperazin-1-ylmethyl)-benzothiazol-2-yl]-2H-pyrazol-3-ylamine (574-36D): The title compound (9 mg) was prepared starting from 20 mg of 4-(6-bromomethylbenzothiazol-2-yl)-5-methyl-2H-pyrazol-3-ylamine and excess 1-methylpiperazine. MS (m/z, ES+): 343.1 (M+1, 20%), 244.1 (M-$CH_3N(CH_2)_4N$+1, 100%).

5-Methyl-4-(6-morpholin-4-ylmethylbenzothiazol-2-yl)-2H-pyrazol-3-ylamine (574-38B): The title compound (27 mg) was prepared starting from 40 mg of 4-(6-bromometh-ylbenzothiazol-2-yl)-5-methyl-2H-pyrazol-3-ylamine and excess morpholine. MS (m/z, ES+): 330.1 (M+1, 30%), 243 (M-$O(CH_2)_4N$, 100%).

4-(6-Dimethylaminomethylbenzothiazol-2-yl)-5-methyl-2H-pyrazol-3-ylamine (574-38A): The title compound (24 mg) was prepared starting from 40 mg of 4-(6-bromomethylbenzothiazol-2-yl)-5-methyl-2H-pyrazol-3-ylamine and excess dimethylamine. MS (m/z, ES+): 288.1 (M+1, 20%), 243.1 (M-$(CH_3)_2N$, 100%).

2-{[2-(5-Amino-3-methyl-1H-pyrazol-4-yl)-benzothiazol-6-ylmethyl]-amino}-ethanol (574-38C): The title compound (10 mg) was prepared starting from 40 mg of 4-(6-bromomethylbenzothiazol-2-yl)-5-methyl-2H-pyrazol-3-ylamine and excess 2-aminoethanol. MS (m/z, ES+): 304.1 (M+1, 10%), 243.2 (M-$HOCH_2CH_2NH$, 100%).

3-{[2-(5-Amino-1H-pyrazol-4-yl)-benzothiazol-6-ylmethyl]-amino}-N-methylbenzenesulfonamide (574-38F): The title compound (9 mg) was prepared starting from 40 mg of 4-(6-bromomethylbenzothiazol-2-yl)-5-methyl-2H-pyrazol-3-ylamine and excess 3-amino-N-methylbenzenesulfonamide. MS (m/z, ES+): 429.2 (M+1, 100%).

4-(6-Dimethylaminomethyl-5-fluorobenzothiazol-2-yl)-5-methyl-1H-pyrazol-3-ylamine (574-50C): The title compound (28 mg) was prepared in two steps starting from 30 mg (0.1 mmol) of [2-(3-amino-5-methyl-1H-pyrazol-4-yl)-5-fluorobenzothiazol-6-yl]methanol. The reaction of the bromide was carried out with excess dimethylamine. MS (m/z, ES+): 306.1 (M+1, 43%), 261.1 (60%), 153.5 (100%).

Example 35

4-Benzothiazol-2-yl-$N^5$-(1H-imidazol-2-ylmethylene)-1H-pyrazole-3,5-diamine (610-49)

A mixture of 4-benzothiazol-2-yl-1H-pyrazole-3,5-diamine (50 mg, 0.22 mmol) and 2-imidazolecarbonylaldehyde (22 mg, 0.22 mmol) in methanol (10 mL) were refluxed overnight. The solvent was evaporated and the resulting crude material was purified by flash column chromatography eluting with $CH_2Cl_2$:MeOH=20:1 to yield 21 mg (31%) of the title compound. MS (m/z, ES+): 310.1 (M+1, 15%), 232.1 (M-77, 60%), 142.0 (M-167, 68%), 101.1 (100%).

Example 36

4-Benzothiazol-2-yl-$N^5$-(1H-imidazol-2-ylmethyl)-1H-pyrazole-3,5-diamine (610-52)

A mixture of 4-benzothiazol-2-yl-$N^5$-(1H-imidazol-2-ylmethylene)-1H-pyrazole-3,5-diamine (13 mg, 0.042 mmol) and $NaBH_4$ (10 mg) was stirred at room temperature for 3 hrs. The solvent was then evaporated and the residue was purified by flash column chromatography eluting with a gradient of $CH_2Cl_2$ to $CH_2Cl_2$:MeOH=4:1 to yield 12 mg (84%) of the title compound. MS (m/z, ES+): 312.1 (M+1, 80%), 232.1 (100%).

Example 37

Synthesis of 2-(1H-Pyrazol-4-yl)-benzothiazole-6-sulfonic acid amide (523-88-39)

A solution of 2-(1H-pyrazol-4-yl)benzothiazole (600 mg, 0.30 mmol) in neat chlorosulfonic acid was heated to 150° C. for 5 hrs. The reaction mixture was then poured over ice and the resulting precipitate was isolated by filtration to yield a mixture of 2-(1H-pyrazol-4-yl)-benzothiazole-6-sulfonyl chloride and 2-(1H-pyrazol-4-yl)-benzothiazole-4-sulfonyl chloride.

The crude material prepared above was reacted with ammonia hydroxide in ethanol. The solvent was evaporated and the crude material was purified by flash column chromatography to yield 37 mg of the title compound contaminated with approximately 25% of 2-(1H-pyrazol-4-yl)-benzothiazole-4-sulfonic acid amide as determined by $^1$H NMR. MS (m/z, ES+): 281.2 (M+1, 100%); $^1$H NMR (300 MHz, ppm, DMSO-d$_6$): 13.50 (br s, 1H), 8.7 (d, 1H), 8.8 (br s, 2H), 8.08 (d, 1H), 7.9 (dd, 1H), 7.42 (br s, 2H) (major isomer).

Example 38

Synthesis of (4-Benzothiazol-2-yl-2H-pyrazol-3-yl)-methylamine (523-32A)

A solution of 4-benzothiazol-2-yl-1H-pyrazol-3-ylamine (1.1 g, 5.0 mmol) in 20 mL of formic acid was heated to 70° C. overnight. The formic acid was evaporated under reduced pressure and the resulting crude material was recrystallized from ethanol to yield 1.1 g (90%) of N-(4-benzothiazol-2-yl-1H-pyrazol-3-yl)-formamide.

To the above prepared N-(4-benzothiazol-2-yl-1H-pyrazol-3-yl)-formamide (0.50 g, 2.0 mmol) in 50 mL of anhydrous THF at 0° C. was added 0.50 g of lithium aluminum hydride. The reaction was stirred for 1 hr and then was quenched by the addition of saturated ammonium chloride solution. The solids were removed by filtration. The solvent was then evaporated and the crude product was purified by recrystallization from acetone to yield 280 mg (61%) of the title compound. MS (m/z, ES+): 231.1 (M+1, 100%).

For the biological examples below, conditions are room temperature unless otherwise stated.

Example 39

In Vitro Activity Profile for Kinases

Enzyme Preparation and Use

The target ILK is a full-length recombinant protein expressed in Hi5 insect cells by baculovirus infection. Recombinant ILK protein was expressed using cultured insect cells and a baculovirus expression system. Standard techniques for DNA manipulation were used to produce recombinant DNA molecules and baculoviruses (Sambrook. J., Fritsch, E. F. and Maniatis, T. 1989, *Molecular cloning, a laboratory manual*. Second edition. Cold Spring Harbor Laboratory Press. NY; Crossen, R. and Gruenwald, S. 1998. *Baculovirus expression Vector System Manual*. 5$^{th}$ Edition. (Pharmingen, San Diego, Calif.). The ILK open reading frame (Hannigan et al., supra.), excluding the 5' and 3' untranslated regions, was inserted into the baculovirus transfer vector pAcG2T (Pharmingen) to produce a GST fusion protein under the control of the strong AcNPV polyhedrin promoter. This ILK transfer construct was then co-transfected with BaculoGold™ DNA (Pharmingen) into Sf9 insect cells (Invitrogen) and a high titre preparation of GST-ILK recombinant baculovirus was produced by amplification in Sf9 cells. Liter scale expression of GST-ILK recombinant protein was done in 1000 mL spinner flasks (Bellco) by infection of Hi5 insect cells (Invitrogen) grown in Ex-Cell™ 400 serum free media (JRH Biosciences) at a multiplicity of infection of approximately 5. The cells were harvested three days after infection and lysed on ice in ILK Lysis Buffer (ILB; 10 mM imidazole, pH 7.5, 50 mM NaCl, 0.1% NP-40, 0.1% β-mercaptoethanol, 0.5 mM PMSF, 1 mM benzamidine) with dounce tissue grinder (Kontes). The lysate was centrifuged at 10,000 g for 15 minutes at 4° C. and the supernatant was discarded. The pellet was re-suspended in ILB using the homogenizer and centrifuged as above. Then the pellet was washed twice in ILK extraction buffer (IEB, 10 mM imidazole, pH7.5, 400 mM NaCl, 1% NP-40, 0.1% β-mercaptoethanol, 0.5 mM PMSF, 1 mM benzamidine). The pellet was then resuspended in DNAse-ATP buffer Buffer (DAB, 10 mM imidazole, PH7.5, 400 mM NaCl, 5 mM EDTA, 1% NP-40, 0.1% β-mercaptoethanol, 0.5 mM PMSF, 1 mM benzamidine, 10 ug/mL DNAse I, 1 mM ATP, 10 mM MgCl$_2$, 1 mM MnCl$_2$, 5 uM β-methyl aspartic acid, 2 mM NaF) and stirred for 30 minutes at ambient temperature. The mixture was centrifuged at 10,000×g for 20 minutes and the pellet resuspended and washed once in High Salt Buffer (HSB, 10 mM imidazole, PH7.5, 400 mM NaCl, 5 mM EDTA, 0.1% β-mercaptoethanol, 0.5 mM PMSF, 1 mM benzamidine). The suspension was stirred for 30 minutes at ambient temperature, and then centrifuged at 10,000 g for 20 minutes. Finally, the pellet was resuspended in ILK Storage Buffer (ISB, 10 mM imidazole, PH7.5, 0.2 mM EDTA, 0.1% β-mercaptoethanol, 0.5 mM PMSF, 30% glycerol) and stored at −80° C.

Biochemical analysis of the activated enzyme was performed on recombinant human ILK1 protein preparation using the experimental protocol outlined in the section entitled "In Vitro Activity Profile For Kinases". Typically, the ILK1 preparations were found to exhibit protein phosphotransferase activity in the presence of 50 μM [γ-$^{32}$P]-ATP and 159 μM ILK1 substrate (amino acid sequence: CKRRRLASLR-amide) during a 15 minute reaction at ambient temperature.

Compounds were tested in the following assay for their ability to inhibit the activity of ILK. The desired in vitro potency of a particular inhibitor is such that the compound is useful as a therapeutic agent, i.e. in the nanomolar or micromolar range. See Table 1 infra.

A. Assay Description

Test compounds were lyophilized and stored at −20° C. Stock solutions were made by weighing out the compounds and dissolving them in dimethyl sulfoxide (DMSO) to a standard concentration, usually 20 mM, and stored at −20° C. The compounds were diluted to a starting intermediate concentration of 250 μM in 1% DMSO, then serially diluted across a row of a 96 well plate using serial 2 fold dilution steps. Diluted 100% DMSO was used as a negative control.

5 μL of each compound dilution were robotically pipetted to Costar™ serocluster plates maintaining the same plate layout. All assay mixtures consisted of the following volumes:

5 μL diluted compound
10 μL target enzyme preparation
1 μL substrate
5 μL assay ATP The assay mixtures were then incubated 15 minutes at ambient temperature.

From each assay mixture, 10 μL of assay mixture was spotted onto Millipore Multiscreen-PH™ opaque plates and washed twice for 10 minutes in 1% phosphoric acid. The plates were dried at 40° C. for 30 minutes, then substrate-phosphate complexes were quantitated by scintillation counting. These Millipore plates are in a 96-well format with immobilized P81 phosphocellulose membranes in the wells. Both the phosphorylated and non-phosphorylated form of the substrate bind to the membrane while ATP (unincorporated phosphate) is removed by subsequent wash steps.

B. Calculation of $IC_{50}$

Inhibition of ILK by the test compounds is measured by scintillation counting of the incorporation of radioactive phosphate onto a specific substrate which is immobilized onto a filter paper at the end of the assay. To provide meaningful measurements of inhibition, the assays are performed both in the absence and presence of specific and known inhibitors, and the amount of incorporated radioactivity is compared to provide a baseline measurement.

The "baseline activity" is the amount of radioactivity incorporated in the absence of a target inhibitor. The amount of radioactivity incorporated in the presence of a target inhibitor is called the "sample activity", and the % inhibition is expressed by the following formula:

% inhibition=100−(sample activity/baseline activity*100)

and is usually expressed in conjunction with the compound concentration. By using a range of target inhibitor concentrations, the $IC_{50}$ of an inhibitor is estimated (i.e. the concentration at which enzymatic activity is reduced by 50%). The $IC_{50}$ of various inhibitors against a particular target can be compared, where a lower $IC_{50}$ indicates a more potent inhibitor.

TABLE 1

Inhibition of ILK In Vitro Enzyme Assay

| Chemical Name | $IC_{50}$ avg. value (µM) |
|---|---|
| (4-Benzothiazol-2-yl-1H-pyrazol-3-yl)-[2-(1H-imidazol-4-yl)-ethyl]-amine | 0.2 |
| (4-Benzothiazol-2-yl-2H-pyrazol-3-yl)-methyl-amine | 1.7 |
| [2-(3-Amino-5-methyl-1H-pyrazol-4-yl)-5-fluoro-benzothiazol-6-yl]-methanol | 0.1 |
| [2-(5-Amino-3-methyl-1H-pyrazol-4-yl)-benzothiazol-5-yl]-methanol | 3.7 |
| [2-(5-Amino-3-methyl-1H-pyrazol-4-yl)-benzothiazol-6-yl]-methanol | 0.9 |
| 2-(1H-Pyrazol-4-yl)-benzothiazole | 1.6 |
| 2-(1H-Pyrazol-4-yl)-benzothiazole-6-sulfonic acid amide | 0.5 |
| 2-(3-Amino-1H-pyrazol-4-yl)-5-fluoro-benzothiazole-6-sulfonic acid amide | 0.02 |
| 2-(3-Amino-5-methyl-1H-pyrazol-4-yl)-4,5,6-trifluoro-benzothiazole-7-sulfonic acid amide | 0.07 |
| 2-(3-Amino-5-methyl-1H-pyrazol-4-yl)-5-fluoro-benzothiazole-6-carboxylic acid methyl ester | 0.06 |
| 2-(3-Amino-5-methyl-1H-pyrazol-4-yl)-5-fluoro-benzothiazole-6-sulfonic acid methylamide | 0.04 |
| 2-(3-Amino-5-methyl-1H-pyrazol-4-yl)-benzothiazole-6-carboxylic acid | 1.1 |
| 2-(3-Amino-5-methyl-1H-pyrazol-4-yl)-benzothiazole-6-carboxylic acid methyl ester | 0.3 |
| 2-(3-Amino-5-methyl-1H-pyrazol-4-yl)-benzothiazole-6-sulfonic acid methylamide | 0.07 |
| 2-(3-Amino-5-methyl-1H-pyrazol-4-yl)-benzothiazole-6-sulfonic acid (2,6-dimethyl-pyrimidin-4-yl)-amide | 2.6 |
| 2-(3-Amino-5-methyl-1H-pyrazol-4-yl)-benzothiazole-7-carboxylic acid methyl ester | 0.7 |
| 2-(3-Methyl-1H-pyrazol-4-yl)-benzothiazole | 0.9 |
| 2-(4-Benzothiazol-2-yl-1H-pyrazol-3-yl)-phenol | 4.6 |
| 2-(5-Amino-1H-pyrazol-4-yl)-benzothiazol-6-ylamine | 0.5 |
| 2-(5-Amino-1H-pyrazol-4-yl)-benzothiazole-6-sulfonic acid methylamide | 0.06 |
| 2-(5-Amino-3-methyl-1H-pyrazol-4-yl)-4-fluorobenzothiazole-6-sulfonic acid amide | 0.04 |
| 2-(5-Amino-3-methyl-1H-pyrazol-4-yl)-5-fluoro-benzothiazole-4-sulfonic acid (2-hydroxy-ethyl)-amide | 0.15 |
| 2-(5-Amino-3-methyl-1H-pyrazol-4-yl)-5-fluoro-benzothiazole-6-sulfonic acid amide | 0.007 |
| 2-(5-Amino-3-methyl-1H-pyrazol-4-yl)-5-fluoro-benzothiazole-6-sulfonic acid (2-hydroxy-ethyl)-amide | 0.05 |
| 2-(5-Amino-3-methyl-1H-pyrazol-4-yl)-5-fluoro-benzothiazole-6-sulfonic acid (pyridin-4-ylmethyl)-amide | 0.13 |
| 2-(5-Amino-3-methyl-1H-pyrazol-4-yl)-benzothiazol-5-ol | 0.2 |
| 2-(5-Amino-3-methyl-1H-pyrazol-4-yl)-benzothiazole-5-sulfonic acid methylamide | 1.9 |
| 2-(5-Amino-3-methyl-1H-pyrazol-4-yl)-benzothiazole-6-carboxylic acid amide | 0.3 |
| 2-(5-Amino-3-methyl-1H-pyrazol-4-yl)-benzothiazole-6-sulfonic acid amide | 0.01 |
| 2-(5-Amino-3-methyl-1H-pyrazol-4-yl)-benzothiazole-6-sulfonic acid (2-hydroxy-ethyl)-amide | 0.2 |
| 2-(5-Amino-3-methyl-1H-pyrazol-4-yl)-benzothiazole-6-sulfonic acid (2-methoxy-ethyl)-amide | 0.6 |
| 2-(5-Amino-3-methyl-1H-pyrazol-4-yl)-benzothiazole-6-sulfonic acid 4-fluoro-benzylamide | 4.8 |
| 2-(5-Amino-3-methyl-1H-pyrazol-4-yl)-benzothiazole-6-sulfonic acid (2-thiophen-2-yl-ethyl)-amide | 1.7 |
| 2-(5-Amino-3-methyl-1H-pyrazol-4-yl)-benzothiazole-6-sulfonic acid 4-chloro-benzylamide | 0.9 |
| 2-(5-Amino-3-methyl-1H-pyrazol-4-yl)-benzothiazole-6-sulfonic acid 4-methoxy-benzylamide | 1.0 |
| 2-(5-Amino-3-methyl-1H-pyrazol-4-yl)-benzothiazole-6-sulfonic acid benzylamide | 0.8 |

TABLE 1-continued

Inhibition of ILK In Vitro Enzyme Assay

| Chemical Name | IC$_{50}$ avg. value (μM) |
|---|---|
| 2-(5-Amino-3-methyl-1H-pyrazol-4-yl)-benzothiazole-6-sulfonic acid phenethyl-amide | 0.8 |
| 2-(5-Amino-3-methyl-1H-pyrazol-4-yl)-benzothiazole-6-sulfonic acid [2-(4-amino-phenyl)-ethyl]-amide | 0.2 |
| 2-(5-Amino-3-methyl-1H-pyrazol-4-yl)-benzothiazole-6-sulfonic acid (2-morpholin-4-yl-ethyl)-amide | 3.0 |
| 2-(5-Amino-3-methyl-1H-pyrazol-4-yl)-benzothiazole-6-sulfonic acid (2,2,2-trifluoro-ethyl)-amide | 0.09 |
| 2-(5-Amino-3-methyl-1H-pyrazol-4-yl)-benzothiazole-6-sulfonic acid cyclopropylmethyl-amide | 0.7 |
| 2-(5-Amino-3-methyl-1H-pyrazol-4-yl)-benzothiazole-6-sulfonic acid [2-(3H-imidazol-4-yl)-ethyl]-amide | 0.2 |
| 2-(5-Amino-3-methyl-1H-pyrazol-4-yl)-benzothiazole-6-sulfonic acid 4-amino-benzylamide | 0.6 |
| 2-(5-Amino-3-methyl-1H-pyrazol-4-yl)-benzothiazole-6-sulfonic acid (pyridin-4-ylmethyl)-amide | 0.04 |
| 2-(5-Amino-3-methyl-1H-pyrazol-4-yl)-benzothiazole-6-sulfonic acid (2-dimethylamino-ethyl)-amide | 0.3 |
| 2-(5-Amino-3-methyl-1H-pyrazol-4-yl)-benzothiazole-6-sulfonic acid (3-dimethylamino-propyl)-amide | 3.2 |
| 2-(5-Amino-3-methyl-1H-pyrazol-4-yl)-benzothiazole-6-sulfonic acid (acetic hydrazido) amide | 0.03 |
| 2-(5-Amino-3-methyl-1H-pyrazol-4-yl)-benzothiazole-6-sulfonic acid (phenylhydrazino) amide | 0.9 |
| 2-(5-Amino-3-pyridin-4-yl-1H-pyrazol-4-yl)-benzothiazole-6-sulfonic acid amide | 0.05 |
| 2-(5-Amino-4-benzothiazol-2-yl-1H-pyrazol-3-ylamino)-ethanol | 0.4 |
| 2-(5-Amino-4-benzothiazol-2-yl-2H-pyrazol-3-ylamino)-cyclopentanol | 3.5 |
| 2-{[2-(5-Amino-3-methyl-1H-pyrazol-4-yl)-benzothiazol-6-ylmethyl]-amino}-ethanol | 0.1 |
| 3-(5-Amino-4-benzothiazol-2-yl-1H-pyrazol-3-yl)-propan-1-ol | 0.2 |
| 3-(5-Amino-4-benzothiazol-2-yl-1H-pyrazol-3-ylamino)-propan-1-ol | 0.4 |
| 3-[5-Amino-4-(5-fluoro-6-methoxy-benzothiazol-2-yl)-1H-pyrazol-3-ylamino]-propan-1-ol | 0.5 |
| 3-{[2-(5-Amino-3-methyl-1H-pyrazol-4-yl)-benzothiazol-6-ylmethyl]-amino}-benzenesulfonamide | 0.8 |
| 4-(4-Benzothiazol-2-yl-1H-pyrazol-3-yl)-6-ethyl-benzene-1,3-diol | 1.9 |
| 4-(4-Benzothiazol-2-yl-1H-pyrazol-3-yl)-benzene-1,3-diol | 3.3 |
| 4-(4-Benzothiazol-2-yl-1H-pyrazol-3-yl)-phenol | 3.4 |
| 4-(4-fluorobenzothiazol-2-yl)-5-methyl-2H-pyrazol-3-ylamine | 0.4 |
| 4-(5-Amino-4-benzothiazol-2-yl-1H-pyrazol-3-yl)-butan-1-ol | 1.0 |
| 4-(5-Amino-4-benzothiazol-2-yl-1H-pyrazol-3-ylamino)-butan-1-ol | 1.7 |
| 4-(5-Amino-4-benzothiazol-2-yl-1H-pyrazol-3-ylamino)-butyric acid | 4.3 |
| 4-(5-Amino-4-benzothiazol-2-yl-2H-pyrazol-3-ylamino)-N-thiazol-2-yl-benzenesulfonamide | 3.5 |
| 4-(5-Fluoro-6-methoxy-benzothiazol-2-yl)-5-(2-fluoro-phenyl)-2H-pyrazol-3-ylamine | 4.0 |
| 4-(5-Fluoro-6-methoxy-benzothiazol-2-yl)-5-(2-phenyl-cyclopropyl)-2H-pyrazol-3-ylamine | 2.1 |
| 4-(5-Fluoro-6-methoxy-benzothiazol-2-yl)-5-(3-fluoro-phenyl)-2H-pyrazol-3-ylamine | 2.3 |
| 4-(5-Fluoro-6-methoxy-benzothiazol-2-yl)-5-(3-nitro-phenyl)-2H-pyrazol-3-ylamine | 0.9 |
| 4-(5-Fluoro-6-methoxy-benzothiazol-2-yl)-5-(4-fluoro-phenyl)-2H-pyrazol-3-ylamine | 2.4 |
| 4-(5-Fluoro-6-methoxy-benzothiazol-2-yl)-5-(4-methoxy-phenyl)-2H-pyrazol-3-ylamine | 2.0 |
| 4-(5-Fluoro-6-methoxy-benzothiazol-2-yl)-5-(5-nitro-furan-2-yl)-2H-pyrazol-3-ylamine | 0.3 |
| 4-(5-Fluoro-6-methoxy-benzothiazol-2-yl)-5-furan-2-yl-2H-pyrazol-3-ylamine | 0.04 |
| 4-(5-Fluoro-6-methoxy-benzothiazol-2-yl)-5-isoxazol-5-yl-2H-pyrazol-3-ylamine | 0.1 |
| 4-(5-Fluoro-6-methoxy-benzothiazol-2-yl)-5-methyl-1H-pyrazol-3-ylamine | 0.06 |
| 4-(5-Fluoro-6-methoxy-benzothiazol-2-yl)-5-phenyl-2H-pyrazol-3-ylamine | 2.3 |
| 4-(5-Fluoro-6-methoxy-benzothiazol-2-yl)-5-piperazin-1-yl-2H-pyrazol-3-ylamine | 0.07 |
| 4-(5-Fluoro-6-methoxy-benzothiazol-2-yl)-5-pyridin-4-yl-2H-pyrazol-3-ylamine | 0.2 |
| 4-(5-Fluoro-6-methoxy-benzothiazol-2-yl)-5-thiophen-2-yl-2H-pyrazol-3-ylamine | 0.7 |
| 4-(5-Fluoro-6-methoxy-benzothiazol-2-yl)-N3-[2-(3H-imidazol-4-yl)-ethyl]-1H-pyrazole-3,5-diamine | 0.2 |
| 4-(5-Fluoro-6-methyl-benzothiazol-2-yl)-2H-pyrazol-3-ylamine | 0.05 |

TABLE 1-continued

Inhibition of ILK In Vitro Enzyme Assay

| Chemical Name | IC$_{50}$ avg. value (μM) |
|---|---|
| 4-(5-Fluoro-6-methyl-benzothiazol-2-yl)-5-methyl-2H-pyrazol-3-ylamine | 0.3 |
| 4-(5-Fluoro-benzothiazol-2-yl)-5-methyl-2H-pyrazol-3-ylamine | 0.04 |
| 4-(5-Methoxy-benzothiazol-2-yl)-5-methyl-2H-pyrazol-3-ylamine | 3.7 |
| 4-(5-Trifluoromethyl-benzothiazol-2-yl)-1H-pyrazol-3-ylamine | 1.1 |
| 4-(6-Bromo-5-fluoro-benzothiazol-2-yl)-5-methyl-1H-pyrazol-3-ylamine | 0.2 |
| 4-(6-Bromo-benzothiazol-2-yl)-5-methyl-1H-pyrazol-3-ylamine | 0.4 |
| 4-(6-Chlorobenzothiazol-2-yl)-5-methyl-2H-pyrazol-3-ylamine | 0.3 |
| 4-(6-Dimethylaminomethyl-5-fluoro-benzothiazol-2-yl)-5-methyl-1H-pyrazol-3-ylamine | 0.6 |
| 4-(6-Dimethylaminomethyl-benzothiazol-2-yl)-5-methyl-2H-pyrazol-3-ylamine | 0.2 |
| 4-(6-Fluoro-benzothiazol-2-yl)-1H-pyrazol-3-ylamine | 0.2 |
| 4-(6-Fluoro-benzothiazol-2-yl)-5-methyl-1H-pyrazol-3-ylamine | 0.4 |
| 4-(6-Methanesulfonyl-benzothiazol-2-yl)-5-methyl-2H-pyrazol-3-ylamine | 0.5 |
| 4-(6-Methoxy-benzothiazol-2-yl)-5-methyl-1H-pyrazol-3-ylamine | 0.34 |
| 4-(6-Methoxy-benzothiazol-2-yl)-5-piperazin-1-yl-2H-pyrazol-3-ylamine | 0.2 |
| 4-(6-Nitro-benzothiazol-2-yl)-2H-pyrazol-3-ylamine | 3.4 |
| 4-(7-chloro-4-methoxy-benzothiazol-2-yl)-5-methyl-2H-pyrazol-3-ylamine | 1.0 |
| 4-(7-Chloro-5-fluoro-6-methoxy-benzothiazol-2-yl)-5-methyl-1H-pyrazol-3-ylamine | 0.4 |
| 4-[(5-Amino-4-benzothiazol-2-yl-1H-pyrazol-3-ylamino)-methyl]-benzenesulfonamide | 2.9 |
| 4-[2-(5-Amino-4-benzothiazol-2-yl-1H-pyrazol-3-ylamino)-ethyl]-phenol | 2.9 |
| 4-Benzothiazol-2-yl-1H-pyrazol-3-ylamine | 0.3 |
| 4-Benzothiazol-2-yl-1H-pyrazole-3,5-diamine | 0.7 |
| 4-Benzothiazol-2-yl-5-(3-dimethylamino-propyl)-2H-pyrazol-3-ylamine | 0.2 |
| 4-Benzothiazol-2-yl-5-(3-methylamino-propyl)-2H-pyrazol-3-ylamine | 0.02 |
| 4-Benzothiazol-2-yl-5-(4-dimethylamino-butyl)-2H-pyrazol-3-ylamine | 0.4 |
| 4-Benzothiazol-2-yl-5-(4-methylamino-butyl)-2H-pyrazol-3-ylamine | 0.1 |
| 4-Benzothiazol-2-yl-5-(4-nitro-phenyl)-2H-pyrazol-3-ylamine | 4.0 |
| 4-Benzothiazol-2-yl-5-cyclopropyl-2H-pyrazol-3-ylamine | 0.6 |
| 4-Benzothiazol-2-yl-5-ethyl-1H-pyrazol-3-ylamine | 0.8 |
| 4-Benzothiazol-2-yl-5-furan-2-yl-2H-pyrazol-3-ylamine | 0.1 |
| 4-Benzothiazol-2-yl-5-methyl-1H-pyrazol-3-ylamine | 0.3 |
| 4-Benzothiazol-2-yl-5-methylsulfanyl-1H-pyrazol-3-ylamine | 1.1 |
| 4-Benzothiazol-2-yl-5-phenyl-1H-pyrazol-3-ylamine | 0.9 |
| 4-Benzothiazol-2-yl-5-piperazin-1-yl-2H-pyrazol-3-ylamine | 0.19 |
| 4-Benzothiazol-2-yl-5-piperidin-4-yl-2H-pyrazol-3-ylamine | 0.06 |
| 4-Benzothiazol-2-yl-5-pyridin-3-yl-2H-pyrazol-3-ylamine | 0.6 |
| 4-Benzothiazol-2-yl-5-pyridin-4-yl-2H-pyrazol-3-ylamine | 0.1 |
| 4-Benzothiazol-2-yl-5-pyrrolidin-1-yl-1H-pyrazol-3-ylamine | 3.7 |
| 4-Benzothiazol-2-yl-5-thiophen-2-yl-2H-pyrazol-3-ylamine | 0.9 |
| 4-Benzothiazol-2-yl-N3-(1H-imidazol-2-ylmethyl)-1H-pyrazole-3,5-diamine | 2.5 |
| 4-Benzothiazol-2-yl-N3-(1H-imidazol-2-ylmethylene)-1H-pyrazole-3,5-diamine | 1.0 |
| 4-Benzothiazol-2-yl-N3-(2-dimethylamino-ethyl)-1H-pyrazole-3,5-diamine | 0.5 |
| 4-Benzothiazol-2-yl-N3-(2-ethylamino-ethyl)-1H-pyrazole-3,5-diamine | 0.15 |
| 4-Benzothiazol-2-yl-N3-(2-methoxy-ethyl)-1H-pyrazole-3,5-diamine | 0.7 |
| 4-Benzothiazol-2-yl-N3-(2-pyrrolidin-1-yl-ethyl)-1H-pyrazole-3,5-diamine | 1.9 |
| 4-Benzothiazol-2-yl-N3-(3-dimethylamino-propyl)-1H-pyrazole-3,5-diamine | 0.3 |
| 4-Benzothiazol-2-yl-N3-(3-imidazol-1-yl-propyl)-1H-pyrazole-3,5-diamine | 0.5 |
| 4-Benzothiazol-2-yl-N3-[2-(1H-indol-3-yl)-ethyl]-1H-pyrazole-3,5-diamine | 3.3 |
| 4-Benzothiazol-2-yl-N3-piperidin-4-ylmethyl-1H-pyrazole-3,5-diamine | 2.7 |
| 4-Benzothiazol-2-yl-N5-(2-morpholin-4-yl-ethyl)-1H-pyrazole-3,5-diamine | 1.5 |
| 4-Benzothiazol-2-yl-N5-ethyl-1H-pyrazole-3,5-diamine | 1.7 |
| 4-Benzothiazol-2-yl-N5-pyridin-3-ylmethyl-1H-pyrazole-3,5-diamine | 2.9 |
| 5-(2-Chloro-pyridin-3-yl)-4-(5-fluoro-6-methoxy-benzothiazol-2-yl)-2H-pyrazol-3-ylamine | 3.4 |
| 5-(3-Amino-propyl)-4-benzothiazol-2-yl-2H-pyrazol-3-ylamine | 0.01 |
| 5-(4-Amino-phenyl)-4-benzothiazol-2-yl-2H-pyrazol-3-ylamine | 0.1 |
| 5-Cyclopropyl-4-(5-fluoro-6-methoxy-benzothiazol-2-yl)-2H-pyrazol-3-ylamine | 1.0 |
| 5-Methyl-4-(4,5,6-trifluoro-benzothiazol-2-yl)-1H-pyrazol-3-ylamine | 0.2 |
| 5-Methyl-4-(5-trifluoromethylbenzothiazol-2-yl)-1H-pyrazol-3-ylamine | 2.8 |
| 5-Methyl-4-(6-methylaminomethyl-benzothiazol-2-yl)-2H-pyrazol-3-ylamine | 0.5 |
| 5-Methyl-4-(6-morpholin-4-ylmethyl-benzothiazol-2-yl)-2H-pyrazol-3-ylamine | 0.5 |
| 5-Methyl-4-(6-pyrrolidin-1-ylmethyl-benzothiazol-2-yl)-2H-pyrazol-3-ylamine | 0.9 |
| 5-Methyl-4-[6-(4-methyl-piperazin-1-ylmethyl)-benzothiazol-2-yl]-2H-pyrazol-3-ylamine | 5.0 |

TABLE 1-continued

Inhibition of ILK In Vitro Enzyme Assay

| Chemical Name | IC$_{50}$ avg. value (μM) |
|---|---|
| 5-Methyl-4-[6-(4-methyl-piperazine-1-sulfonyl)-benzothiazol-2-yl]-2H-pyrazol-3-ylamine | 4.9 |
| N-[2-(5-Amino-3-methyl-1H-pyrazol-4-yl)-benzothiazol-6-yl]-acetamide | 0.4 |
| N-[2-(5-Amino-4-benzothiazol-2-yl-1H-pyrazol-3-ylamino)-ethyl]-acetamide | 1.1 |
| N-[4-(5-Amino-4-benzothiazol-2-yl-1H-pyrazol-3-yl)-phenyl]-hydroxylamine | 1.6 |
| N-{2-[2-(5-Amino-3-methyl-1H-pyrazol-4-yl)-benzothiazole-6-sulfonylamino]-ethyl}-acetamide | 0.7 |
| N-{2-[5-Amino-4-(5-fluoro-6-methoxy-benzothiazol-2-yl)-1H-pyrazol-3-ylamino]-ethyl}-acetamide | 1.8 |
| N3-(2-Amino-ethyl)-4-benzothiazol-2-yl-1H-pyrazole-3,5-diamine | 0.02 |
| N3-(2-Dimethylamino-ethyl)-4-(5-fluoro-6-methoxy-benzothiazol-2-yl)-1H-pyrazole-3,5-diamine | 0.3 |
| N3-(3-Dimethylamino-propyl)-4-(5-fluoro-6-methoxy-benzothiazol-2-yl)-1H-pyrazole-3,5-diamine | 0.2 |
| N3-(4-Amino-phenyl)-4-benzothiazol-2-yl-1H-pyrazole-3,5-diamine | 5.0 |
| N3-[2-(3H-Imidazol-4-yl)-ethyl]-4-(6-methoxy-benzothiazol-2-yl)-1H-pyrazole-3,5-diamine | 0.6 |

Example 40

Cytotoxicity Assay

This procedure was used to assess the effects compounds have on various cell lines with respect to cell viability. Cell viability is quantified using calcein AM and measuring its conversion to a fluorescent product (calcein) with a fluorimeter.

The principle of this assay is based on the presence of ubiquitous intracellular esterase activity found in live cells. By enzymatic reaction of esterase, non-fluorescent cell-permeant calcein AM is converted to the intensely fluorescent calcein. The polyanionic dye calcein is retained within live cells, producing a green fluorescence in live cells. It should be noted that calcein AM is susceptible to hydrolysis when exposed to moisture. Therefore, prepare aqueous working solutions containing calcein AM immediately prior to use, and use within about one day.

A kit available to do this assay is "LIVE/DEAD® Viability/Cytotoxicity Kit (L-3224)" by Molecular Probes.

Cells were collected from tissue culture flasks and trypsinized, centrifuged, resuspended and counted. Cells were seeded to obtain 80-90% confluence (for normal cells, 10,000 cells/well (8000 cells/well for HUVEC cells)). A cell concentration of 110,000 cells/mL (88,000 cells/well for HUVEC cells) is prepared as 90 μL volume is used per well.

Using an 8-channel multi-dispense pipettor, cells were seeded in the central rows of the plate (Nunclon™ 96 well flat-bottom plate), leaving the peripheral top and bottom rows with same volume of media only. The plates were incubated at 37° C., 5% CO$_2$ overnight for approximately 24 hours.

For test compounds, cell culture media (e.g., RPMI+10% FBS), 10× compound solution of final desired concentration from 20 mM stock compounds was prepared. Ten μl of this 10× compound solution is added to the 90 μL of cells already present in the 96 well plates and a known cytotoxic compound from previous testing is used as a positive control. The negative control is 100% DMSO diluted to the same factor as the compounds.

The plates are incubated at 37° C. for approximately 24 hours, and media is aspirated after plates are spun at 2400 rpm for 10 min at ambient temperature. 100 μL of 1×DPBS (without CaCl$_2$, without MgCl$_2$ (GibcoBRL, cat#14190-144)) is added to each well.

The calcein AM solution is prepared by adding 50 μg of calcein AM crystal (m.w.=994.87 g/mol, Molecular Probes, Eugene, Oreg.) and anhydrous DMSO (Sigma Aldrich) to make 1 mM stock and diluting stock to 2× the final desired concentration in 1×DPBS just before the assay. 100 μL is then added to the 100 μL of DPBS in the wells, and the plates are incubated at ambient temperature for 30 minutes. Fluorescence data was read and recorded (Fluoroskan Ascent® FL fluorimeter (excitation ~485 nm, emission ~527 nm)).

The values for replicates (usually six) are averaged and % inhibition is calculated as follows:

% inhibition=100−[(AVG treatment−AVG positive control)/(AVG negative control−AVG positive control)*100]

On cell lines HUVEC, HS27, and LL-86, cytotoxicity of 62 representative compounds in Table 1, at 5 μM and 25 μM concentration, ranged from zero percent to 20%. Most of the measurements were less than 10%.

Example 41

Cell Invasion in Matrigel™ Extracellular Matrix Extract

This procedure is used to assess the compound effect on the tumor cell invasion through Matrigel™-coated Fluoroblok™ inserts. Invasion allows tumor cells to spread to sites other that the primary tumor. The following assay uses this system to assess compound effects on the anti-tumor cell invasion through layer of Matrigel™ extracellular matrix.

The cell lines used are HT 1080 (ATCC, Cat# CCL-121), DU-145 (ATCC, Cat# HTB-81), PC3 (ATCC, Cat# CRL-1435) or B16F1 (ATCC, Cat# CRL-6323).

The invasion test system (BD Bioscience's BioCoat™ FluoroBlok™ Invasion System including BD BioCoat™ Matrigel™ Invasion Chambers with the fluorescence blocking membrane FluoroBlok™ 24-Multiwell Insert System™) is removed from the package from −20° C. storage and allowed to warm to ambient temperature. PBS is added to the interior of the inserts and they are allowed to rehydrate for 2 hours at 37° C. The medium is then removed and 450 μL cell suspensions of tumor cells (grown to 50-70% confluence, trypsinized, and resuspended in medium without serum at $1\times10^6$/mL) is added to the top chamber. Test compounds are added to the top chamber at 10× the desired final concentration in 50 μL volumes. DMSO acts as the control.

Then 750 μL of medium containing 50% fresh growth medium with 10% FBS and 50% NIH 3T3-conditioned medium is added to each of the bottom wells. The invasion system is incubated for 24 to 48 hours at 37° C., in a 5% $CO_2$ atmosphere.

Following incubation, the insert plate is transferred into a second 24-well plate containing 0.5 mL of 5 μg/mL calcein AM in Hanks buffered salt solution (HBSS), and plates are incubated for 1 hour at 37° C., 5% $CO_2$.

Fluorescence data indicating cell invasion is read in a Fluoroskan Ascent™ FL (LabSystems) with bottom reading at excitation/emission wavelength of 485/538 nm.

Data is expressed as fluorescence units (FU) from the sum of middle 25 areas per 24-well or as percentage of invasion inhibition by following formula: % of invasion inhibition=100−FU of compound treated cell invasion/FU of DMSO treated cell invasion*100.

Twenty-one representative compounds from Table 1 were tested in this assay, and the percent of inhibition ranged from 20 to 80%. The compounds are thus useful to prevent metastasis in cancer and tissue remodeling.

Example 42

Inflammatory Responses are Modulated in the Presence of Compounds

Establishment of Inflammation Assay Panel.

Macrophages are important elements of innate immunity to infection and are among the first cell type in the immune response to be exposed to and activated by infectious agents. IFN-γ and LPS are potent activators of macrophages, priming them for a variety of biological effects. IFN-γ, initially secreted by NK and T cells in response to infection, converts macrophages from a resting to an activated state, priming them for antimicrobial activity manifested by increased killing of intracellular pathogens, and antigen processing and presentation to lymphocytes. The action of IFN-γ is synergized with the LPS second messenger, enhancing the stimulation of macrophages through the activation of NF-κB, that results in the transcriptional up-regulation of a number of genes involved in the cell-mediated immune response, including inducible nitric oxide synthase (iNOS). Activated macrophages are qualitatively different from quiescent macrophages. These differences are typically observed by an increased proliferation index, up-regulated expression of MHC-II, and production of various bioactive molecules. The latter biological effects are mediated by nitric oxide (NO) release and increased production of pro-inflammatory cytokines (IL-6, TNF-α, IL-1). Primary macrophages derived from Balb/c and RAW 264.7 cells (Balb/c background) were used to establish in vitro inflammatory models with fast and reliable readouts.

Materials and Methods

1. Reagents.

The iNOS inhibitor NG-monomethyl-L-arginine (L-NMMA) and murine rIFN-γ were purchased from Calbiochem (San Diego, Calif.). Protein-free, phenol/water-extracted LPS (from *E. coli* serotype 0111:B4 0127:B8), Zymosan A, dexamethasone and hydrocortisone, sulfanilamide and N-(1-naphthyl)-ethylenediamine, were purchased from Sigma (St. Louis, Mo.). Human recombinant vascular endothelial growth factor (VEGF) was purchased from R&D Systems (Minneapolis, Minn.). Anti-murine iNOS/NOS type II antibodies were obtained from Transduction Laboratories (Lexington, Ky.). Female, 6-12 wk of age, BALB/c mice were purchased from Harlan Inc. (Indianapolis, Ind.) and maintained in compliance with the Canadian Council on Animal Care standards.

2. Isolation of Primary Mouse Macrophages.

Peritoneal exudate macrophages were isolated by peritoneal lavage with ice-cold sterile physiological saline 24 hours after intraperitoneal injection of BALB/c mice with 0.5 mL of sterile Zymosan A (1 mg/0.5 mL 0.9% saline). Cells were washed, resuspended in RPMI 1640 supplemented with 1 mM D-glucose, 1 mM sodium pyruvate, 100 units/mL penicillin, 100 μg/mL streptomycin, and 5% FBS.

3. Inhibition of IL-12 Release Determination

Murine primary macrophage are activated following incubation with LPS in the presence of sub-optimal doses of IFN-γ. Upon activation, macrophages participate actively in the onset of inflammation by releasing bioactive molecules that amplify the initial inflammatory response. Stimulated macrophages demonstrate up-regulated expression of MHC-II receptors, increased release of NO and produce a number of pro-inflammatory cytokines including IL-12, IL-6, TNF-α, MIP-1α and MIP-1β.

Briefly, IL-12 levels in the supernatants from stimulated macrophages were determined with PharMingen's OptEIA™ ELISA set developed using an anti-mouse IL-12 antibody pair and mouse rIL-12 standard (PharMingen). Maxisorp™ F16 multiwell strips (Nunc, Roskilde, Denmark) were coated with anti-mouse IL-12 capture Ab (at recommended concentration) in 0.1 M $NaHCO_3$, pH 9.5, 100 μL/well, overnight at 4° C. Plates were washed 3× with 0.05% Tween 20 in PBS (PBST) and blocked for 1 h with 200 mL/well of 10% FCS in PBS (blocking and dilution buffer). Plates were washed 3× with PBST and duplicate samples (100 μL/well) or standards (100 μL/well) in diluent buffer were incubated for 2 h. Plates were washed five times with PBST and incubated with biotinylated anti-mouse IL-12 and avidin-horseradish peroxidase (HRP) conjugate (at concentrations recommended by the manufacturer) for 1 h. Plates were washed 7× with PBST and 100 μl of 3,3',5,5'-tetramethylbenzidine substrate solution was added to each well. After 15-30 minute incubation at room temperature, colour development was terminated by adding 50 μL of 2 N $H_2SO_4$. Absorbance was read at 450 nm with an EL 312e microplate reader. The detection limit for IL-12 was 15.6 pg/ml.

For discussion of measuring Interleukin-12 in tissue culture supernatants, see, e.g., Skeen M. J., Miller M. A., Shinnick T. M., et al. *J Immunol*. (1996) 156(3):1196-206. Results for the IL-12 study are shown in Table 2 for representative compounds.

4. Inhibition of TNFα Release Determination:

Murine primary macrophage will get activated following incubation with LPS in the presence of sub-optimal doses of IFN-γ. Upon activation, macrophages participate actively in the onset of inflammation by releasing bioactive molecules that amplify the initial inflammatory response Activated macrophages demonstrate up-regulated expression of MHC-II receptors, increased release of NO and produce a number of pro-inflammatory cytokines including TNF-α.

TNF-α levels in the supernatants from stimulated macrophages were determined with PharMingen's OptEIA TNF-α kit (PharMingen). The experiment was performed at room temperature, about 21° C., unless otherwise stated.

The microwells (F8 MaxiSorp™ Loose/Nunc-Immuno Module; Gibco/BRL) were coated with 100 μl/well of capture antibody (at the recommended concentration) and incubated overnight at 4° C. The plates were washed with 100 μl/well of wash buffer (0.05% Tween-20 in 1×PBS) and blocked for 1 hour with 200 μl/well assay diluent buffer (10% FBS in 1×PBS). Next, the solution was removed and the plates were washed 5× with wash buffer.

The TNF-α analysis was initiated by adding duplicate samples (100 μl/well) or standards (100 μl/well) in diluent buffer which were incubated for 2 h. The solution was removed and the plates washed 5× with wash buffer. Enzyme reagent (100 μl) containing biotinylated mouse TNF-α monoclonal antibody and avidin-horseradish peroxidase conjugate (at concentrations recommended by the manufacturer) was added to each well. The plate was incubated for 1 hour, the solution removed, and the plates washed 7× with wash buffer. Finally, 3,3',5,5'-tetramethylbenzidine (TMB) substrate solution (100 μl) was added to each well and the plate incubated in the dark for 15 to 30 minutes. Colour development was terminated by adding 50 μl of 2N $H_2SO_4$. The optical density was measured at 450 nm with an EL 312e microplate reader. The detection limit for TNF-α was 15.6 pg/ml.

The data is represented as a percentage of TNF-α inhibition by the following formula: % TNF-α inhibition=100−(AVG treatment/AVG DMSO control)*100.

For discussion of measuring Tumour Necrosis Factor (TNF-α tissue culture supernatants, see e.g. Drew, P. D., and J. Chavis, "Inhibition of Microglial Cell Activation by Cortisol" *Brain Research Bulletin*. (2000) 52(5):391-396; Drew, P. D., and J. Chavis "Female Sex Steroids: Effects Upon Microglial Cell Activation" *J. Neuroimmunology*. (2000) 111(1-2): 77-85.

Representative compounds were tested in this assay, and the results are shown in Table 2.

5. Inhibition of IFNγ Release Determination:

T-lymphocytes obtained from mice spleens are a suitable sample for studying the activation properties of this immunologically important cell type. T-lymphocytes are the main regulators for inflammation. Concanavalin A (ConA) is an effective activator of T-lymphocytes, which allows T-lymphocytes to proliferate and produce inflammatory cytokines, such as Interferon (IFNγ) and regulatory cytokines, such as Interleukin 10 (IL-10).

Isolation of T-Lymphocytes from Mouse Spleens

Spleens were removed from Balb/c mice place in 3 ml serum-free RPMI 1640 (Gibco/BRL) and stored on ice until ready for use. The spleens were transferred onto mesh screen containing 10 ml of ice cold RPMI-5 (1× sodium pyruvate and 5% FBS) and gently ground with a pestle. The cell suspensions were centrifuged at 1500 rpm for 6 minutes at 4° C. The red blood cells were lysed by adding 2 ml of lysis buffer for 1 minute and the reaction terminated quickly by adding 10 ml of RPMI-5. The supernatant was discarded and the pellet washed two additional times. The cells were resuspended in RPMI-5 and the cell suspensions combined. The cells were counted and their concentration was adjusted to $2.8 \times 10^6$ cells/ml using RPMI-5.

Stimulation and Treatment of Splenocytes

The isolated splenocytes (180 μl/ml of $2.8 \times 10^6$ cells/ml) were added to 96-well plates for a final concentration of $5 \times 10^5$ cell/well. The working concentration of ConA was 2.5 μl/ml. A 20× working concentration of Concanavalin A was 50 μl/ml was prepared using RPMI-5. The test compounds, dimethylsulfoxide (DMSO) negative vehicle control and staurosporine positive control were diluted twenty times using RPMI-5. Ten μL each of DMSO and staurosporine were combined with 180 μl of medium containing splenocytes in the wells, and 10 μl of 50 μg/ml ConA was immediately added. Medium without ConA was added to the control wells. To test the compounds on unstimulated splenocytes, 10 μl of RPMI-5 was added to each well in place of the ConA solution. The plates were incubated at 37° C. in 5% $CO_2$ in humidified conditions overnight (18-24 hours) for INFγ.

Enzyme Immunoassays for Mouse INFγ

At the completion of the stimulation described above, the plates were spun at 2000 rpm for 10 minutes. The supernatants (100 μl) from each well were transferred to fresh plates for INFγ analysis by ELISA.

INFγ levels in the supernatants from stimulated lymphocytes were determined with PharMingen's OptEIA™ INFγ Kit (PharMingen) according to manufacturer's directions. The data, shown in Table 2 infra, is represented as a percentage of INFγ inhibition by the following formula:

% INFγ inhibition=100−(AVG treatment/AVG DMSO control)*100.

6. Measuring Cytotoxicity by MTS Staining

An assessment of cell viability subsequent to compound exposure was determined quantitatively by employing a cytotoxic assay using the soluble tetrazolium salt [3-(4,5-dimethylthiazol-2-yl)-5-(3-carboxymethoxyphenyl)-2-(4-sulfophenyl)-2H-tetrazolium, inner salt] (MTS). The MTS solution was made fresh and under low light. The electron coupling reagent phenazine methosulfate (PMS) was added at the time of the assay. Twenty μL of MTS solution per 100 μl of tissue culture medium was added to each well. The plates were incubated 37° C. for 4 hours for unstimulated and 18-24 ConA stimulated splenocytes. The absorbance was read at 490 nm wavelength. A kit available to do this assay is "Cell-Titer 96® AQ Kit $AQ_{ueous}$ Kit (G5421)" by Promega.

The values for four replicates are averaged and % inhibition is calculated at follows: % survival=100−[(AVG treatment−AVG positive control)/(AVG negative control−AVG positive control)*100]. Results are shown in Table 2.

For discussion of measuring INFγ in tissue culture supernatants, see e.g., Uzonna, J., Kaushik, R., Gordon, J., and Tabel, H. *J. Immuno*. (1998), 161:5507-5515; Xi S., Cohen D., and Chen L. *J. of Lipid Research*. (1998), 39, 1677-1687. Product Information, "LIVE/DEAD® Viability/Cytotoxicity Kit (L-3224)" by Molecular Probes (revised 24 Jan. 2001).

7. Inhibition of MCP-1 Release

The activation of endothelial cells by pro-inflammatory cytokine TNF-α leads to the production of several chemokines. The release of these chemokines play an important role in leukocyte trafficking and extravasation of leukocytes into tissue during inflammation. MCP-1 and IL-8 are among the chemokines released upon stimulation of human endothelial cells (HUVECs) by TNFα, and contribute to migration of monocytes to the sites of inflammation. Cells should not be passaged more than 6 times.

Cells were maintained and grown in tissue culture flasks (T75) in endothelial cell growth medium (EGM, Clonetics) containing 5 additional supplements (EGM-5) in medium [human recombinant endothelial growth factor (hEGF), hydrocortisone (HC), bovine brain extract (BBE), fetal bovine serum (FBS) and Gentamycin (GA)] incubated at 37° C., 5% $CO_2$. The cells should be propagated a maximum of 20 passages.

Cells were trypsinized (0.25%), collected from the tissue culture flasks, centrifuged, resuspended in EGM-5, and counted. The cell concentration was adjusted to $2.2 \times 10^4$ cells/ml with EGM-5 medium. The HUVEC were seeded at 180 μl of $2.2 \times 10^4$ cells/ml into 96-well plates for a final seeding density of 4,000 cells/well. The plates were incubated overnight at 37° C., 5% $CO_2$ to enable the cells to attach and grow.

The working concentration of TNFα was 1,000 pg/ml. A twenty times working concentration of TNFα was 20,000 pg/ml was prepared using EGM-5. The test compounds, DMSO negative vehicle control and staurosporine positive control were diluted 20× using EGM-5. Ten μL each of the compounds, DMSO and staurosporine were combined with 180 μl of medium containing HUVEC cells. Immediately following the addition of the compounds, 10 μl of 50 μg/ml TNFα was added to the wells. Medium without TNFα was added to the control wells. To test the compounds on unstimulated HUVEC cells, 10 μl of EGM-5 was added to each well in place of the TNFα solution. The plates were incubated at 37° C. in 5% $CO_2$ in humidified conditions overnight (18-24 hours) for TNFα.

At the completion of the stimulation, the plates were spun at 2000 rpm for 10 minutes. The supernatants from each well were transferred to fresh plates for MCP1 analysis by ELISA.

TNFα levels in the supernatants from stimulated lymphocytes were determined with PharMingen's OptEIA™ MCP1 Kit (PharMingen) according to manufacturer's instructions. The optical density was measured at 450 nm with an EL 312e microplate reader. The detection limit for MCP1 was 15.6 pg/ml.

The data is represented as a percentage of MCP1 inhibition by the following formula: % MCP1 inhibition=100−(AVG treatment/AVG DMSO control)*100. Results are shown in Table 2.

For discussion of measuring MCP1 in tissue culture supernatants, see e.g., Kalogeris T. J., Laroux F. S., Cockrell A. et al. *Am J. Physiol.* 276 (4 Pt 1):C856-864; Instructions provided by PharMingen OptEIA human MCP-1 set (PharMingen, Cat#555179).

Measuring cytotoxicity by MTS staining was performed as above.

The values of replicates are averaged and % inhibition is calculated as follows: % survival=100−[(AVG treatment−AVG positive control)/(AVG negative control−AVG positive control)*100].

Results are shown in Table 2.

TABLE 2

| | IC$_{50}$ of Compounds on Stimulated Macrophages and Splenocytes | | | | | |
|---|---|---|---|---|---|---|
| Chemical Name | IFNg on ConA 1° splenocytes (μM) | Survival of ConA 1° splenocytes | TNFa on macrophages (μM) | IL-12 on macrophages (μM) | Survival of macrophages | MCP1 on HUVECS (μM) |
| (4-Benzothiazol-2-yl-1H-pyrazol-3-yl)-[2-(1H-imidazol-4-yl)-ethyl]-amine | 8.4 uM | >25 | 11.76 uM | 8.1 uM | 14.5 uM | 21.3 uM |
| [2-(3-Amino-5-methyl-1H-pyrazol-4-yl)-5-fluoro-benzothiazol-6-yl]-methanol | 2.026 | >25 | | | | |
| 2-(1H-Pyrazol-4-yl)-benzothiazole-6-sulfonic acid amide | 10.3 uM | >25 | | | | |
| 2-(3-Amino-1H-pyrazol-4-yl)-5-fluoro-benzothiazole-6-sulfonic acid amide | 2.126 | >25 | | | | |
| 2-(3-Amino-5-methyl-1H-pyrazol-4-yl)-4,5,6-trifluoro-benzothiazole-7-sulfonic acid amide | 1.9 uM | 10.2 uM | | | | |
| 2-(3-Amino-5-methyl-1H-pyrazol-4-yl)-5-fluoro-benzothiazole-6-carboxylic acid methyl ester | 1.03 | >25 | | | | |
| 2-(3-Amino-5-methyl-1H-pyrazol-4-yl)-5-fluoro-benzothiazole-6-sulfonic acid methylamide | .368 uM | 11.6 uM | | | | |
| 2-(3-Amino-5-methyl-1H-pyrazol-4-yl)-benzothiazole-6-sulfonic acid methylamide | 0.8 uM | 23.0 | 1.5 | 1.6 | 6.4 | 4.2 |
| 2-(3-Methyl-1H-pyrazol-4-yl)-benzothiazole | 21.4 uM | N | >25 | 12.4 | >25 | >25 |
| 2-(5-Amino-1H-pyrazol-4-yl)-benzothiazole-6-sulfonic acid methylamide | 2.461 | >25 | | | | |
| 2-(5-Amino-3-methyl-1H-pyrazol-4-yl)-4-fluorobenzothiazole-6-sulfonic acid amide | 3.2 uM | >25 | 6.6 uM | 11.7 uM | >25 | >25 |
| 2-(5-Amino-3-methyl-1H-pyrazol-4-yl)-5-fluoro-benzothiazole-4-sulfonic acid (2-hydroxy-ethyl)-amide | 8.9 uM | >25 | 5.204 uM | 12.4 uM | >25 | >25 |
| 2-(5-Amino-3-methyl-1H-pyrazol-4-yl)-5-fluoro-benzothiazole-6-sulfonic acid amide | 1 uM | 15.1 uM | .9 uM | 2.7 uM | 6.7 uM | 2.7 uM |

TABLE 2-continued

IC$_{50}$ of Compounds on Stimulated Macrophages and Splenocytes

| Chemical Name | IFNg on ConA 1° splenocytes (μM) | Survival of ConA 1° splenocytes | TNFa on macrophages (μM) | IL-12 on macrophages (μM) | Survival of macrophages | MCP1 on HUVECS (μM) |
|---|---|---|---|---|---|---|
| 2-(5-Amino-3-methyl-1H-pyrazol-4-yl)-5-fluoro-benzothiazole-6-sulfonic acid (2-hydroxy-ethyl)-amide | 3.4 uM | >25 | 2.0 uM | 4.8 uM | 14.597 uM | 9.0 uM |
| 2-(5-Amino-3-methyl-1H-pyrazol-4-yl)-5-fluoro-benzothiazole-6-sulfonic acid (pyridin-4-ylmethyl)-amide | 3.3 uM | 14.8 uM | 4.4 uM | 6.9 uM | 23.4 uM | 11.7 uM |
| 2-(5-Amino-3-methyl-1H-pyrazol-4-yl)-benzothiazol-5-ol | 11.2 uM | >25 | 7.6 uM | 5.5 uM | >25 | N |
| 2-(5-Amino-3-methyl-1H-pyrazol-4-yl)-benzothiazole-6-carboxylic acid amide | 4.7 uM | >25 | 8.0 uM | 9.6 uM | >25 | 16.2 uM |
| 2-(5-Amino-3-methyl-1H-pyrazol-4-yl)-benzothiazole-6-sulfonic acid (2-methoxy-ethyl)-amide | 6.9 uM | N | | 10.6 uM | >25 | 14.2 uM |
| 2-(5-Amino-3-methyl-1H-pyrazol-4-yl)-benzothiazole-6-sulfonic acid [2-(4-amino-phenyl)-ethyl]-amide | 5.4 uM | >25 | 21.7 uM | 7.8 uM | >25 | 14.5 uM |
| 2-(5-Amino-3-methyl-1H-pyrazol-4-yl)-benzothiazole-6-sulfonic acid (pyridin-4-ylmethyl)-amide | 1.5 uM | 3.8 uM | 3.3 uM | 2.1 uM | 9.7 uM | 6.3 uM |
| 2-(5-Amino-3-methyl-1H-pyrazol-4-yl)-benzothiazole-6-sulfonic acid amide | 2.8 uM | >25 | 3.9 | 3.4 | 7.0 | 12.4 |
| 2-(5-Amino-3-methyl-1H-pyrazol-4-yl)-benzothiazole-6-sulfonic acid (2,2,2-trifluoro-ethyl)-amide | 3.7 uM | 23.1 uM | 5.6 uM | 3.0 uM | 14.7 uM | 5.9 uM |
| 2-(5-Amino-3-methyl-1H-pyrazol-4-yl)-benzothiazole-6-sulfonic acid (2-hydroxy-ethyl)-amide | 3.5 uM | >25 | 6.13 uM | 5.8 uM | 14.8 uM | 11.9 uM |
| 2-(5-Amino-3-methyl-1H-pyrazol-4-yl)-benzothiazole-6-sulfonic acid (2-dimethylamino-ethyl)-amide | 10.8 uM | >25 | 7.9 uM | 5.1 uM | >25 | 14.9 uM |
| 2-(5-Amino-3-pyridin-4-yl-1H-pyrazol-4-yl)-benzothiazole-6-sulfonic acid amide | 11.7 uM | >25 | 13.2 uM | 17.7 uM | >25 | >25 |
| 2-{[2-(5-Amino-3-methyl-1H-pyrazol-4-yl)-benzothiazol-6-ylmethyl]-amino}-ethanol | 8.1 uM | 20.1 uM | | | | |
| 3-(5-Amino-4-benzothiazol-2-yl-1H-pyrazol-3-yl)-propan-1-ol | 10.3 uM | N | >25 | 14.0 uM | N | ~25 |
| 3-(5-Amino-4-benzothiazol-2-yl-1H-pyrazol-3-ylamino)-propan-1-ol | 9.4 uM | >25 | 18.2 uM | 10.6 uM | >25 | 17.3 uM |
| 4-(5-Fluoro-6-methoxy-benzothiazol-2-yl)-5-isoxazol-5-yl-2H-pyrazol-3-ylamine | 2.028 | 22.803 | | | | |
| 4-(5-Fluoro-6-methoxy-benzothiazol-2-yl)-5-methyl-1H-pyrazol-3-ylamine | 1.9 uM | 24.5 uM | 10.9 uM | 5.2 uM | >25 | 5.6 uM |
| 4-(5-Fluoro-6-methoxy-benzothiazol-2-yl)-5-piperazin-1-yl-2H-pyrazol-3-ylamine | 6.1 uM | 17.5 uM | 14.7 uM | 23.4 uM | >25 | 10.9 uM |
| 4-(5-Fluoro-6-methoxy-benzothiazol-2-yl)-5-pyridin-4-yl-2H-pyrazol-3-ylamine | 1.4 uM | >25 | >25 | 7.7 uM | >25 | >25 |

TABLE 2-continued

IC$_{50}$ of Compounds on Stimulated Macrophages and Splenocytes

| Chemical Name | IFNg on ConA 1° splenocytes (μM) | Survival of ConA 1° splenocytes | TNFa on macrophages (μM) | IL-12 on macrophages (μM) | Survival of macrophages | MCP1 on HUVECS (μM) |
|---|---|---|---|---|---|---|
| 4-(5-Fluoro-6-methoxy-benzothiazol-2-yl)-N3-[2-(3H-imidazol-4-yl)-ethyl]-1H-pyrazole-3,5-diamine | 16.6 uM | >25 | | | | |
| 4-(5-Fluoro-6-methyl-benzothiazol-2-yl)-2H-pyrazol-3-ylamine | >25 | >25 | | | | |
| 4-(5-Fluoro-6-methyl-benzothiazol-2-yl)-5-methyl-2H-pyrazol-3-ylamine | 7.822 | >25 | | | | |
| 4-(5-Fluoro-benzothiazol-2-yl)-5-methyl-2H-pyrazol-3-ylamine | 10.3 uM | 22.6 uM | 10.7 uM | 5.0 uM | 20.7 uM | 18.5 uM |
| 4-(6-Chlorobenzothiazol-2-yl)-5-methyl-2H-pyrazol-3-ylamine | 5.6 uM | >25 | >25 | 7.6 uM | 16.7 uM | 7.3 uM |
| 4-(6-Dimethylaminomethyl-5-fluoro-benzothiazol-2-yl)-5-methyl-1H-pyrazol-3-ylamine | 2.351 | >25 | | | | |
| 4-(6-Dimethylaminomethyl-benzothiazol-2-yl)-5-methyl-2H-pyrazol-3-ylamine | 1.5 uM | 19.1 uM | | | | |
| 4-(6-Fluoro-benzothiazol-2-yl)-1H-pyrazol-3-ylamine | 11.6 uM | N | >25 | 13.9 uM | >25 | ~25 |
| 4-(6-Methoxy-benzothiazol-2-yl)-5-methyl-1H-pyrazol-3-ylamine | 2.8 uM | >25 | 18.5 | 10.1 | 21.1 | 24.5 |
| 4-(6-Methoxy-benzothiazol-2-yl)-5-piperazin-1-yl-2H-pyrazol-3-ylamine | 5.9 uM | 20.5 uM | | | | |
| 4-Benzothiazol-2-yl-1H-pyrazol-3-ylamine | 12.6 uM | N | | 7.6 | | |
| 4-Benzothiazol-2-yl-5-(3-dimethylamino-propyl)-2H-pyrazol-3-ylamine | 13 uM | ~25 | | | | |
| 4-Benzothiazol-2-yl-5-(3-methylamino-propyl)-2H-pyrazol-3-ylamine | 9.1 uM | 24.6 uM | | | | 14.8 uM |
| 4-Benzothiazol-2-yl-5-(4-dimethylamino-butyl)-2H-pyrazol-3-ylamine | 16.4 uM | 23.6 uM | | | | |
| 4-Benzothiazol-2-yl-5-(4-methylamino-butyl)-2H-pyrazol-3-ylamine | 11.3 uM | ~25 | | | | |
| 4-Benzothiazol-2-yl-5-piperazin-1-yl-2H-pyrazol-3-ylamine | 7.9 uM | 22.112 uM | >25 | 16.1 uM | >25 | 16.2 uM |
| 4-Benzothiazol-2-yl-5-pyridin-4-yl-2H-pyrazol-3-ylamine | 2.3 uM | >25 | 5.1 | >25 | >25 | 18.5 |
| 4-Benzothiazol-2-yl-N3-(3-dimethylamino-propyl)-1H-pyrazole-3,5-diamine | 5.7 uM | >25 | N | 13.2 uM | >25 | 12.8 uM |
| 5-(3-Amino-propyl)-4-benzothiazol-2-yl-2H-pyrazol-3-ylamine | 7.0 uM | 22.8 uM | 13.2 uM | 17.3 uM | 18.9 uM | 10.8 uM |
| 5-(4-Amino-phenyl)-4-benzothiazol-2-yl-2H-pyrazol-3-ylamine | 1.0 uM | 21.5 | 4.3 | 2.3 | 21.3 | 17.7 |
| 5-Methyl-4-(4,5,6-trifluoro-benzothiazol-2-yl)-1H-pyrazol-3-ylamine | 18.3 uM | >25 | | | | |
| 5-Methyl-4-(6-methylaminomethyl-benzothiazol-2-yl)-2H-pyrazol-3-ylamine | .5 uM | .9 uM | | | | |
| 5-Methyl-4-(6-morpholin-4-ylmethyl-benzothiazol-2-yl)-2H-pyrazol-3-ylamine | 3.8 uM | >25 | | | | |
| N-[2-(5-Amino-3-methyl-1H-pyrazol-4-yl)-benzothiazol-6-yl]-acetamide | 9.9 uM | >25 | 18.442 uM | 7.7 uM | 18.4 uM | 12.6 uM |

TABLE 2-continued

IC$_{50}$ of Compounds on Stimulated Macrophages and Splenocytes

| Chemical Name | IFNg on ConA 1° splenocytes (μM) | Survival of ConA 1° splenocytes | TNFa on macrophages (μM) | IL-12 on macrophages (μM) | Survival of macrophages | MCP1 on HUVECS (μM) |
|---|---|---|---|---|---|---|
| N$_3$-(2-Amino-ethyl)-4-benzothiazol-2-yl-1H-pyrazole-3,5-diamine | 16.6 uM | >25 | 23.9 Um | N | >25 | >25 |
| N3-(2-Dimethylamino-ethyl)-4-(5-fluoro-6-methoxy-benzothiazol-2-yl)-1H-pyrazole-3,5-diamine | 11.0 uM | >25 | 17.147 uM | >25 | >25 | >25 |
| N3-(3-Dimethylamino-propyl)-4-(5-fluoro-6-methoxy-benzothiazol-2-yl)-1H-pyrazole-3,5-diamine | 10.2 uM | ~25 | | | | |

7. Inhibition of Nitric Oxide

Peritoneal exudate macrophages were isolated by peritoneal lavage with ice-cold sterile physiological saline 24 hours after intraperitoneal injection of BALB/c mice with 0.3 ml of sterile zymosan A (1 mg/0.5 mL 0.9% saline). Cells were washed, resuspended in RPMI 1640 supplemented with 2 mM L-glutamine, 100 units/mL penicillin, 100 μg/mL streptomycin, and 5% FBS. 1.5×10$^5$ cells/well were seeded in 96-well plates and followed by 3 hour incubation at 37° C. with 5% CO$_2$ (macrophages were allowed to attach) cells were stimulated with LPS (0.5 mg/mL) and IFN-γ (100 U/mL) in the absence or presence of the test compounds. All treatments were replicated six times. Cells were incubated for an additional 24 hours, and cell free culture supernatants from each well were collected for NO and cytokine determination. The remaining cells were stained with crystal violet to determine effect of the compound on cell survival.

For discussion of the stimulation of primary mouse peritoneal macrophages for NO and cytokine determination see, e.g., Calandra T., Spiegel L. A., Metz C. N., and Bucala R. *Proc Natl Acad Sci USA* (1998) 95(19): 11383-8; Lu L., Bonham C. A., Chambers F. G., et al. *J Immunol.* (1996) 157(8): 3577-86; Keil D. E., Luebke R. W., and Pruett S. B. *Int J Immunopharmaco*" (1995) 17(3): 157-66; and Skeen M. J., Miller M. A., Shinnick T. M., et al. *J Immunol.* (1996) 156(3): 1196-206.

In testing of representative compounds, the release of IFNg from splenocytes was inhibited compared to controls. See Table 2, supra.

Inhibition of NO release determination:

The production of NO was determined by assaying culture supernatants for NO$_2^-$, a stable reaction product of NO with molecular oxygen. Briefly, 100 μL of culture supernatant was reacted with an equal volume of Griess reagent at room temperature for 10 minutes. The absorbance at 550 nm was determined. All measurements were performed six times. The concentration of NO$_2^-$ was calculated by comparison with a standard curve prepared using NaNO$_2$.

For discussion of measuring nitric oxide in tissue culture supernatants, see, e.g., Amano F., and Noda T. "Improved detection of nitric oxide radical (NO) production in an activated macrophage culture with a radical scavenger, carboxy PTIO and Griess reagent" *FEBS Lett.* (1995) 368(3): 425-8; Archer S. "Measurement of Nitric oxide in biological models" (1993) *FASEB J.* 7:349-360, and Amin A. R. "Regulation of nitric oxide and prostaglandin E2 production by CSAIDS (SB203580) in murine macrophages and bovine chondrocytes stimulated with LPS" *Inflamm Res.* (1999) 48(6):337-43.

TABLE 3

Percent Inhibition Of Nitric Oxide On Stimulated Macrophages At 25 μm for Representative Compounds

| Chemical Name | % Inhibition |
|---|---|
| 2-(5-Amino-3-methyl-1H-pyrazol-4-yl)-benzothiazole-6-sulfonic acid amide | 100 |
| 2-(5-Amino-4-benzothiazol-2-yl-2H-pyrazol-3-ylamino)-cyclopentanol | 78.6 |
| 4-(4-Benzothiazol-2-yl-1H-pyrazol-3-yl)-6-ethyl-benzene-1,3-diol | 99.3 |
| 4-(4-Benzothiazol-2-yl-1H-pyrazol-3-yl)-phenol | 69.6 |
| 4-(6-Bromo-benzothiazol-2-yl)-5-methyl-1H-pyrazol-3-ylamine | 100 |
| 4-(6-Fluoro-benzothiazol-2-yl)-5-methyl-1H-pyrazol-3-ylamine | 61.5 |
| 4-(6-Methanesulfonyl-benzothiazol-2-yl)-5-methyl-2H-pyrazol-3-ylamine | 52.9 |
| 4-(6-Methoxy-benzothiazol-2-yl)-5-methyl-1H-pyrazol-3-ylamine | 100 |
| 4-Benzothiazol-2-yl-1H-pyrazole-3,5-diamine | 53.6 |
| 4-Benzothiazol-2-yl-5-methyl-1H-pyrazol-3-ylamine | 96.4 |
| 4-Benzothiazol-2-yl-5-methylsulfanyl-1H-pyrazol-3-ylamine | 69.2 |
| 4-Benzothiazol-2-yl-5-phenyl-1H-pyrazol-3-ylamine | 76.7 |
| 4-Benzothiazol-2-yl-5-pyrrolidin-1-yl-1H-pyrazol-3-ylamine | 52.6 |
| 4-Benzothiazol-2-yl-N5-quinolin-6-yl-1H-pyrazole-3,5-diamine | 66.1 |

Example 43

In Vitro Angiogenesis Assay

Angiogenesis, the formation of new blood vessels from pre-existing endothelium, is a critical process involved in numerous physiological and pathological conditions. Disruption of this tightly regulated process has been implicated in both chronic inflammation and solid tumour growth. The Matrigel™ morphogenesis assay is an in vitro model used to mimic the process by which endothelial cells form capillaries in vivo. Human umbilical vein endothelial cells (HUVECs) were plated over matrigel, a complex mixture of solubilized basement membrane components, and cultured in serum poor medium with specific growth factors and in the presence of the test compound. HUVEC cells cultured for 24 hours in M199 with 0.5% FCS were plated at $6 \times 10^5$ cells/well in 12-well plates pre-coated with 300 μL of Matrigel (10.7 mg/mL) in M199 with 0.5% FCS in the presence of VEGF (1 ng/mL), and in the absence or presence of the test compounds. After 5 hours of incubation in a 5% $CO_2$-humidified atmosphere at 37° C., the three-dimensional organization of the cells (the capillary-like structures) was examined using an inverted photomicroscope. The cells were fixed with crystal violet (0.05% in 20% ethanol) and photographed using a digital camera. Qualitative analysis was accomplished by comparing the pattern, size and integrity of the vessels formed in the test wells with those of the VEGF control wells. Quantitative analysis was performed on the images collected using the Image-Pro Plus software program. See Table 4 for results with selected compounds.

For further discussion regarding in vitro angiogenesis assay, see, e.g., Grant D. S., Lelkes P. I., Fukuda K., and Kleinman H. K. "Intracellular mechanisms involved in basement membrane induced blood vessel differentiation in vitro" *In Vitro Cell Dev Biol*. (1991) 27A(4):327-36; Kubota Y., Kleinman H. K., Martin G. R., and Lawley T. J. "Role of laminin and basement membrane in the morphological differentiation of human endothelial cells into capillary-like structures" *J Cell Biol*. (1988) 107(4):1589-98; Passaniti A., Taylor R. M., Pili R., et al. "A simple, quantitative method for assessing angiogenesis and antiangiogenic agents using reconstituted basement membrane, heparin, and fibroblast growth factor" (1992) *Lab. Invest*. 67:519-528.

TABLE 4

Percent Inhibition of Angiogenesis

| Chemical Name | % Inhibition |
|---|---|
| 4-Benzothiazol-2-yl-1H-pyrazole-3,5-diamine | 32 |
| 4-Benzothiazol-2-yl-5-pyrrolidin-1-yl-1H-pyrazol-3-ylamine | 50 |
| 4-Benzothiazol-2-yl-5-methylsulfanyl-1H-pyrazol-3-ylamine | 84 |
| 4-Benzothiazol-2-yl-5-methyl-1H-pyrazol-3-ylamine | 64 |

Example 44

Tumor Cell Migration Assay

Tumor cell migration assay was conducted in the similar way as described in Example 16 except that the plates used were constructed with only a porous membrane dividing a top and bottom chamber without the additional thin Matrigel™ layer on top of the membrane (BD Fluoroblock™ plates). The percent inhibition of migration was determined in the same way as illustrated in Example 16.

See, e.g., Crouch M. F. (2000) "An automated fluorescence based assay of neurite formation" *J Neurosci Methods* 104 (1):87-91; and Repesh L. A. (1989) "A new in vitro assay for quantitating tumor cell invasion" *Invasion Metastasis* 9(3): 192-208 for additional discussion about invasion and migration assays.

Representative compounds were tested and the results are shown in Table 5.

TABLE 5

Percent Inhibition of Migration in PC3 Cells at 25 μM Compound

| Compound Name | % Inhibition |
|---|---|
| 4-(4-Benzothiazol-2-yl-1H-pyrazol-3-yl)-6-ethyl-benzene-1,3-diol | 80.0 |
| 4-(4-Benzothiazol-2-yl-1H-pyrazol-3-yl)-benzene-1,3-diol | 44.8 |
| 4-Benzothiazol-2-yl-1H-pyrazol-3-ylamine | 26.3 |
| 4-Benzothiazol-2-yl-1H-pyrazole-3,5-diamine | 27.9 |
| 4-Benzothiazol-2-yl-N5-ethyl-1H-pyrazole-3,5-diamine | 61.5 |
| 4-Benzothiazol-2-yl-5-pyrrolidin-1-yl-1H-pyrazol-3-ylamine | 47.4 |
| 4-Benzothiazol-2-yl-5-methylsulfanyl-1H-pyrazol-3-ylamine | 51.6 |
| 4-Benzothiazol-2-yl-5-methyl-1H-pyrazol-3-ylamine | 41.7 |
| 4-(4-Benzothiazol-2-yl-1H-pyrazol-3-yl)-phenol | 50.9 |
| 2-(4-Benzothiazol-2-yl-1H-pyrazol-3-yl)-phenol | 17.1 |
| 4-(5-Trifluoromethyl-benzothiazol-2-yl)-1H-pyrazol-3-ylamine | 56.1 |
| 4-Benzothiazol-2-yl-5-ethyl-1H-pyrazol-3-ylamine | 54.2 |
| 4-Benzothiazol-2-yl-N5-quinolin-6-yl-1H-pyrazole-3,5-diamine | 81.0 |
| 2-(5-Amino-4-benzothiazol-2-yl-2H-pyrazol-3-ylamino)-cyclopentanol | 23.1 |
| 4-(6-Methoxy-benzothiazol-2-yl)-5-methyl-1H-pyrazol-3-ylamine | 79.4 |
| 2-(5-Amino-3-methyl-1H-pyrazol-4-yl)-benzothiazole-6-sulfonic acid amide | 16.7 |
| 4-(6-Fluoro-benzothiazol-2-yl)-5-methyl-1H-pyrazol-3-ylamine | 45.3 |
| 2-(3-Amino-5-methyl-1H-pyrazol-4-yl)-benzothiazole-6-sulfonic acid methylamide | 30.5 |
| 2-(5-Amino-3-methyl-1H-pyrazol-4-yl)-5-fluoro-benzothiazole-6-sulfonic acid amide | 42.9 |
| -(5-Amino-3-methyl-1H-pyrazol-4-yl)-5-fluoro-benzothiazole-6-sulfonic acid (2-hydroxy-ethyl)-amide | 38.9 |

Example 45

Irritant Contact Dermatitis Model (ICD)

Female Balb/c ($H2-^d$) mice were used in this experiment (n=8). ICD was induced with phorbol 12-myristate 13-acetate (PMA), 4 μg/ear (in 20 μL acetone). Dexamethasone was used as a positive control (0.5 mg/kg) and was administered s.c. in 50 mL volume prior to irritation. The irritant was painted onto the dorsal side of the right ear pinna. The test compounds were delivered via oral gavage at a dose between 50-300 mg/kg (10 mL/kg). Ear thickness was measured with a spring-loaded dial micrometer before irritation and at 3, 6 and 24 hours after painting the irritant. The efficacy of the anti-inflammatory effect of the test compounds was determined by comparison of the thickness of the inflamed ear and the control ear.

Example 46

Orthotopic Lung Model

NCI-H460 human lung large cell carcinoma cells were harvested by trypsinization and adjusted to a final concentration of $1 \times 10^6$ cells/80 mL. Male nude rats (CR:NIH-RNU) were endobronchially implanted with $1 \times 10^6$ tumor cells using a 20 gauge, 2 inch Teflon™ catheter passed into the right caudal lobe via a small tracheotomy incision.

Implantation of tumor fragments. These tumor-bearing rats were sacrificed at three weeks following implantation and their tumors harvested in cold RPMI 1640. Viable tumor was cut into 1-2 mm diameter pieces by "crossed scalpels" technique. A 50 mg portion was placed into a 16 gauge, 2 inch Teflon™ catheter and implanted into 6-week-old male nude rats using a similar technique. Animals were treated with Augmentin™ supplement at 0.35 mg/mL in water for 2 weeks.

The test compound was prepared fresh each day by dissolving it in an acceptable recipient at 10 mg/mL under sterile conditions. Cisplatin injection, 1 mg/mL, was obtained from the hospital pharmacy.

There were four arms in the study: control; test compound alone; cisplatin alone; test compound and cisplatin combination. Also, there were two groups in the study: in group I, all animals were followed until death to assess maximum length of survival and in group II, all animals were simultaneously sacrificed from each treatment arm as control animals became severely cachectic or died. This allows us to directly compare, at the same point in time, the therapeutic effects of each study arm on tumor related endpoints, such as primary tumor weight, tumor/body weight ratio, mediastinal lymph node weight and metastatic pattern. Renal and liver functions of each animal were also examined by serum biochemistry to assess possible toxicities.

Both test compound (5 mg daily) and cisplatin (5 mg/kg weekly for 3 weeks) were administered by intraperitoneal injection. Treatment commenced 7 days and 14 days post implantation for the test compound and cisplatin, respectively. Animals were sacrificed when they showed signs of significant morbidity or impending death. At necropsy the heart-lung blocks, kidney, brain, and chest wall were removed, serially sectioned, stained, and examined in a blinded fashion by a pathologist.

Statistical analysis for length of survival, primary tumor, body, and mediastinal lymph node weight were evaluated using ANOVA or unpaired Student's t-test. Incidence of metastasis was evaluated by using a contingency table with Fisher's exact test. Differences of $P<0.05$ were considered to be significant.

Immunocytochemistry. The H-460 cell line was seeded into 8-chamber slides ($10^4$ cells/well) and treated with 25 μM of the test compound after reaching a confluency of 60 to 80%. Cells were harvested at 2, 4, 8 and 24 hours after treatment and incubated overnight at 4° C. with the primary antibodies. For phosphorylated Akt/PKB expression anti-phospho-Akt/PKB (Ser-473), was used at a concentration of 2 μg/mL, followed by incubation with the secondary antibody, biotinylated rabbit-IgG at a concentration of 7 μg/mL. For phosphorylated GSK-3β expression anti-phospho-GSK-3β (Ser-9), a concentration of 6 μg/mL was used, followed by incubation with the same secondary antibody. Streptavidin-peroxidase was used as a detection system. DAB was used as chromogen and counterstaining was performed with hematoxylin. Slides were assessed as either positive or negative according to the amount and intensity of staining. Phospho-Akt/PKB and phospho-GSK-3β reactivity was quantitated by computerized image analysis using an Image-Pro™ system and conventional light microscopy.

Example 47

ILK Expression is High in Human Psoriatic Skin as Compared to Normal Skin

The thickness of the epidermal layer within psoriatic plaques is dramatically greater than that of normal skin of healthy individuals or the uninvolved skin of the psoriasis patient.

To test for ILK expression, skin samples were obtained from a human subject with healthy skin and from patients suffering from the immune-mediated condition psoriasis. Skin preparations were processed using routine formalin-fixation and paraffin embedding techniques. Sections were cut and treated with antigen retrieval methodology and stained with a rabbit anti-ILK polyclonal antibody (catalogue #06-592, Upstate Biotechnology, Lake Placid N.Y.). Sections were then incubated with peroxidase-conjugated goat anti-rabbit polyclonal antibody. Slides were then developed using standard techniques.

In normal skin, a low level of ILK expression was evident in the supra-basal layers of skin keratinocytes. These supra-basal layers of skin keratinocytes were almost certainly undergoing the process of terminal differentiation. The staining intensity for ILK was more intense for keratinocytes near the outer keratin layer. Little or no ILK staining was observed for the dermal vascular endothelium. In contrast, staining for ILK was highly intense for the hyper-proliferative keratinocytes within the plaques of patients with psoriasis patients. Within the dermal region of psoriatic patient plaques, cells comprising the vasculature stained strongly for ILK. Further, some of the inflammatory cells present within the dermal region stained positively for ILK. Overall, in contrast to normal skin, ILK was expressed at much higher levels within the epidermal and dermal regions within skin plaques of patients with psoriasis.

Example 48

Expression of ILK in Psoriatic Tissue Correlates with Severity of Disease

The expression of ILK within psoriatic skin was evaluated for a series of plaque biopsy samples obtained from a patient over a 3-month period. The presence and expression pattern of ILK was evaluated by immunohistological analyses. All sections were stained at the same time. For psoriasis, the disease-state can be gauged by the relative thickness of the epidermis. For the series of biopsy samples evaluated, expression levels of ILK closely paralleled the psoriasis disease-state at the tissue level.

The first sample (panel A), was obtained at screening while the patient was experiencing active disease. Staining for ILK was intense for the keratinocytes within the target plaque. Within the dermal region of the plaque, cells within the vasculature as well as cells that had infiltrated the region also stained strongly for ILK. The second sample (panel B) was obtained one month later, a time when disease activity had further intensified. ILK staining intensity with this sample was much stronger than for the first sample. The third sample was taken approximately 4 weeks after sample B, a time during which this subject was exhibiting an improvement in his disease and a reduction in epidermal thickness. For this sample (panel C) there was a correspondent reduction in ILK staining intensity, both for the epidermal keratinocytes and within cells of the dermal vasculature. Sample 4 was obtained 3 months after sample 1, at a time when the subject was experiencing a flare in disease activity. Epidermal thickness for sample 4 was greater than that of sample 3. At this time, an increase in ILK staining intensity was evident within the dermal vasculature and cellular infiltrate as well as for the epidermal keratinocytes (panel D). Thus, expression levels of ILK within the psoriatic plaque varied with disease activity with high ILK expression correlating with symptoms of active disease.

Example 49

Anti-ILK Compound Inhibits Influx of Neutrophils into Site of Inflammation

Administration of certain pro-inflammatory agents, such as zymosan, into the peritoneal cavity of mice elicits a rapid influx of neutrophils into this region. The migration of these cells into the peritoneal cavity requires the coordinate interaction of cytokines, chemokines and cell adhesion molecules. Such a system can be used to evaluate the action of compounds with potential for modifying the migration of cells in response to pro-inflammatory stimuli.

When zymosan was administered to mice, peritoneal cavity neutrophil numbers increased by approximately 4-fold within 4 hours. However, if a compound of the invention was given orally at 200 mg/kg at the time of zymosan administration, cells numbers within the peritoneal cavity were equivalent to those of animals that received a saline control solvent 4 hours before. Thus, a compound with specific in vitro anti-ILK activity can affect the influx of cells into a tissue following the delivery of a strong pro-inflammatory signal in vivo.

For a discussion of acute inflammation models, including Irritant contact dermatitis (ICD) and allergic contact dermatitis (ACD), see, e.g., Artik S., von Vultee C., Gleichmann E., Schwarz T., and Griem P. "Nickel allergy in mice: enhanced sensitization capacity of nickel at higher oxidation states" *J. Immunol.* (1999) 163(3):1143-52; Becker D., Lempertz U., Enk A., Saloga J., and Knop J. "Contact sensitizers modulate mechanisms of receptor-mediated endocytosis but not fluid-phase endocytosis in murine epidermal Langerhans cells" *Exp. Dermatol.* (1995) 4(4 Pt 1):211-7; Griswold D. E., Martin L. D., Badger A. M., Breton J., and Chabot-Fletcher M. "Evaluation of the cutaneous anti-inflammatory activity of azaspiranes" *Inflamm. Res.* (1998) 47(2):56-61; and Moreno J. J. "Effect of retinoids on dermal inflammation and on arachidonic acid mobilization and metabolism in murine 3T6 fibroblasts retinoids, arachidonate release and metabolism" *Int. J Immunopharmacol.* (1996) 18(8-9):459-65.

Example 50

Demonstration of ILK Inhibition as Therapeutic Intervention in Renal Disorders In Vitro Murine Podocyte Model 1. Survival Assay in Podocytes The treatment of glomerular visceral epithelial cells (podocytes) with high concentrations of puromycin aminonucleoside (PAN) causes significant cytotoxic effects. An assessment of cell viability subsequent to a cytotoxic exposure can be judged qualitatively by examining changes in cell phenotype after staining with crystal violet or determined quantitatively by employing a cytotoxic assay using the soluble tetrazolium salt [3-(4,5-dimethylthiazol-2-yl)-5-(3-carboxymethoxyphenyl)-2-(4-sulfophenyl)-2H-tetrazolium, inner salt] (MTS). Such a system can be used to evaluate the survival effects that ILK compounds have on podocytes following exposure to PAN or other cytotoxic agents.

The cell line employed for the podocyte model was the murine K5P5. Cells were maintained and grown in tissue culture flasks (T75) in RPMI 1640+10% FBS medium supplemented with 10 U/ml of IFNγ and incubated at 33° C., 5% $CO_2$. The cells should be propagate to a maximum of 20 passages.

Cells were trypsinized (0.25%), collected from the tissue culture flasks centrifuged, resuspended and counted.

Collagen coated flasks were prepared by adding 1 ml/25 $cm^2$ of a 100 µg/ml Collagen I (Biochrom) and allowing to bind for 1 hour at 37° C. The flasks were then washed twice with PBS to remove any unbound Collagen I.

Podocyte cellular differentiation was initiated by seeding the cells ($1 \times 10^6$) on Collagen I coated flasks (T150) in RPMI 1640+10% FBS medium without IFNγ. The flasks were incubated at 37° C., 5% $CO_2$ for 3 days.

Cells were trypsinized (0.25%), collected from the tissue culture flasks centrifuged, resuspended and counted.

Podocyte cellular differentiation was continued by seeding the cells ($7 \times 10^5$) on Collagen I coated flasks (T150) in RPMI 1640+10% FBS medium without IFNγ. The flasks were incubated at 37° C., 5% $CO_2$ for 4 days.

Collagen coated 96-well plates were prepared by adding 75 µl/well of a 100 µg/ml Collagen I (Biochrom) and allowing to bind for 1 hour at 37° C. The flasks were then washed twice with PBS to remove any unbound Collagen I.

Cells were trypsinized (0.25%), collected from the tissue culture flasks centrifuged, resuspended and counted. Podocyte cellular differentiation was continued by seeding the cells ($3.5 \times 10^3$) on Collagen I coated 96-well plates in 10% FBS RPMI 1640 medium without IFNγ. The flasks were incubated at 37° C., 5% $CO_2$ for 3 days.

On day 10, the supernatant was removed from the 96-well plates and replaced with 2% FBS RPMI 1640 overnight.

For test compounds, cell culture media (e.g., RPMI 1640+ 2% FBS), 10× compound solution of final desired concentration from 40 mM stock compounds was prepared.

10 µl of this 10× compound solution is added to the 80 µl of cells already present in the 96-well plates. For cell undergoing cytotoxic treatment, puromycin aminonuceloside (PAN, Sigma P7130) was added at a 10× concentration to 90 µl of cells. The positive control is PAN treatment without compound. The negative control is 100% DMSO diluted to the same factor as the compounds without PAN.

The plates are incubated at 37° C., 5% $CO_2$ for 48 to 72 hours depending on the PAN concentration (i.e. lower concentrations of PAN required a longer incubation period). The medium is aspirated after plates are spun at 2400 rpm for 10 min at ambient temperature. 100 µl of 1×DPBS (without $CaCl_2$, without $MgCl_2$) is added to each well.

The MTS (Promega) is prepared under low lighting conditions by dissolving 4.0 g of MTS in 1.8 l of 1×DPBS. The solution is allowed to sit for 10 minutes and pH adjusted to 6.2. $H_2O$ is added to 2 L. 100 ml of PMS is added (dissolve 0.92 g of PMS in 1.0 l of 1×DPBS) and 20 µl of MTS is added slowly to each well and incubated for 4 hours at 37° C. Absorbance is measured at 490 nm wavelength with a microplate reader.

A kit available to do this assay is "CellTiter 96® AQ$_{ueous}$ Kit (G5421)" by Promega.

The values for four replicates are averaged and % inhibition is calculated at follows:

% survival=100−[(AVG treatment−AVG positive control)/(AVG negative control−AVG positive control)*100].

The cyto-protective activity of 5 representative compounds is shown Table 6. Several of the $IC_{50}$ measurements were in the range of 2.5 to 12.5 µM with two of the compounds reaching 80% survival of K5P5 podocytes in the presence of PAN (data not shown). To further evaluate the compound effects that were observed with the MTS assay, cells were analyzed for changes in morphology. The cells were photographed after being stained with crystal violet. The results demonstrated that the increase in cell survival observed by the MTS assay correlates with the restoration of the normal phenotype of the podocytes. Hence, increased doses of compound resulted in an increase in cell size, cell spreading (adhesion) and overall cell number (data not shown).

TABLE 6

% Survival on PAN a treated K5P5 podocyte cell line ($IC_{50}$, µM)

| Chemical Name | % Survival |
|---|---|
| 2-(3-Amino-5-methyl-1H-pyrazol-4-yl)-benzothiazole-6-sulfonic acid methylamide | 12.5 |
| 2-(5-Amino-3-methyl-1H-pyrazol-4-yl)-5-fluoro-benzothiazole-6-sulfonic acid amide | 30% @ 12.5 |
| 2-(5-Amino-3-methyl-1H-pyrazol-4-yl)-5-fluoro-benzothiazole-6-sulfonic acid (2-hydroxy-ethyl)-amide | 30% @ 25 |
| 4-(5-Fluoro-6-methoxy-benzothiazol-2-yl)-5-furan-2-yl-2H-pyrazol-3-ylamine | 2.5 |
| 4-(6-Dimethylaminomethyl-benzothiazol-2-yl)-5-methyl-2H-pyrazol-3-ylamine | 12.5 |

2. Transgenic Mouse Model

Mice transgenic for the bovine growth hormone (GH) under a methallothionein I promoter are used (Wanke, R., et al. *Pediatric Nephrol* (1991) 5:513-521). Genotype can be confirmed by genomic PCR with bovine GH specific primers (Wanke, R., et al supra). Glomeruli can be isolated after pooling kidneys from two or more animals. For the animal model, accelerated nephrotoxic serum nephritis (NTX) is induced in 4 to 6 week old females as previously reported (Schadde, E., et al. *Nephrol Dial Transplant* (2000) 15:1046-1053; Neugarten, J., et al. *J Am Soc Nephrol* (1995) 5:1903-1909). Five days after preimmunization with rabbit IgG, 400 µg of a protein A purified IgG fraction of a nephrotoxic rabbit anti-murine GBM antiserum is intravenously injected, while controls receive carrier only. Mice in each group are sacrificed after 0, 2, and 7 days and a pooled glomerular fraction is obtained from each group for expression analysis. Albuminuria is determined using a commercially available mouse albumin specific ELISA system (Exocell, Philadelphia, PE).

3. Measuring Levels of ILK from Podocytes

To assess the efficacy of a candidate pyrzolylbenzothiazole compound in vivo, the following podocyte extraction method may be used. Single cell RT-PCR is performed as described in Schroppel, B., et al. *Kidney Int* (1998) 53:119-124. Freshly dissected glomeruli from CD-1 mice are transferred to a patch clamp apparatus. Single podocytes are selectively harvested by aspiration of the cells into a micropipette. Reverse transcribed and RT-PCR is performed essentially as described above, but using 50 instead of 30 cycles. Perfusion medium aspirated next to a glomerulus is processed in parallel and serves as negative control. Single cell ILK RT-PCR product identity is verified by restriction digest. Single podocyte RNA is quantified using published real-time RT-PCR technology (Heid, C. A., et al. *Genome Res* (1996) 6:986-994). For determination of ILK copy number per single podocyte cDNA, a standard curve of serial dilutions of ILK plasmid cDNA with known copy numbers is employed. ILK copies per podocyte cDNA are calculated using the Ct value minus the dilution factor and the standard curve ($y=-1.6227 \ln(x)+39$ with $R2=0.9935$) generated from duplicate amplification reactions of log fold dilutions between 100,000 and 10 ILK plasmid copies.

4. Adriamycin-Induced Proteinuria Model

This model, which results in focal glomerular sclerosis (FGS), is well described in Wang, Y., et al. *Kidney Int* (2000) 58:1797-1804. Groups of BALB/c mice are injected intravenously on day 0 with a single dose of Adriamycin (ADR, doxorubicin hydrochloride, Pharmacia & Upjohn) at 10-11 mg/kg, or vehicle control. Six to eight animals in each group are analyzed.

| GROUP | TREATMENT |
|---|---|
| Negative control group | Intravenous carrier on day 0, vehicle daily from day 0 |
| Positive control group | Intravenous ADR on day 0, vehicle daily from day 0 |
| Test group | Intravenous ADR on day 0, various doses of ILK inhibitor from day 0 |

Pyrazolylbenzothiazole compounds are administered orally, intraperitoneally or by subcutaneous infusion pump, in daily doses ranging from 0.01-200 mg/kg, beginning on day 0. Vehicle (carrier) controls are administered in equivalent volumes by the same routes.

Experimental readouts include weekly body weight, urine volume, urinary protein, serum creatinine and albumin, and terminal histopathology. Negative control mice demonstrate no significant changes in experimental readouts. The positive control group demonstrates significant changes associated with rapid progressive renal disease (FGS) using experimental readouts, namely proteinuria, hypoalbuminemia, hypercreatininemia, and progressive renal injury by histology. In the experimental groups treated with various doses of pyrazolylbenzothiazole compound, decreases in measured parameters of progressive renal disease are demonstrated compared to the positive control group, indicating that administration of pyrazolylbenzothiazole compounds results in therapeutic benefit in this model of acute progressive focal glomerular sclerosis.

5. Murine Unilateral Ureteral Obstruction Model

This model results in epithelial-mesenchymal transdifferentiation in renal fibrosis and is described in Vielhauer V., et al. *J Am Sox Nephrol* (2001) 12: 1173-1187. Briefly, female inbred C57BL/6 mice weighing ca. 20-26 g are obtained and kept under a ca. 12-h light/dark cycle. Food and water are available ad libitum. Under general anesthesia, unilateral ureteral ligation resulting in UUO is performed by ligating the left distal ureter with a 2/0 Mersilene™ suture through a low midline abdominal incision. Unobstructed contralateral kidneys serve as controls.

Experimental Plan for UUO Model

| GROUP (8-10 mice) | PRE-TREATMENT | TREATMENT |
|---|---|---|
| Negative control group | Sham operated mice | Receive carrier only for 10 days |
| Positive control group | Mice with one obstructed kidney | Receive carrier only for 10 days |
| Test group | Mice with one obstructed kidney | Receive various doses of ILK inhibitor for 10 days |

Test compounds are administered orally, intraperitoneally or by subcutaneous infusion pump, in daily doses ranging from 0.01-200 mg/kg. Vehicle (carrier) controls are administered in equivalent volumes by the same routes. Experimental readouts included histological fibrosis scores, serum urea, collagen levels and ILK mRNA expression. Analysis of ILK mRNA levels are also performed in infiltrating cells (macrophages and T-cells) after cell sorting in renal fibrosis in the UUO model. Negative control (sham operated) mice demonstrate no significant changes in experimental readouts. The UUO control group demonstrates significant changes associated with renal fibrosis in the ligated kidney using experimental readouts. Also observed in these animals is an increase in ILK mRNA induction. In the experimental groups treated with various doses of pyrazolylbenzothiazole compound, the non-ligated kidneys are used as internal controls, and the non-ligated kidneys demonstrate no significant changes associated with renal tubulo-interstitial fibrosis using experimental readouts, however the damaged kidneys demonstrate decreases in measured parameters of renal fibrosis compared to the UUO control group. This result indicates that administration of pyrazolylbenzothiazole compounds results in therapeutic benefit in this model of renal tubulo-interstitial fibrosis.

Example 51

Treatment of AMD Using an ILK Inhibitor as an Adjunct to Visudyne™ Therapy

Therapeutic effect of a pyrazolylbenzothiazole compound in AMD is evaluated using visual acuity as the primary clinical outcome. Patients with subforveal CNV lesions caused by AMD are examined for the presence of lesions that meet the inclusion criteria. The inclusion criteria are defined as the presence of lesions measuring 5400 μm or less in greatest linear dimension with evidence of classic CNV and best-corrected visual acuity of approximately 20/40 to 20/200 based on fluorescein angiographic and visual acuity examination. Those determined as qualified for the treatment of AMD are randomly assigned to 4 groups. Group A, B, and C are treated with standard Visudyne™ therapy with an adjunct therapy using an ILK inhibitor. Patients of Group D are treated with standard Visudyne™ therapy in combination with a placebo of the ILK inhibitor.

For standard Visudyne™ therapy, patients are administered with 30 ml of Visudyne™ (0.15 mg per kilogram of body weight). The administration is by intravenous infusion over a period of 10 minutes. Fifteen minutes after the end of the infusion, the laser light is applied for 83 seconds to the CNV lesion through a fundus contact lens of known magnification to result in a light exposure of 50 J/cm². A circular spot of approximately 6000 microns encompassing the area of the lesion is exposed to the laser light.

For the adjunct therapy, patients of groups A, B, and C receive a daily oral administration of an ILK inhibitor at the dose of 5, 10, 20 mg per kilogram body weight, respectively. The adjunct treatment commences three days after the patient receiving the standard Visudyne™ therapy and continues for a period of one month.

As follow-up, patients are examined every three months. At each regularly scheduled follow-up visit, best-corrected visual acuity measurement, contrast threshold measurement, ophthalmoscopic examination, stereoscopic fundus photography, and fluorescein angiography are performed.

Example 52

Treatment of Diabetic Retinopathy Using an ILK Inhibitor

Therapeutic effect of a pyrazolylbenzothiazole compound in proliferative diabetic retinopathy is evaluated using visual acuity as the primary clinical outcome. Patients with proliferative diabetic retinopathy and visual acuity of 20/100 or better in each eye are included in the clinical evaluation. Patients are randomly assigned to 3 treatment groups and 1 placebo group. Group A, B, and C are treated with daily oral administration of a pyrazolylbenzothiazole compound at the dose of 5, 10, 20 mg per kilogram body weight. Patients of Group D receive placebo. The treatment covers a period of 24 months.

As follow-up, patents are examined every 4 months. At each regularly scheduled follow-up visit, best-corrected visual acuity measurement, contrast threshold measurement, indirect ophthalmoscopic examination, stereoscopic fundus photography, fluorescein angiography, and slit-lamp examination using 78- or 90-diopter lens are performed.

Example 53

Evaluation of ILK Expression in Ocular Vascular Tissue

This example indicates the relevance of ILK as a therapeutic target for diseases with underling pathology of ocular neovascularization.

Post mortem baboon eye samples were subjected to immunohistological analysis for the expression of ILK in ocular vasculature. Freshly obtained tissues were snap-frozen by immersing into a Dewar container of liquid nitrogen. Cross sections of 5-10 microns were prepared and fixed in cold acetone (−20 C). Immunohistology was performed using a rabbit anti-ILK antibody (Upstate Biotechnology Institute, NY. Cat. #06-550) and Zymed Histostatin™ Plus kit (Zymed, Cat. #85-9743).

Abundant expression of ILK was detected in choroidal and retinal endothelium in post mortem baboon eye samples. Under similar condition, no significant level of ILK expression was detected in retinal pigmented epithelial cells. In addition, no significant expression of ILK in neurons and photoreceptors was observed.

Example 54

Treatment of Corneal Neovascularization with an ILK Inhibitor

The following model provides a quantifiable in vivo assay that can be used to evaluate anti-angiogenic activity of an pyrazolylbenzothiazole compound. Corneal neovascularization is induced by a procedure known as silver nitrate cauterization. The procedure involves topical applications of silver nitrate onto the cornea by gently touching conjunctiva/limbus for one second followed by touching the central cornea of an anesthetized mouse for 8 seconds with a silver nitrate applicator (Graham-Field, N.Y., Item #1590, 75% silver nitrate, 25% potassium nitrate). Immediately after, the eye is rinsed with 10 ml of saline followed by topical application of Gentak™ Ophthalmic Ointment (0.3%, Gentamicin sulfate) on the eye to prevent bacterial infections.

Corneal neovascularization is recorded and evaluated by examining and photographing the cornea daily using a stereo dissecting microscope connected to a color video camera and a computer. Angiogenesis is evaluated based on new blood vessel growth within previous avascular cornea using a scoring system (score of 0-4) that rates from no neovascularization to very severe neovascularization in cornea. In addition, upon completion of the experiment (day 5-7), corneal neovascularization is quantified using computer-assisted image analysis (Image Pro Plus, Media Cybernetics, ML) of dye-stained blood vessels in post mortem whole corneal mounts. Corneal vasculature is stained by IV injection of high molecular weight FITC-dextran into anesthetized mice before euthanasia.

Animals receive daily intra-peritoneal administration of a pyrazolylbenzothiazole compound at the dose of 5, 25 or 50 mg/kg commencing on day-2 after the silver nitrate cauterization procedure until 24 h before the ending of the experiment. Corneal neovascularization of ILK inhibitor-treated animals is compared with that of vehicle-treated animals.

Example 55

Treatment of Choroidal Neovascularization with an ILK Inhibitor Using a Monkey Model of CNV The following model provides an in vivo assay that can be used to evaluate therapeutic potential of pyrazolylbenzothiazole compounds for the treatment of CNV. CNV is induced by argon green laser burns that are placed in the maculae of cynomolgus monkeys using a modification of Ryan's model. The laser burn with size of 50 µm in diameter is induced by exposure to 350-450 mW laser light at 514 nm for 0.1 second using an argon laser (Coherent Argon Dye Laser #920, Coherent Medical Laser, Polo Alto, Calif.).

CNV is monitored by weekly examination with fundus photography and fluorescein angiography. At the termination of the experiment (2-3 months after the induction of CNV), eyes are enucleated under deep anesthesia and fixed in modified Kanovsky fixative. Bisection is performed 20 min after fixation. Tissues are then embedded and sections are generated for histological and immunohistological analysis using antibodies against vasculature-specific markers including CD-31 and VE-Cadherin. The extent of neovascularization is quantified using a computer-assisted image analysis system with Image Pro Plus (Media Cybernetics, ML).

Animals receive daily oral administration of a pyrazolylbenzothiazole compound at the dose of 10, 50 or 100 mg/kg for commencing after the onset of CNV (2-3 weeks after the laser treatment). As control, a group of monkeys receive daily oral treatment with vehicle only. CNV in ILK inhibitor-treated animals is compared with that of vehicle-treated animals for angiographic and immunohistological evidence of CNV.

Example 56

Treatment of Retinal Neovascularization with an ILK Inhibitor Using a Mouse Model of Ischemia-Induced Retinopathy The following model provides an in vivo assay that can be used to evaluate therapeutic potential of pyrazolylbenzothiazole compounds for the treatment of retinopathy. This is a mouse model of retinopathy of prematurity. Retinopathy in mice is induced in neonatal mice. Mice are exposed with their nursing dams to 75% oxygen/25% nitrogen from postnatal day 7 to day 12, then put back to room air.

At day 17, all pups are weighed, euthanised, and perfused with 1 ml fixative (4% paraformaldhyde/8% sucrose/sodium phosphate buffer, pH 7.2) through the left ventricle of heart. Eyes are enucleated and placed in fixative. The fixed tissues are paraffin-embedded and 4-µm sections are cut. Immunohistology procedure is performed to evaluate extent of retinal neovascularization using antibodies against endothelium-specific markers including CD-31 and VE-cadherin. The vascular specific staining is quantified using the computer-assisted image analysis method (Image Pro Plus, Media Cybernetics, ML).

The pyrazolylbenzothiazole compound at the dose of 5, 25 or 50 mg/kg is administered daily through intra-peritoneal injection from day 12 through day 16. The control group receives daily injection of vehicle. The inhibitory effect of the ILK inhibitor on retinal neovascularization is determined by comparing the extent of vascular staining in mice treated with the compound and those treated with vehicle only.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A pharmaceutical composition comprising a pharmaceutically acceptable excipient and a compound of formula (3):

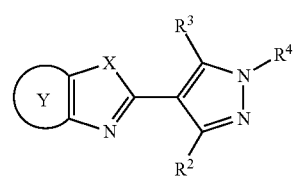

as a single tautomer, a mixture of tautomers, a single stereoisomer, a mixture of stereoisomers, or a racemic mixture; or a pharmaceutically acceptable salt thereof; wherein:

R² at each occurrence is independently selected from aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfoxido, thiol, thioureido, and ureido;

R³ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfoxido, thiol, thioureido, and ureido;

R⁴ is selected from hydrogen, heteroalkyl, heteroaryl, and hydrocarbyl;

X is S; and

Y is a 6 membered heterocycle having 1 or 2 nitrogen atoms and which is optionally further substituted by one or more groups selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfoxido, thiol, thioureido, and ureido.

2. A composition according to claim 1 wherein heteroalkyl is selected from aminohydrocarboyl (i.e., —NH—C(═O)-Hy), amido (i.e., —C(═O)—NH₂), carboxylic acid (i.e., —COOH), cyano (i.e., —CN), dihydrocarbylamido (i.e., —C(═O)—N(Hy)(Hy)), dihydrocarbylamino (i.e., —N(Hy)(Hy)), di(hydrocarbyl)phosphido, formyl (i.e., —C(═O)H), hydrocarboyl (i.e., —C(═O)-Hy), hydrocarboyloxy (i.e., —O—C(═O)-Hy) hydrocarbylamino (i.e., —NH-Hy), hydrocarbyloxy (i.e., —O-Hy), hydrocarbyloxycarbonyl (i.e., —C(═O)—O-Hy) hydrocarbylsiloxy, hydrocarbylsilylamino, hydrocarbylsulfido (i.e., —S-Hy), hydrocarbylthio, hydrocarbylamido (i.e., —C(═O)—N(H)(Hy)), isothiocyanate, N-heterocycle, perfluorohydrcarbyl, thiocyanate, and hydrocarbyl substituted with one or more groups selected from alkylamino, amino, aminosulfinyl, aminosulfonyl, azido, dialkylamino, halogen, heteroalkyl, heteroaryl, hydrazinyl, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfoxido, thiol, thioureido, and ureido.

3. The composition of claim 1 where hydrocarbyl is selected from the group consisting of alkyl, alkenyl, alkynyl, cycloalkyl, cycloalkylene, and aryl, wherein:

alkyl, alkenyl and alkynyl is optionally substituted with one or more Hy¹ groups selected from cycloalkyl, cycloalkylene and aryl, where each Hy¹ group is optionally substituted with one or more Hy² groups selected from alkyl, alkenyl, alkynyl, cycloalkyl, cycloalkylene, and aryl; and cycloalkyl, cycloalkylene and aryl is optionally substituted with one or more Hy² groups;

provided that when Hy² is selected from alkyl, alkenyl or alkynyl, then Hy² may be substituted with one or more Hy³ groups selected from cycloalkyl, cycloalkylene and aryl, where each Hy³ group is optionally substituted with one or more Hy⁴ groups selected from alkyl, alkenyl, alkynyl, cycloalkyl, cycloalkylene, and aryl, and when Hy² is selected from cycloalkyl, cycloalkylene and aryl then Hy² is optionally substituted with one or more Hy⁴ groups; and further provided that aryl includes an aryl ring fused to a non-aromatic hydrocarbocyclic ring.

4. The composition of claim 1 wherein R⁴ is hydrogen.

5. The composition of claim 1 wherein R² is selected from lower alkyl and lower haloalkyl.

6. The composition of claim 1 wherein R³ is amino.

7. The composition of claim 1 wherein the compound of formula (3) is 5-methyl-4-thiazolo[5,4-b]pyridin-2-yl-1H-pyrazazol-3-ylamine.

8. A compound of formula (3):

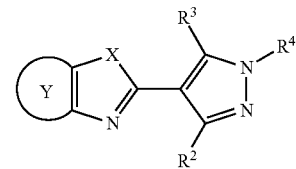

(3)

as a single tautomer, a mixture of tautomers, a single stereoisomer, a mixture of stereoisomers, or a racemic mixture; or a pharmaceutically acceptable salt thereof; wherein:

R² at each occurrence is independently selected from aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfoxido, thiol, thioureido, and ureido;

R³ at each occurrence is independently selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfoxido, thiol, thioureido, and ureido;

R⁴ is selected from hydrogen, heteroalkyl, heteroaryl, and hydrocarbyl;

X is S; and

Y is a 6 membered heterocycle having 1 or 2 nitrogen atoms and which is optionally further substituted by one or more groups selected from amino, aminosulfinyl, aminosulfonyl, aryl, azido, halogen, heteroalkyl, heteroaryl, hydrazinyl, hydrocarbyl, hydrogen, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfoxido, thiol, thioureido, and ureido.

9. The compound of claim 8 wherein heteroalkyl is selected from aminohydrocarboyl (i.e., —NH—C(═O)-Hy), amido (i.e., —C(═O)—NH₂), carboxylic acid (i.e., —COOH), cyano (i.e., —CN), dihydrocarbylamido (i.e., —C(═O)—N(Hy)(Hy)), dihydrocarbylamino (i.e., —N(Hy)(Hy)), di(hydrocarbyl)phosphido, formyl (i.e., —C(═O)H), hydrocarboyl (i.e., —C(═O)-Hy), hydrocarboyloxy (i.e., —O—C(═O)-Hy) hydrocarbylamino (i.e., —NH-Hy), hydrocarbyloxy (i.e., —O-Hy), hydrocarbyloxycarbonyl (i.e., —C(═O)—O-Hy) hydrocarbylsiloxy, hydrocarbylsilylamino, hydrocarbylsulfido (i.e., —S-Hy), hydrocarbylthio, hydrocarbylamido (i.e., —C(═O)—N(H)(Hy)), isothiocyanate, N-heterocycle, perfluorohydrcarbyl, thiocyanate, and hydrocarbyl substituted with one or more groups selected from alkylamino, amino, aminosulfinyl, aminosulfonyl, azido, dialkylamino, halogen, heteroalkyl, heteroaryl, hydrazinyl, hydroxyl, nitro, nitroso, phosphate, phosphinate, phosphonate, phosphonium, phosphorothioate, phosphoryl, sulfamoyl, sulfate, sulfinic acid, sulfonamido, sulfonate, sulfonic acid, sulfoxido, thiol, thioureido, and ureido.

10. The compound of claim 8 where hydrocarbyl is selected from the group consisting of alkyl, alkenyl, alkynyl, cycloalkyl, cycloalkylene, and aryl, wherein:
   alkyl, alkenyl and alkynyl is optionally substituted with one or more $Hy^1$ groups selected from cycloalkyl, cycloalkylene and aryl, where each $Hy^1$ group is optionally substituted with one or more $Hy^2$ groups selected from alkyl, alkenyl, alkynyl, cycloalkyl, cycloalkylene, and aryl; and
   cycloalkyl, cycloalkylene and aryl is optionally substituted with one or more $Hy^2$ groups;
   provided that when $Hy^2$ is selected from alkyl, alkenyl or alkynyl, then $Hy^2$ may be substituted with one or more $Hy^3$ groups selected from cycloalkyl, cycloalkylene and aryl, where each $Hy^3$ group is optionally substituted with one or more $Hy^4$ groups selected from alkyl, alkenyl, alkynyl, cycloalkyl, cycloalkylene, and aryl, and when $Hy^2$ is selected from cycloalkyl, cycloalkylene and aryl then $Hy^2$ is optionally substituted with one or more $Hy^4$ groups; and
   further provided that aryl includes an aryl ring fused to a non-aromatic hydrocarbocyclic ring.

11. The compound of claim 8 wherein $R^4$ is hydrogen.

12. The compound of claim 8 wherein $R^2$ is selected from lower alkyl and lower haloalkyl.

13. The compound of claim 8 wherein $R^3$ is amino.

14. The composition of claim 8 being 5-methyl-4-thiazolo[5,4-b]pyridin-2-yl-1H-pyrazazol-3-ylamine.

\* \* \* \* \*